(12) United States Patent
Moll et al.

(10) Patent No.: US 7,865,266 B2
(45) Date of Patent: Jan. 4, 2011

(54) COOPERATIVE MINIMALLY INVASIVE TELESURGICAL SYSTEM

(75) Inventors: Frederic H. Moll, Woodside, CA (US); David J. Rosa, San Jose, CA (US); Andris D. Ramans, Mountain View, CA (US); Steven J. Blumenkranz, Redwood City, CA (US); Gary S. Guthart, Foster City, CA (US); Gunter D. Niemeyer, Mountain View, CA (US); William C. Nowlin, Los Altos, CA (US); J. Kenneth Salisbury, Jr., Los Altos, CA (US); Michael J. Tierney, Pleasanton, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1006 days.

(21) Appl. No.: 10/424,536

(22) Filed: Apr. 24, 2003

(65) Prior Publication Data
US 2003/0216715 A1 Nov. 20, 2003

Related U.S. Application Data

(63) Continuation of application No. 09/433,120, filed on Nov. 3, 1999, now Pat. No. 6,659,939, which is a continuation-in-part of application No. 09/399,457, filed on Sep. 17, 1999, now abandoned, and a continuation-in-part of application No. 09/374,643, filed on Aug. 16, 1999, now abandoned.

(60) Provisional application No. 60/116,891, filed on Jan. 22, 1999, provisional application No. 60/116,842, filed on Jan. 22, 1999, provisional application No. 60/109,359, filed on Nov. 20, 1998.

(51) Int. Cl.
*G06F 19/00* (2006.01)
*G05B 19/18* (2006.01)
*G05B 15/02* (2006.01)
*B25J 1/00* (2006.01)

(52) U.S. Cl. ............................... 700/245; 700/1; 700/2; 700/3; 700/9; 700/11; 414/1; 600/102; 901/6; 901/36

(58) Field of Classification Search ................. 700/245, 700/1, 2, 3, 9, 11; 600/102; 414/1; 901/6, 901/36
See application file for complete search history.

(56) References Cited

U.S. PATENT DOCUMENTS 4,058,001 A 11/1977 Waxman
(Continued)

FOREIGN PATENT DOCUMENTS

| WO | WO 95/01757 | 1/1995 |
| WO | WO 99/09892 | 3/1999 |
| WO | WO 99/50721 | 10/1999 |

OTHER PUBLICATIONS

Graves et al., Dynamic Session Management for Telerobotic Control and Simulation, (1994) IEEE pp. 1740-1745.*
(Continued)

*Primary Examiner*—Khoi Tran
*Assistant Examiner*—Ian Jen

(57) ABSTRACT

Improved robotic surgical systems, devices, and methods include selectably associatable master/slave pairs, often having more manipulator arms than will be moved simultaneously by the two hands of a surgeon. Four manipulator arms can support an image capture device, a left hand tissue manipulation tool, a right hand tissue manipulation tool, and a fourth surgical instrument, particularly for stabilizing, retracting, tool change, or other functions benefiting from intermittent movement. The four or more arms may sequentially be controlled by left and right master input control devices. The fourth arm may be used to support another image capture device, and control of some or all of the arms may be transferred back-and-forth between the operator and an assistant. Two or more robotic systems each having master controls and slave manipulators may be coupled to enable cooperative surgery between two or more operators.

23 Claims, 37 Drawing Sheets

U.S. PATENT DOCUMENTS

| | | | |
|---|---|---|---|
| 4,337,045 A * | 6/1982 | Jones et al. | 434/29 |
| 4,349,837 A | 9/1982 | Hinds | |
| 4,456,961 A | 6/1984 | Price et al. | |
| 4,762,455 A | 8/1988 | Coughlan et al. | |
| 4,826,392 A | 5/1989 | Hayati | |
| 4,863,133 A | 9/1989 | Bonnell | |
| 4,930,494 A | 6/1990 | Takehana et al. | |
| 4,942,538 A | 7/1990 | Yuan et al. | |
| 4,979,949 A | 12/1990 | Matsen, III et al. | |
| 4,989,253 A | 1/1991 | Liang et al. | |
| 5,046,022 A | 9/1991 | Conway et al. | |
| 5,056,031 A | 10/1991 | Nakano et al. | |
| 5,078,140 A | 1/1992 | Kwoh | |
| 5,142,930 A | 9/1992 | Allen et al. | |
| 5,182,641 A | 1/1993 | Diner et al. | |
| 5,217,003 A | 6/1993 | Wilk | |
| 5,217,453 A | 6/1993 | Wilk | |
| 5,251,127 A | 10/1993 | Raab | |
| 5,253,289 A | 10/1993 | Tanaka | |
| 5,271,384 A | 12/1993 | McEwen et al. | |
| 5,279,309 A | 1/1994 | Taylor et al. | |
| 5,284,130 A | 2/1994 | Ratliff | |
| 5,297,034 A * | 3/1994 | Weinstein | 382/128 |
| 5,299,288 A | 3/1994 | Glassman et al. | |
| 5,305,203 A | 4/1994 | Raab | |
| 5,321,353 A | 6/1994 | Furness | |
| 5,339,799 A | 8/1994 | Kami et al. | |
| 5,368,015 A | 11/1994 | Wilk | |
| 5,382,885 A | 1/1995 | Salcudean et al. | |
| 5,397,323 A | 3/1995 | Taylor et al. | |
| 5,402,801 A | 4/1995 | Taylor | |
| 5,408,409 A | 4/1995 | Glassman et al. | |
| 5,417,210 A | 5/1995 | Funda et al. | |
| 5,423,648 A | 6/1995 | Akeel et al. | |
| 5,445,166 A | 8/1995 | Taylor | |
| 5,515,478 A | 5/1996 | Wang | |
| 5,524,180 A | 6/1996 | Wang et al. | |
| 5,571,110 A | 11/1996 | Matsen, III et al. | |
| 5,572,999 A | 11/1996 | Funda et al. | |
| 5,597,146 A | 1/1997 | Putman | |
| 5,613,937 A * | 3/1997 | Garrison et al. | 600/201 |
| 5,630,431 A | 5/1997 | Taylor | |
| 5,631,973 A | 5/1997 | Green | |
| 5,649,956 A | 7/1997 | Jensen et al. | |
| 5,657,429 A | 8/1997 | Wang et al. | |
| 5,695,500 A | 12/1997 | Taylor et al. | |
| 5,696,837 A | 12/1997 | Green | |
| 5,697,939 A | 12/1997 | Kubota et al. | |
| 5,748,767 A | 5/1998 | Raab | |
| 5,749,892 A | 5/1998 | Vierra et al. | |
| 5,754,741 A | 5/1998 | Wang et al. | |
| 5,762,458 A * | 6/1998 | Wang et al. | 414/1 |
| 5,784,542 A | 7/1998 | Ohm et al. | |
| 5,791,908 A | 8/1998 | Gillio | |
| 5,792,135 A | 8/1998 | Madhani et al. | |
| 5,797,900 A | 8/1998 | Madhani et al. | |
| 5,800,423 A | 9/1998 | Jensen | |
| 5,807,243 A | 9/1998 | Vierra et al. | |
| 5,808,665 A | 9/1998 | Green | |
| 5,810,880 A | 9/1998 | Jensen et al. | |
| 5,814,038 A | 9/1998 | Jensen et al. | |
| 5,815,640 A | 9/1998 | Wang et al. | |
| 5,817,084 A | 10/1998 | Jensen | |
| 5,855,553 A | 1/1999 | Tajima et al. | |
| 5,855,583 A | 1/1999 | Wang et al. | |
| 5,859,934 A | 1/1999 | Green | |
| 5,876,325 A * | 3/1999 | Mizuno et al. | 600/102 |
| 5,878,193 A | 3/1999 | Wang et al. | |
| 5,894,843 A | 4/1999 | Benetti et al. | |
| 5,907,664 A | 5/1999 | Wang et al. | |
| 5,911,036 A | 6/1999 | Wright et al. | |
| 5,931,832 A | 8/1999 | Jensen | |
| 5,971,976 A | 10/1999 | Wang et al. | |
| 5,976,122 A | 11/1999 | Madhani et al. | |
| 6,038,641 A | 3/2000 | Zangenehpour | |
| 6,102,850 A | 8/2000 | Wang et al. | |
| 6,132,368 A | 10/2000 | Cooper | |
| 6,132,441 A | 10/2000 | Grace | |
| 6,201,984 B1 | 3/2001 | Funda et al. | |
| 6,205,716 B1 * | 3/2001 | Peltz | 52/36.2 |
| 6,244,809 B1 | 6/2001 | Wang et al. | |
| 6,246,200 B1 | 6/2001 | Blumenkranz et al. | |
| 6,659,939 B2 * | 12/2003 | Moll et al. | 600/102 |

OTHER PUBLICATIONS

Hill et al., Telepresence Technology in Medicine: Principles and Applications, (1998) Proceedings of IEEE pp. 569-580.*

Baumann, Roger "Haptic Interface for Virtual Reality Based Laparoscopic Surgery Training Environment," Thèse No. 1734 (1997)—École Pholytechnique Fédérale de Lausanne. pp. v-178.

Bejczy et al., "A synchronized computational architecture for generalized bilateral control of robot arms," SPIE, Space Station Automation III (1987) vol. 851, pp. 123:134.

Bejczy et al., "Controlling remote manipulators through kinesthetic coupling," Computers in Mechanical Engineering, (Jul. 1983) pp. 48-60.

Bose et al., "Tremor compensation for robotics assisted microsurgery," Annual Intl Conf. of IEEE Engineering in Medicine and Biology Society, (Oct.-Nov. 1992) vol. 14, pp. 1067-1068.

Bowersox et al., "Vascular applications of telepresence surgery: Initial feasibility studies in swine," J. Vascular Surgery (Feb. 1996) vol. 23, No. 2, pp. 281-287.

Christensen et al., "Model based, sensor directed remediation of underground storage tanks," IEEE International Cont. on Robotics and Automation, Sacramento, CA (Apr. 1991) pp. 1377-1383.

Cohn, Michael B., "Medical Robotics," http://www-bsac.eecs.berkeley.edu/~mcenk/medical/, (Nov. 1, 1996) pp. 1-8 and 4 pages.

Elder et al., "Specifying user interfaces for safety-critical medical systems,"2nd Intl. Symposium on Med. Robotics and Comp. Assisted Surgery, Baltimore, Maryland, (Nov. 1995) pp. 148-155.

Computer Motion, Inc., "Automated Endoscopic System for Optimal Positioning," Computer Motion, Inc. Enhancing Performance Through Robotics, 2 pages.

Fu et al., "Robotics: Control, Sensing, Vision, and Intelligence,", McGraw-Hill Book Company, Copyright 1987, 2pages.

Funda et al., "Constrained Cartesian Motion Control for Teleoperated Surgical Robots," IEEE Transactions on Robotics and Automation, (Jun. 1996) vol. 12, No. 3, pp. 453-465.

Gayed et al., "An advanced control micromanipulator for surgical applications," Systems Science, vol. 13, 123-133.

Goertz et al., "ANL mark E4A electric master-slave manipulator," Proc. 14th Conf. oOn Remote System Technology, pp. 115-123.

Green et al., "Mobile telepresence surgery," 2nd Annual Intl Symposium on Med. Robotics and Computer Assisted Surgery, Maryland (Nov. 1995) pp. 97-103.

Heer, Ewald, "Remotely Manned Systems: Exploration and Operation in Space," Proceedings of the First National Conference, Pasadena, CA (Sep. 13-15, 1972) pp. 449-458 and 483-492.

Hill et al., "Telepresence surgery demonstration system," IEEE 1994, pp. 2302-2307.

Holler et al., "An ATM-based local communication system for telesurgery," Interactive Tech. and New Paradigm Healthcare, pp. 137-146.

Huteau et al., "Laparoscopic surgery assisted by a robotic cameraman: Concept and experimental results," IEEE Intl. Conf. Robotics and Automation, San Diego, CA, (May 1994) pp. 2286-2289.

Hunter et al., "A teleoperated microsurgical robot and associated virtual environment for eye surgery," Presence, vol. 2, No. 4, pp. 265-280.

Ikuta et al., "Hyper redundant active endoscope for minimum invasive surgery," Dept. Micro System Eng., Nagoya University, Japan, pp. 230-237.

Kazerooni, H., "Human/robot interactive via the transfer of power and information signals," IEEE (1989) pp. 1632-1640.

Lazarevic, Zoran, "Feasibility of a Stewart Platform with fixed actuators as a platform for CABG surgery device," Master's Thesis (Oct. 10, 1997) 29 pages.

Mack et al., "Video-assisted coronary bypass grafting on the beating heart," Ann. Thorac. Surg., (1997) 63:S100-S103.

Neisius et al., "Robotic manipulator for endoscopic handling of surgical effectors and cameras," 1st Int'l Symposium on Medical Robotics and Computer Assisted Surgery, (Sep. 22-24, 1994) pp. 169-175.

Preising et al., "A literature review: Robots in medicine," IEEE Engineering in Medicine and Biology (Jun. 1991) pp. 13-71.

Rovetta et al., "The first experiment in the world of robotic telesurgery for laparoscopy carried out by means of satellites networks and optical fibers networks on 7th Jul. 1993," IEEE (1993) pp. 51-56.

Sabatini et al., "Force feedback-based telemicromanipulation for robot surgery on soft tissues," IEEE Engineering in Medicine & Biology Society, (1989) pp. 890-891.

Schenker et al., "Development of a telemanipulator tor dexterity enhanced microsurgery," 2nd Intl. Symposium on MRCAS '95, Baltimore, Maryland, Nov. 5-7, 1995) 9 pages.

Sastry, Shankar "Millirobotics for Remote, Minimally-Invasive Surgery," Proceedings of the Int'l. Workshop on Some Critical Issues in Robotics (Singapore, Oct. 2-3, 1995) 81-98 pages.

Stevens, Jane E., "Cyber Surgery, Computers, cameras and robots are creating an improved operating system for doctors," Los Angeles Times (Thursday, Nov. 30, 1995) p. 12.

Taub, Gary, "Surgery in cyberspace," Discover (Dec. 1994) pp. 84-92.

Taylor et al., "Research Report: A telerobotic assistant for laparoscopic surgery," Accepted to IEEE EIMBS Magazine, Special Issue on "Robotics in Surgery," (Dec. 1994) pp. 1-21.

Taylor et al., "A telerobotic assistant for laparoscopic surgery," IEEE Engineering in Medicine and Biology, (May/Jun. 1995) pp. 279-288.

Thring, M.W., "Robots and Telechirs: Manipulators with memory; remote manipulators; machine limbs for the handicapped," Ellis Horwood Limited (1983) Ch. 5, Sec. 5.4, pp. 9-279.

Wapler, M. "Medical manipulators—A Realistic Concept?," Blackwell Science Ltd., Minimally Invasive Therapy (1995) vol. 4, pp. 261-266.

* cited by examiner

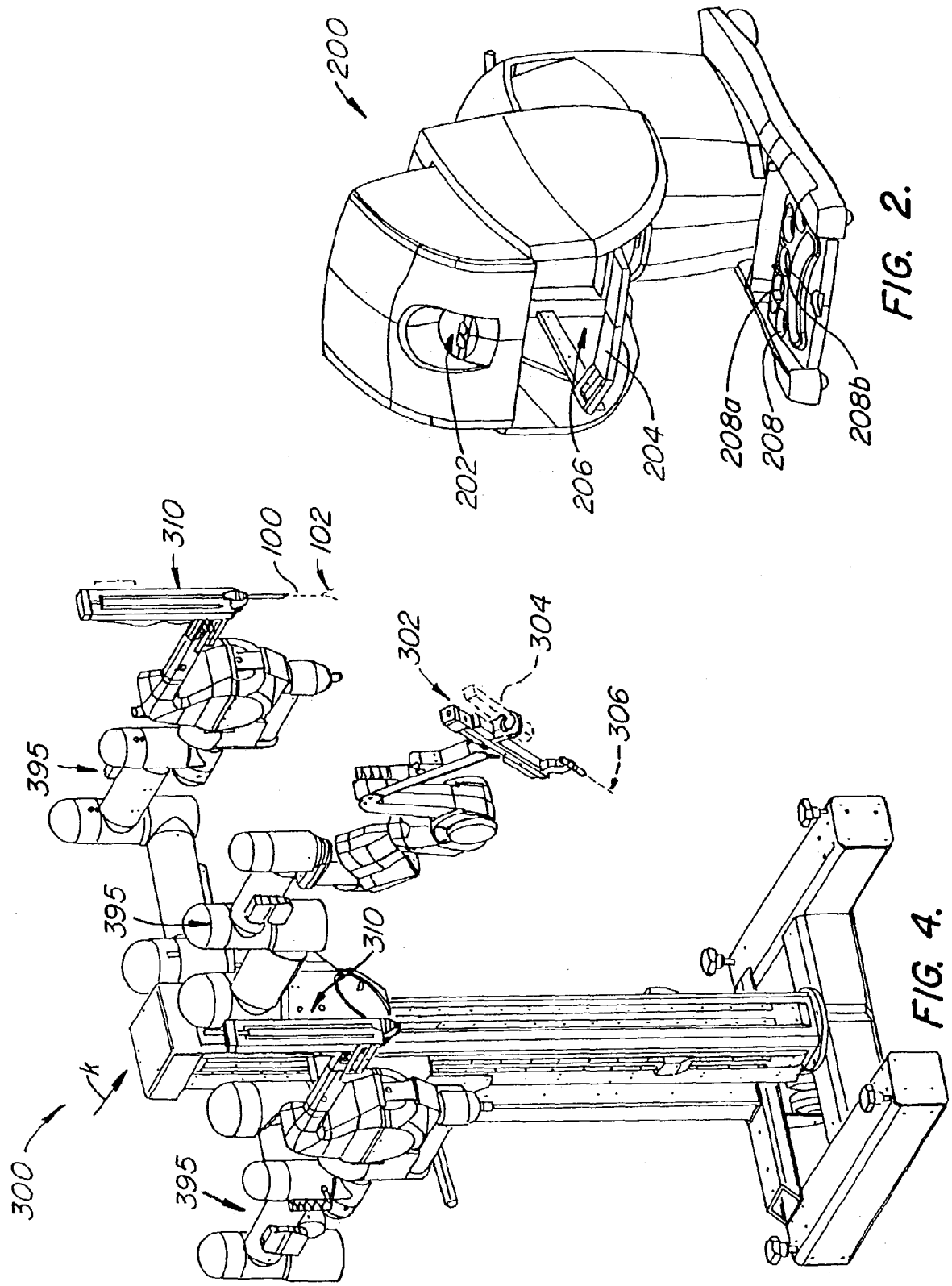

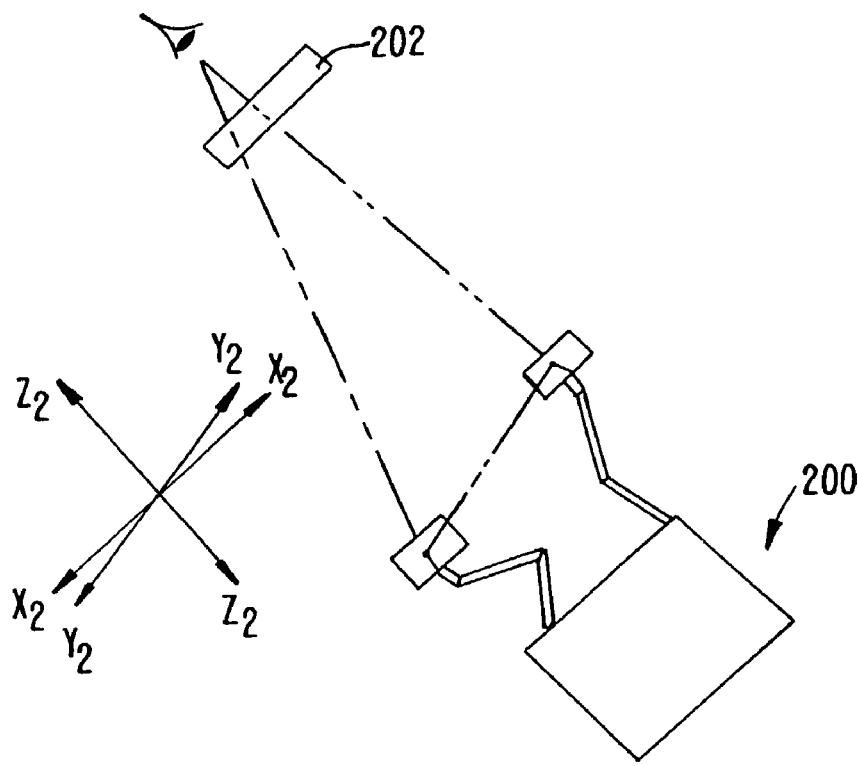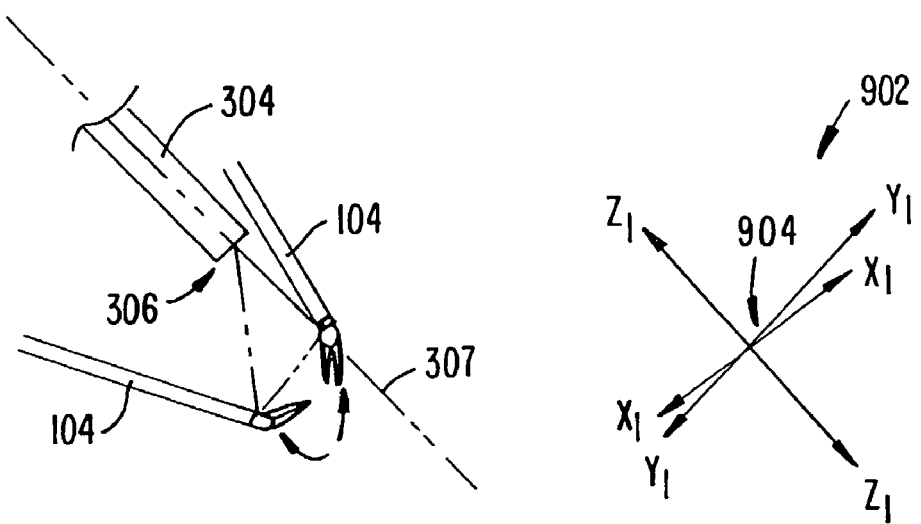
FIG. 10.

ASSOCIATE  TOOL A ⟷ LEFT MASTER
          TOOL B ⟷ RIGHT MASTER

ASSOCIATE TOOL A ⟷ LEFT MASTER
TOOL B ⟷ RIGHT MASTER

ASSOCIATE TOOL A ⟷ RIGHT MASTER
TOOL B ⟷ LEFT MASTER

COOPERATIVE MINIMALLY INVASIVE TELESURGICAL SYSTEM

CROSS-REFERENCES TO RELATED APPLICATIONS

The present application is a continuation of application Ser. No. 09/433,120, filed Nov. 3, 1999, now U.S. Pat. No. 6,659, 939, for a "Cooperative Minimally Invasive Telesurgical System", which was a continuation-in-part of and claims the benefit of priority from application Ser. No. 09/399,457, filed Sep. 17, 1999 now abandoned for a "Cooperative Minimally Invasive Telesurgical System"; application Ser. No. 09/374, 643, (Abandoned), filed Aug. 16, 1999 now abandoned for a "Cooperative Minimally Invasive Telesurgical System"; and also claims the benefit of priority from Provisional Application Ser. No. 60/116,891, filed Jan. 22, 1999, for "Dynamic Association of Master and Slave in a Minimally Invasive Telesurgical System"; Provisional Application Ser. No. 60/116,842, filed Jan. 22, 1999, for "Repositioning and Reorientation of Master/Slave Relationship in Minimally Invasive Telesurgery"; and Provisional Application Ser. No. 60/109,359, filed Nov. 20, 1998, for "Apparatus and Method for Tracking and Controlling Cardiac Motion During Cardiac Surgery Without Cardioplegia"; the full disclosures of which are incorporated herein by reference.

BACKGROUND OF THE INVENTION

The present application is generally directed to medical devices, systems, and methods. In a particular embodiment, the invention provides telesurgical robotic systems and methods that flexibly and selectably couple input devices to robotic manipulator arms during surgery.

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch or less) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, image capture lenses, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

There are many disadvantages relating to current minimally invasive surgical (MIS) technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

While the proposed robotic surgery systems offer significant potential to increase the number of procedures that can be performed in a minimally invasive manner, still further improvements are desirable. In particular, previous proposals for robotic surgery often emphasize direct replacement of the mechanical connection between the handles and end effectors of known minimally invasive surgical tools with a robotic servomechanism. Work in connection with the present invention suggests that integration of robotic capabilities into the operating theater can benefit from significant changes to this one-to-one replacement model. Realization of the full potential of robotically assisted surgery may instead benefit from significant revisions to the interactions and roles of team members, as compared to the roles performed by surgical team members during open and known minimally invasive surgical procedures.

In light of the above, it would be beneficial to provide improved robotic surgical devices, systems, and methods for performing robotic surgery. It would be beneficial if these improved techniques enhanced the overall capabilities of telesurgery by recognizing, accommodating, and facilitating the new roles that may be performed by the team members of a robotic surgical team. It would further be beneficial if these improvements facilitated complex robotic surgeries such as coronary artery bypass grafting, particularly while minimizing the total number of personnel (and hence the expense) involved in these robotic procedures. It would be best if these benefits could be provided while enhancing the overall control over the surgical instruments and safety of the surgical procedure, while avoiding excessive complexity and redundancy in the robotic system. Some or all of these advantages are provided by the invention described hereinbelow.

SUMMARY OF THE INVENTION

The present invention provides improved robotic surgical systems, devices, and methods. The robotic surgical systems of the present invention will often include a plurality of input devices and/or a plurality of robotic manipulator arms for moving surgical instruments. A processor will often selectably couple a selected input device to a selected manipulator arm, and allows modification of the operative association so that that same input device can be coupled to a different manipulator arm, and/or so that that same manipulator arm can be controlled by a different input device. This selective coupling, for example, allows the controller to properly assign left and right surgical end effectors to left and right input devices for use by an operator viewing the procedure via an image capture device. When the image capture devices moves, the operative associations can be revised. In some embodiments, the image capture device may be removed from one of the manipulator arms and instead mounted to another of the manipulator arms, with the left and right input devices reassigned so as to avoid an awkward surgical environment for the system operator sitting at a master control station.

The systems of the present invention will often include more manipulator arms than will be moved simultaneously by a single surgeon. In addition to an imaging arm (movably supporting an image capture device) and two manipulator arms (holding selectably designated "left" and "right" surgical tools for manipulation by left and right hands of the system operator, e.g.), one or more additional manipulator arms will often be provided to position associated surgical instrument(s). At least one of the additional manipulator arms may be maintained in a stationary configuration to stabilize or retract tissue while the operator moves left and right input devices with his or her left and right hands to manipulate tissues with the associated surgical tools. The one or more additional arms may also be used to support another image capture device, often a second endoscope to view the internal surgical site from an alternative vantage point. Additional arms may optionally provide one or more additional surgical tools for manipulating tissue or aiding in the performance of a procedure at a surgical site. To manipulate this additional surgical instrument, an assistant input device may optionally be provided so that an assistant (such as an assisting surgeon at another workstation, a surgical nurse at the patient's side, or the like) can position the additional robotic arm(s). Regardless of the presence or absence of such an assistant input device, the robotic surgical systems of the present invention will preferably allow the system operator to selectively associate the right and/or left input devices of the surgical workstation with any of a plurality of surgical instruments.

In a first aspect, the invention provides a robotic surgical system comprising a first input device manipulatable by a hand of an operator. A first robotic arm assembly includes a first manipulator arm for moving a first surgical instrument. A second robotic arm assembly includes a second manipulator arm for moving a second surgical instrument. A control system couples the first input device to the first and second robotic arm assemblies. The control system permits selective operative association of the first input device with the first robotic arm assembly, and also permits selective operative association of the first input device with the second robotic arm assembly.

Typically, the control system will have a plurality of selectable modes, with manipulation of the first input device effecting corresponding movement of the first surgical instrument in one mode, and with the same manipulation of the first input device effecting corresponding movement of the second surgical instrument in a second mode. In some embodiments, a second input device may be used to effect corresponding movement of the second surgical instrument when the control system is in the first mode, and effect corresponding movement of the first surgical instrument when the control system is in the second mode, allowing swapping control of the surgical instruments between the input devices. This is particularly useful when the system operator is controlling the first and second input devices using left and right hands with reference to an image of an internal surgical site, as it allows the system operator to switch tools when the image capture device providing the image moves to what would otherwise be an awkward position.

In another aspect, the invention provides a robotic surgical system comprising a plurality of input devices and a plurality of manipulator arms, each manipulator arm having an instrument holder. A plurality of surgical instruments are mountable to the instrument holders, the surgical instruments including an image capture device and a tool having a surgical end effector for treating tissue. A control system couples the input devices with the manipulator arms. The control system selectably associates each input device with a manipulator arm.

In some embodiments, the image capture device may be removed from one manipulator arm and mounted to an alternative manipulator arm, often with the control system being reconfigurable so that the input devices are operatively associatable with manipulator arms holding tools for treating tissue. A particularly advantageous control system is provided which allows this flexible pairing of input devices and manipulator arms.

In a specific aspect, the invention provides a minimally invasive robotic surgical system comprising two input devices and at least two medical instrument robotic arm assemblies. One of the input devices is operatively associated with one of the robotic arm assemblies to cause movement of the robotic arm assembly in response to inputs on the input device. The other input device is operatively associated with another of the robotic arm assemblies to cause movement of that other robotic arm assembly in response to inputs on that other input device. A control system couples the input devices with the robotic arm assemblies. The control system enables selective swapping so as to cause the input device to be operatively associated with the robotic arm assembly which was operatively associated with the other input device, and to cause the other input device to be operatively associated with the robotic arm assembly which was operatively associated with the input device. Related systems allow selective operative association between at least one of the input devices and an image capture robotic arm assembly to permit the position of an image capture device to be changed using the at least one input device.

In a method aspect, the invention provides a robotic surgical method comprising robotically moving a first surgical instrument using a first manipulator arm by manipulating a first input device with a hand. A control system is reconfigured by entering a command. The control system couples the first input device with the first manipulator arm, and also with a second manipulator arm. A second surgical instrument is moved robotically using the second manipulator arm by manipulating the input device with the hand after the reconfiguring step.

In a related method, a robotic surgical method comprises robotically moving a surgical instrument using a manipulator arm by manipulating a first input device with a first hand. A control system is reconfigured by entering a command. The control system couples the first input device, and also a second input device, with the manipulator arm. The surgical instrument is robotically moved using the manipulator arm by manipulating the second input device with a second hand after the reconfiguring step.

In another aspect, the invention provides a robotic surgical system comprising an imaging system transmitting an image from an image capture device to a display. First, second, and third manipulator arms each support an associated surgical instrument. A master controller is disposed adjacent the display. The master has a first input device manipulatable by a first hand of an operator, and a second input device manipulatable by a second hand of the operator. A processor operatively couples each input device of the master to an associated manipulator arm so that movement of the input device effects movement of the associated surgical instrument.

In some embodiments, the surgical instrument associated with the third arm will comprise another image capture device. Where two image capture devices are included in the system, the processor will preferably transmit arm movement command signals to the arms according to different coordinate system transformations depending on which image capture device is providing the image currently shown on the display. This allows the processor to correlate between a direction of movement of the input device and the movement of the surgical instrument when switching between two different endoscopes having different fields of view.

Preferably, at least the third robotic instrument arm should be configurable to maintain a stationary configuration under some circumstances, with the arm in the stationary configuration inhibiting movement of the associated surgical instrument despite movement of the input devices. Such a stationary configuration is particularly useful when the surgical instrument mounted on the third arm comprises a stabilizer (such as a coronary tissue stabilizer used for beating heart surgery) or a retractor (for example, to retract tissue to expose a desired area of the cystic duct to the surgeon during cholecystectomy). The third arm will often comprise a linkage having a series of joints, and a brake system coupled to the joints to releasably inhibit articulation of the linkage. The third arm linkage will preferably also have a repositionable configuration allowing manual articulation of the arm, and at least some of the arms will often remain stationary and/or be repositionable in response to a signal. In addition to comprising a robotic manipulator arm having a driven configurations, the third arm may alternatively comprise a simple passive linkage with a brake system but without actuators.

Preferably, the surgical system will include four or more robotic manipulator arms. One of the additional arms may support an image capture device of the imaging system. To allow the operator to selectively manipulate all of these surgical instruments, including the image capture device, the processor will have an operation mode in which the first arm moves its associated surgical instrument at the surgical site in response to movement to the first input device, while the second arm moves its associated surgical instrument in response to movement of the second input device. In response to an arm selection signal from at least one arm selector input coupled to the processor, the processor can selectively change operating modes by decoupling the first arm from the first input device, and instead operatively couple the first input device with the second arm, the third arm, or the fourth arm. The processor will maintain some (or ideally all) of the decoupled arms in the stationary configuration under some circumstances, although a decoupled arm could be controlled to move in a repetitive or automated manner until recoupled to the surgeon's input device. An example of such automated motion of a decoupled robotic arm includes motion tracking of a beating heart.

The robotic surgical system will often include an assistant input device. The processor can selectively associate one or more of the arms with the assistant input device, or with an input device of the surgeon, so that the one arm moves in response to movement of the selected input device. Hence, the processor can "hand-off" control of at least one arm (and its associated surgical instrument) between surgeon and assistant input stations. This may be useful when the assistant is removing and replacing the surgical instrument from the arm or when the assistant at a second console is to perform a part of the surgical procedure such as "closing" a portion of the surgical site. This also allows the surgeon to selectively assign direct control over an instrument based on the skill required to use the instrument for a given task, thereby enhancing robotic team effectiveness. The assistant may optionally be working at an assistant control station that can correlate direction of movement of the assistant input device with an image of the end effector shown in an assistant display. The "assistant" image might be either a different image from a second endoscope or a shared image from the primary console's endoscope, thereby enabling the surgeon and assistant to view the same image of the surgical site and manipulate each of their assigned and coupled instruments to cooperate in performing a surgical procedure. Alternatively, a simple video monitor and assistant input device (such as a handle within the sterile field) may be provided for the assistant, particularly for a patient-side assistant performing tool swaps, intermittent irrigation, or the like. In other embodiments, the surgeon's ability to select from among three or more surgical instruments, and to selectively associate each instrument with each of the input devices, will reduce and/or eliminate the need for surgical assistants. Decreasing the use of surgical assistants (and the time to continually direct and oversee the assistant's movements) can significantly decrease the time and expense of a surgical procedure.

Typically, for a system having four arms, for example, three surgical instruments and the image capture device will be supported by four manipulators each comprising an endoscopic instrument having an elongate shaft with a proximal end adjacent the manipulator and a distal end insertable into an internal surgical site within a patient body through a minimally invasive surgical aperture. Preferably, the manipulators will support the surgical instrument so that the shafts extend radially outwardly from a pattern of apertures (typically incisions) in a "spoked wheel"-type arrangement. In an exemplary arrangement for performing cardiac surgery, the four shafts will be sufficiently long to enter apertures on the right side of the patient body, and to extend toward the left side of the patient body for treating the heart. During at least a portion of the procedure, top and bottom apertures of the pattern may accommodate first and second endoscopes to provide flexibility in the field of view, particularly for the separate steps of harvesting a suitable supply artery and forming of the anastomosis during coronary artery bypass grafting (CABG). Additional ports can support additional surgical tools. When performing a CABG procedure without cardioplegia on a beating heart, at least one of the apertures of the pattern will often accommodate a tissue stabilizer during at least a portion of the procedure.

In another aspect, the invention provides a robotic surgical system comprising a plurality of manipulator arms and a plurality of surgical instruments, each instrument mounted to an associated arm. A master controller station has a master display for viewing by an operator, a first input device for manipulation by a first hand of the operator, and a second input device for manipulation by a second hand of the operator. An assistant input device for manipulation by a hand of an assistant is also provided. Preferably, a processor selectively operatively couples the controllers to the arms to effect movement to the surgical instruments in response to movement of the input devices.

In a method aspect, the invention provides a robotic surgical method comprising robotically moving first and second surgical instruments at a surgical site with first and second robotic manipulator arms by manipulating first and second input devices with first and second hands of the operator, respectively. The first input device is selectively associatable with a third manipulator arm, so that a third surgical instrument can be robotically moved at the surgical site with the third manipulator arm by manipulating the first input device with the first hand of the operator.

In another method aspect, the invention provides a robotic surgical method comprising robotically moving first and second surgical instruments at a surgical site with first and second robotic manipulator arms by manipulating first and second input devices with first and second hands of the operator, respectively. A third surgical instrument is positioned at the surgical site by articulating a linkage of a third manipulator. Movement of the positioned third surgical instrument is impeded at the surgical site by inhibiting movement of the third manipulator.

In yet another method aspect, the invention provides a robotic surgical method comprising robotically positioning a surgical instrument at a surgical site with a manipulator arm by manipulating a first input device with a hand of a first operator. The manipulator arm is selectively associated with a second input device, and the surgical instrument is robotically moved at the surgical site with the manipulator arm by manipulating the second input device with a hand of a second operator.

In a still further method aspect, the invention provides a robotic surgical method comprising showing, on a display, a first view of a surgical site from a first image capture device. A surgical instrument is robotically removed at the surgical site with a manipulator arm by manipulating an input device with a hand of an operator while the operator views the first view of the surgical site on the display. A second image capture device is selectively associated with the display, and the surgical instrument is robotically manipulated at the surgical site with the arm by manipulating the input device while the operator views a second view of the surgical site from the second image capture device on the display.

In yet another method aspect, the invention provides a robotic coronary artery bypass grafting method comprising introducing an image capture device into a chest cavity of a patient through an aperture disposed along a right side of the patient. An image of a surgical site adjacent the heart is displayed from the image capture device to an operator. A surgical procedure is performed on the heart by moving a surgical instrument at the surgical site with at least one robotic manipulator arm while the surgical instrument extends through another aperture disposed along the right side of the patient. Preferably, tissue manipulation during the surgical procedure will primarily be performed by surgical tools extending through a pattern of apertures along the right side of the patient.

In another aspect, first and second robotic manipulators are controlled by a first operator with first and second controllers, and third and fourth manipulators are controlled by a second operator with third and fourth controllers. Both operators view an image of the operating site captured by a single image capture device, and both cooperate to perform a surgical procedure. Each operator may have a separate dedicated viewing station for his use. Such cooperation may include helping each other perform the procedure, passing objects back and forth between manipulators during the procedure, and passing control of various of the manipulator arms. Both sets of manipulators may share the same reference point so that control may be transferred without loss of context.

BRIEF DESCRIPTION OF THE DRAWINGS

The invention will now be described, by way of example, and with reference to the accompanying diagrammatic drawings, in which:

FIG. 2 shows a three-dimensional view of a control station of a telesurgical system in accordance with the invention;

FIG. 4 shows a three-dimensional view of a cart of the telesurgical system in accordance with the invention, the cart carrying three robotically controlled manipulator arms, the movement of the arms being remotely controllable from the control station shown in FIG. 2;

FIG. 10 shows a schematic three-dimensional drawing indicating the positions of the end effectors relative to a viewing end of an endoscope and the corresponding positions of master control input devices relative to the eyes of an operator, typically a surgeon;

DESCRIPTION OF THE SPECIFIC EMBODIMENTS

Figure 1:
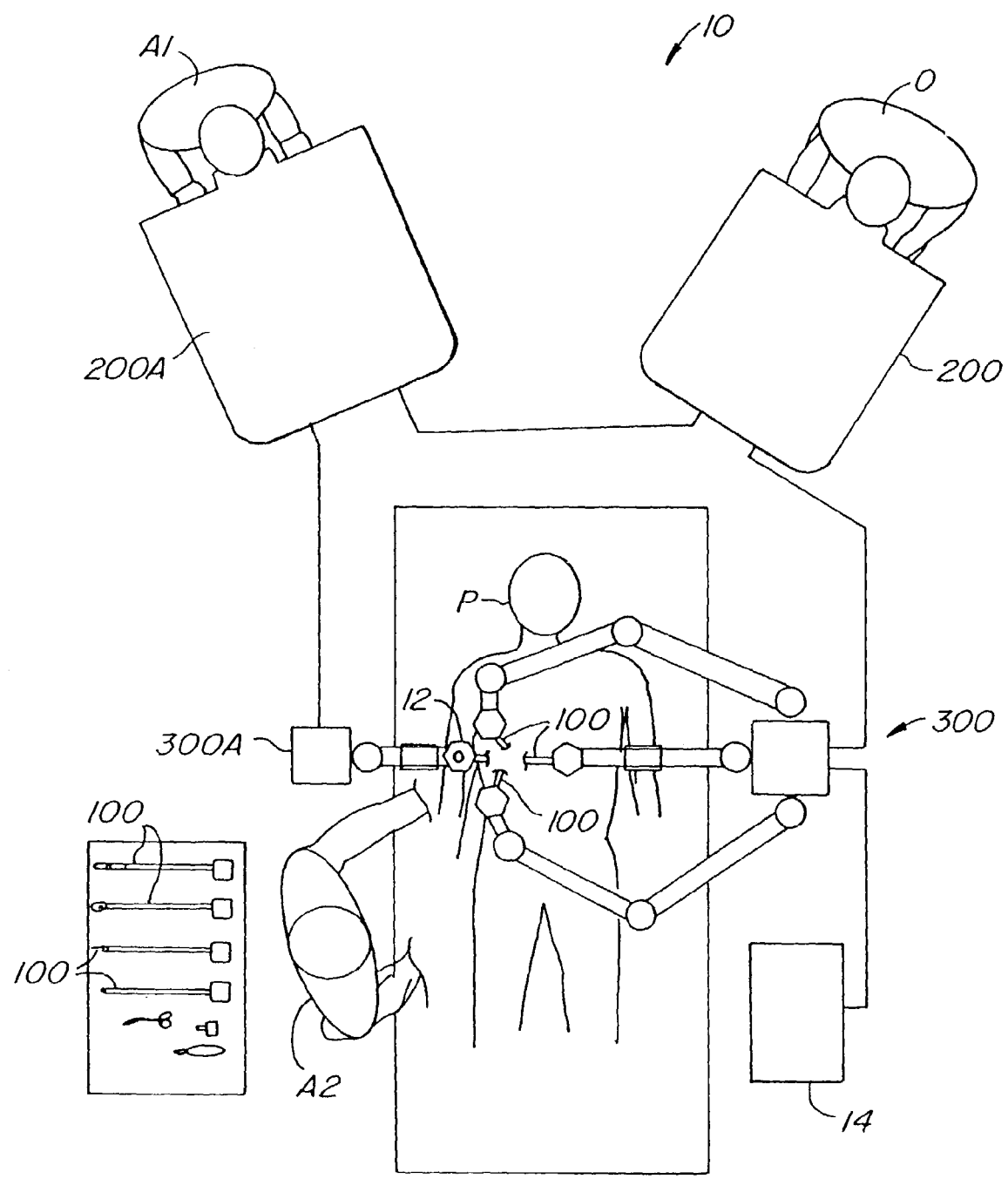
FIG. 1 is a plan view of a telesurgical system and method for performing a robotic minimally invasive surgical procedure.

This application is related to the following patents and patent applications, the full disclosures of which are incorporated herein by reference: PCT International Application No. PCT/US98/19508, entitled "Robotic Apparatus", filed on Sep. 18, 1998, U.S. Pat. application Serial No. 60/111,713, entitled "Surgical Robotic Tools, Data Architecture, and Use", filed on Dec. 8, 1998; U.S. patent application Ser. No. 60/111,711, entitled "Image Shifting for a Telerobotic System", filed on Dec. 8, 1998; U.S. patent application Ser. No. 60/111,714, entitled "Stereo Viewer System for Use in Telerobotic System", filed on Dec. 8, 1998; U.S. patent application Ser. No. 60/111,710, entitled "Master Having Redundant Degrees of Freedom", filed on Dec. 8, 1998, U.S. patent application No. 60/116,891, entitled "Dynamic Association of Master and Slave in a Minimally Invasive Telesurgery System", filed on Jan. 22, 1999; and U.S. Pat. No. 5,808,665, entitled "Endoscopic Surgical Instrument and Method for Use," issued on Sep. 15, 1998.

As used herein, first and second objects (and/or their images) appear "substantially connected" if a direction of an incremental positional movement of the first object matches the direction of an incremental positional movement of the second object (often as seen in an image), regardless of scaling between the movements. Matching directions need not be exactly equal, as the objects (or the object and the image) may be perceived as being connected if the angular deviation between the movements remains less than about ten degrees, preferably being less than about five degrees. Similarly, objects and/or images may be perceived as being "substantially and orientationally connected" if they are substantially connected and if the direction of an incremental orientational movement of the first object is matched by the direction of an incremental orientational movement of the second object (often as seen in an image displayed near the first object), regardless of scaling between the movements.

Additional levels of connectedness may, but need not, be provided. "Magnitude connection" indicates substantial connection and that the magnitude of orientational and/or positional movements of the first object and second object (typically as seen in an image) are directly related. The magnitudes need not be equal, so that it is possible to accommodate scaling and/or warping within a magnitude connected robotic system. Orientational magnitude connection will imply substantial and orientational connection as well as related orientational movement magnitudes, while substantial and magnitude connection means substantial connection with positional magnitudes being related.

As used herein, a first object appears absolutely positionally connected with an image of a second object if the objects are substantially connected and the position of the first object and the position of the image of the second object appear at least to substantially match, i.e., to be at the same location, during movement. A first object appears absolutely orientationally connected with an image of the second object if they are substantially connected and the orientation of the first object and the second object at least substantially match during movement.

Referring now to FIG. 1, a robotic surgical network 10 includes a master control station 200 and a slave cart 300, along with any of several other additional components to enhance the capabilities of the robotic devices to perform complex surgical procedures. An operator O performs a minimally invasive surgical procedure at an internal surgical site within patient P using minimally invasive surgical instruments 100. Operator O works at master control station 200. Operator O views a display provided by the workstation and manipulates left and right input devices. The telesurgical system moves surgical instruments mounted on robotic arms of slave cart 300 in response to movement of the input devices. As will be described in detail below, a selectably designated "left" instrument is associated with the left input device in the left hand of operator O, and a selectably designated "right" instrument is associated with the right input device in the right hand of the operator.

As described in more detail in co-pending U.S. patent application Ser. No., 09/373,678 entitled "Camera Referenced Control In A Minimally Invasive Surgical Apparatus" and filed Aug. 13, 1999, the full disclosure of which incorporated herein by reference, a processor of master controller 200 will preferably coordinate movement of the input devices with the movement of their associated instruments so that the images of the surgical tools 100, as displayed to the operator, appear at least substantially connected to the input devices in the hands of the operator. Further levels of connection will also often be provided to enhance the operator's dexterity and case of use of surgical instruments 100.

Introducing some of the other components of network 10, an auxiliary cart 300A can support one or more additional surgical tools 100 for use during the procedure. One tool is shown here for illustrative purposes only. A first assistant A1 is seated at an assistant control station 200A, the first assistant typically directing movements of one or more surgical instruments not actively being manipulated by operator O via master control station 200. A second assistant A2 may be disposed adjacent patient P to assist in swapping instruments 100 during the surgical procedure. Auxiliary cart 300A may also include one or more assistant input devices 12 (shown here as a simple joy stick) to allow second assistant A2 to selectively manipulate the one or more surgical instruments while viewing the internal surgical site via an assistant display 14. Preferably, the first assistant A1 seated at console 200A views the same image as surgeon seated at console 200. Further preferably, both the instruments of cart 300 and the "assistant" instruments of cart 300A are controlled according to the same camera reference point, such that both surgeon and assistant are able to be "immersed" into the image of the surgical field when manipulating any of the tools.

Figure 26:
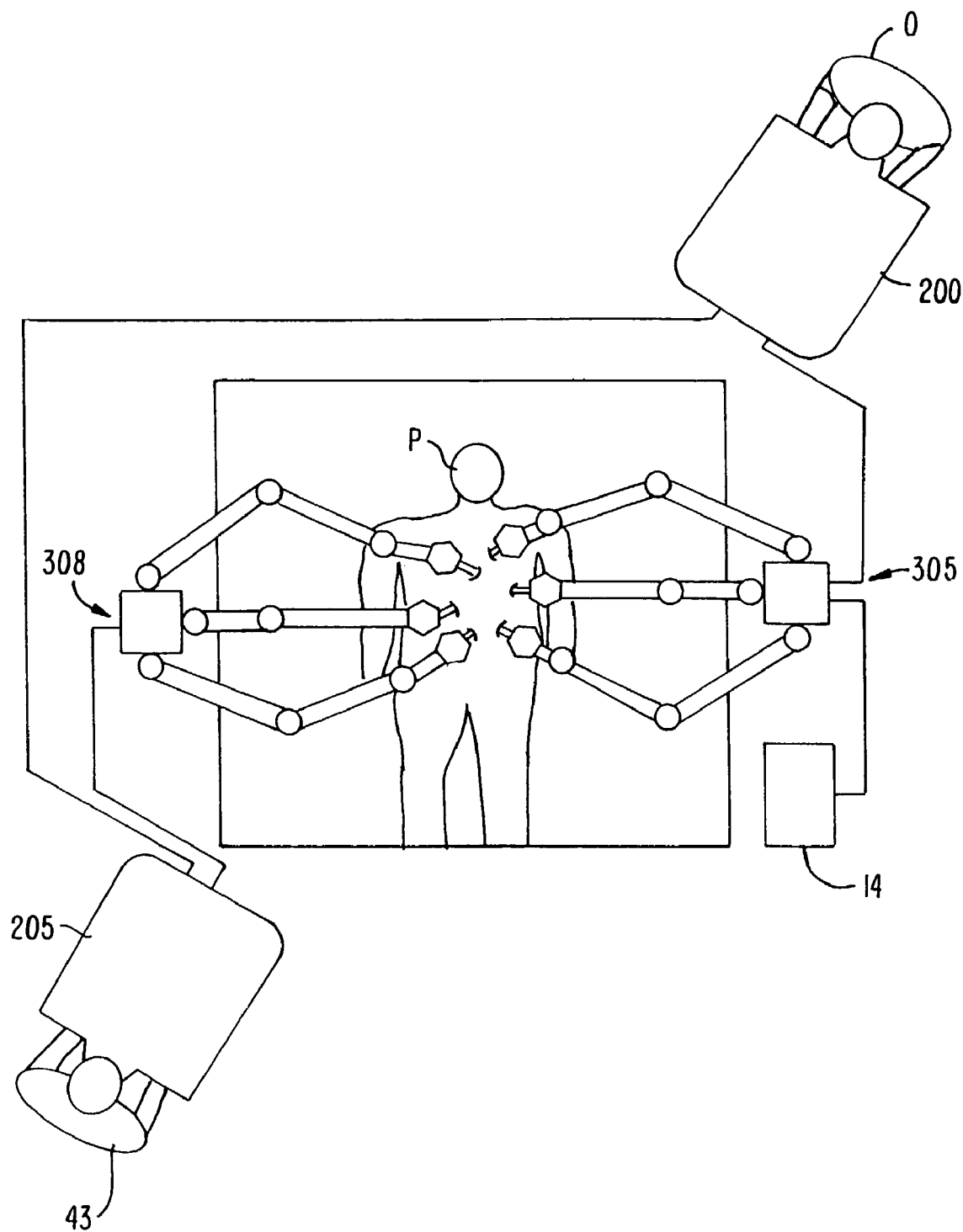
FIGS. 26 and 27 schematically illustrate alternative robotic telesurgical systems.
Figure 27:
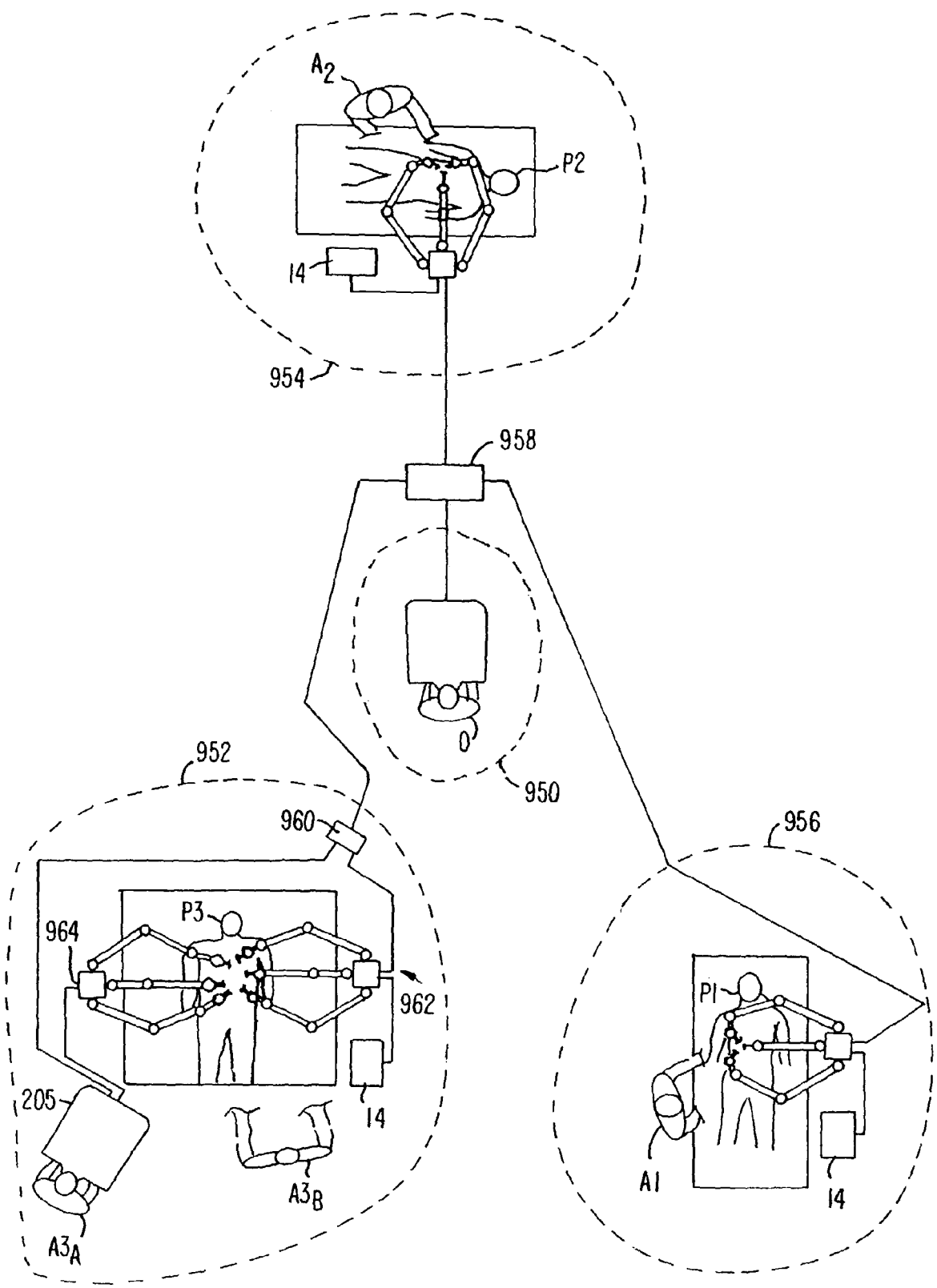

As will be described hereinbelow, master control station 200, assistant controller 200A, cart 300, auxiliary cart 300A, and assistant display 14 (or subsets of these components) may allow complex surgeries to be performed by selectively handing-off control of one or more robotic arms between operator O and one or more assistants. Alternatively, operator O may actively control two surgical tools while a third remains at a fixed position, for example, to stabilize and/or retract tissue, with the operator selectively operating the retractor or stabilizer only at designated times. In still further alternatives, a surgeon and an assistant can cooperate to conduct an operation without either passing control of instruments or being able to pass control of the instruments, with both instead manipulating his or her own instruments during the surgery, as will be described below with reference to FIG. 26. Although FIG. 1 depicts two surgeon consoles controlling the two cart structures, a preferred embodiment comprises only one console controlling four or more arms on two carts. The scope may optionally be mounted on the auxiliary cart and three tissue manipulator arms may be mounted on the main cart. Generally, the use of robotic systems having four or more arms will facilitate complex robotic surgical procedures, including procedures that benefit from selectable endoscope viewing angles. Methods for using robotic network 10 will be described in more detail following descriptions of the network components. While the network component connections are schematically illustrated in FIGS. 1, 26, and 27, it should be understood that more complex interconnections between the various network components may be provided.

Component Descriptions. Referring to FIG. 2 of the drawings, the control station of a minimally invasive telesurgical system in accordance with the invention is generally indicated by reference numeral 200. The control station 200 includes a viewer or display 202 where an image of a surgical site is displayed in use. A support 204 is provided on which an operator, typically a surgeon, can rest his or her forearms while gripping two master controls (FIGS. 3A and 3B), one in each hand. The master controls are positioned in a space 206 inwardly beyond the support 204. When using control station 200, the surgeon typically sits in a chair in front of the control station 200, positions her eyes in front of the viewer 202, and grips the master controls, one in each hand, while resting her forearms on the support 204.

Figure 3A:
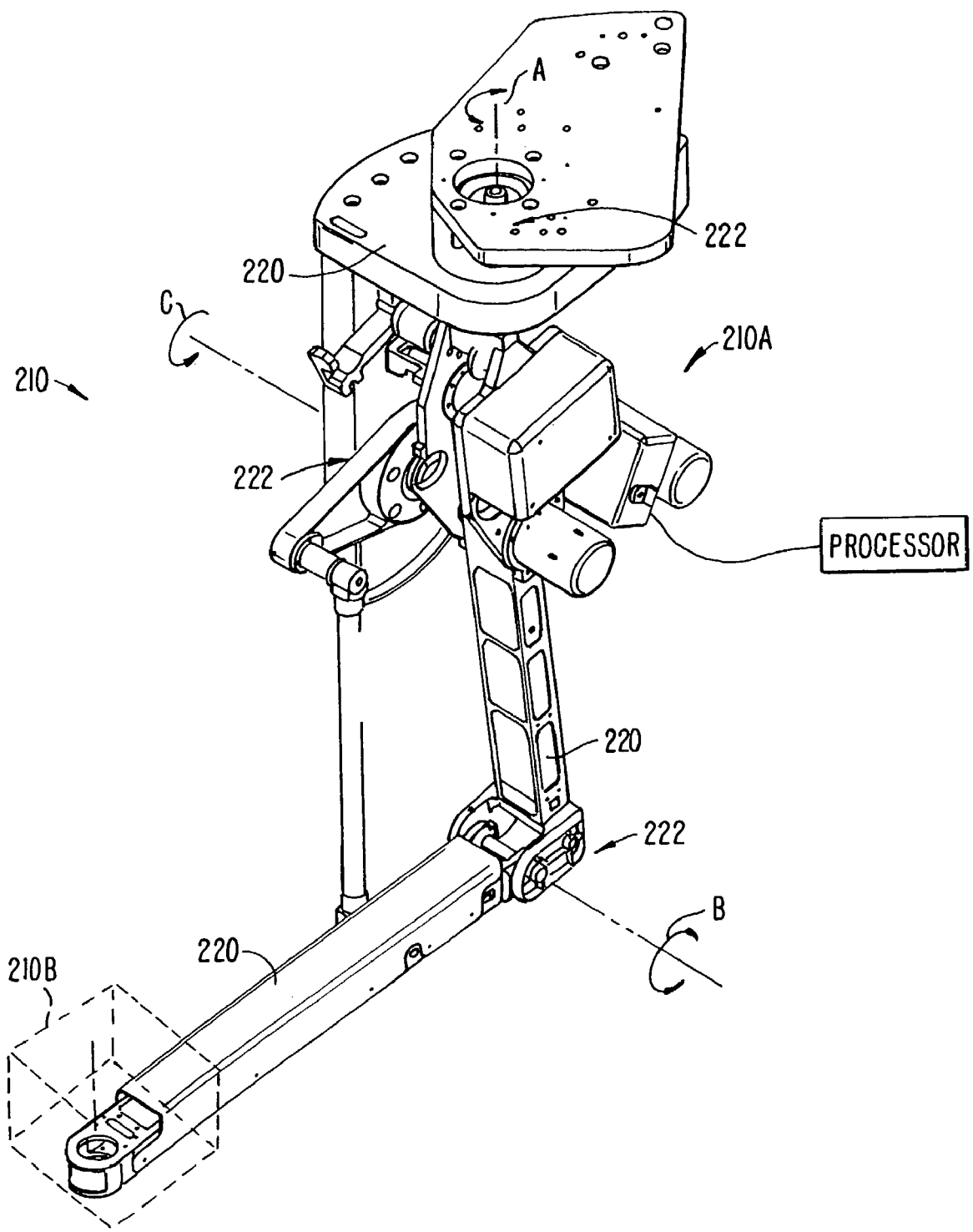
FIGS. 3A-C show three-dimensional views of an input device including an articulated arm and wrist to be mounted on the arm for use in the master control station of FIG. 2.
Figure 3B:
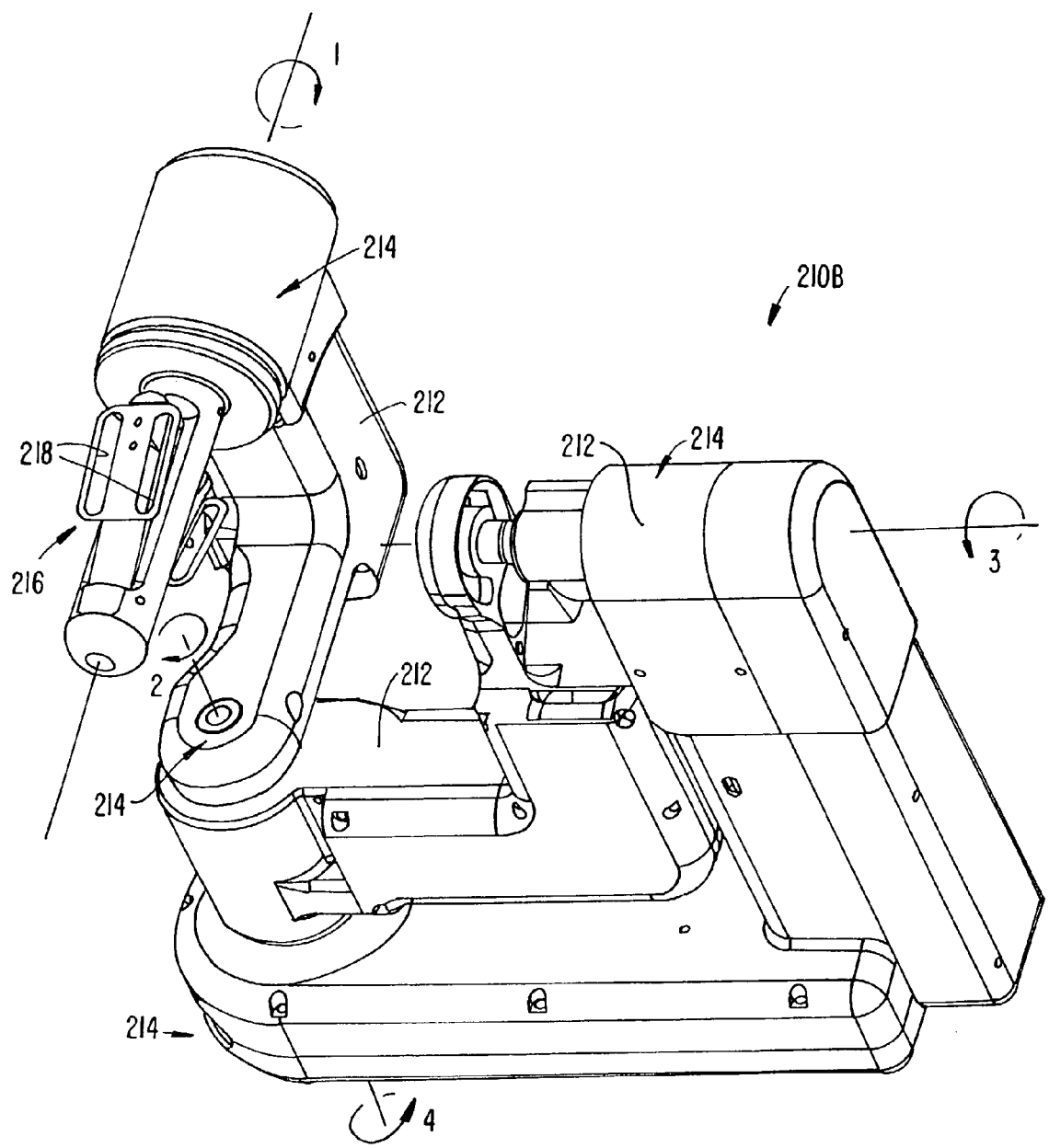
Figure 3C:
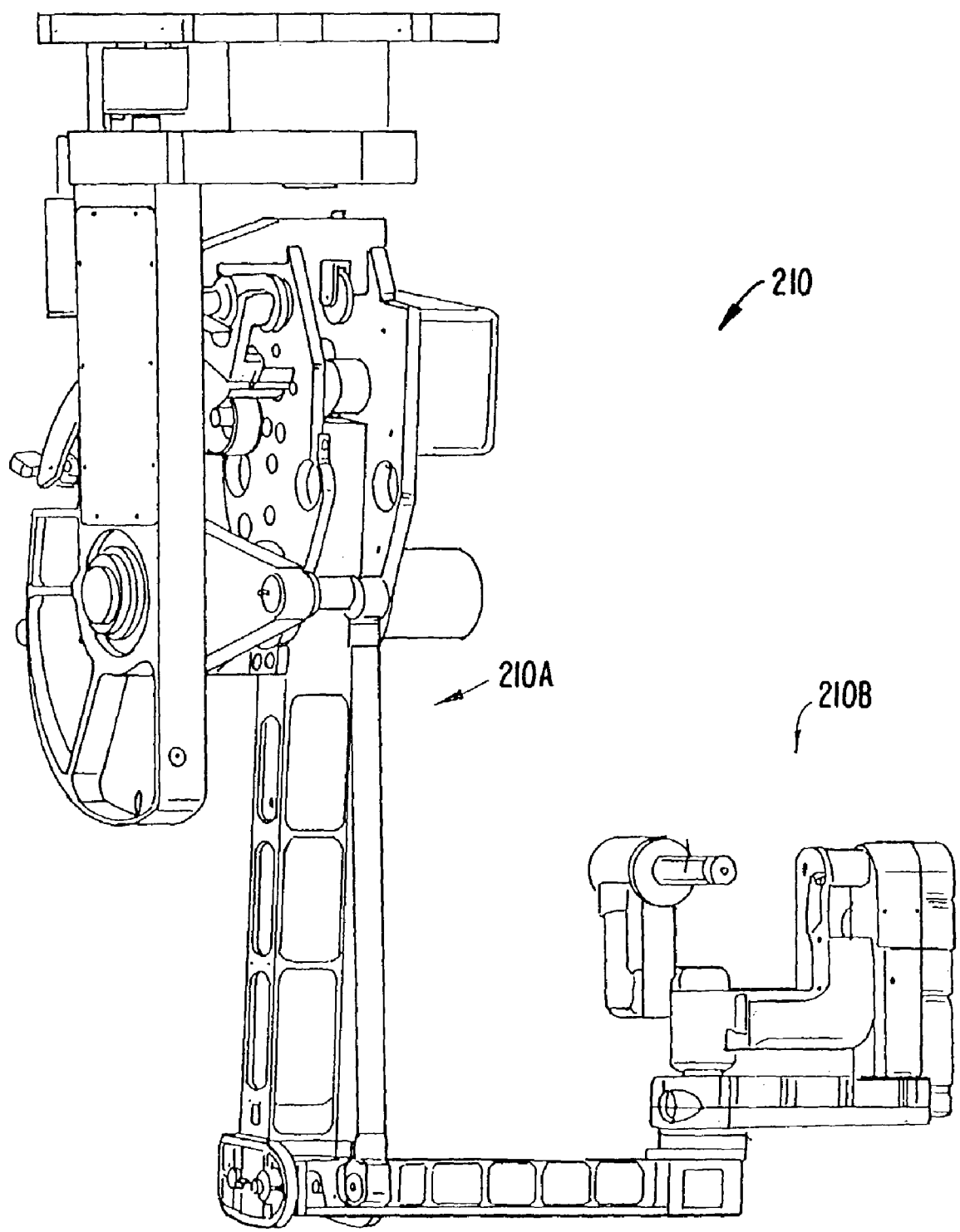

An example of one of the master control input devices is shown in FIGS. 3A-C, and is generally indicated by reference numeral 210. The master control device generally comprises an articulate positioning arm 210A supporting orientational gimbals 210B. Gimbals 210B (shown most clearly in FIG. 3B) have a plurality of members or links 212 connected together by joints 214, typically by rotational joints. The surgeon grips the master control 210 by positioning his or her thumb and index finger over a grip actuation handle, here in the form of a grip handle or pincher formation 216. The surgeon's thumb and index finger are typically held on the pincher formation by straps (not shown) threaded through slots 218. To move the orientation of the end effector, the surgeon simply moves the pincher formation 216 to the desired end effector orientation relative to the image viewed at the viewer 202, and the end effector orientation is caused to follow the orientation of the pincher formation. Appropriately positioned positional sensors, e.g., encoders, or potentiometers, or the like, are coupled to each joint of gimbals 210B, so as to enable joint positions of the master control to be determined as also described in greater detail herein below.

Gimbals 210B are similarly repositioned by movement of pincher formation 216, and this positional movement is generally sensed by articulation of input arm 210A as shown in FIG. 3A. Reference numerals 1-3 indicate orientational degrees of freedom of gimbals 210B, while numeral 4 in FIGS. 3A and 3B indicates the joint with which the master control and the articulated arm are connected together. When connected together, the master control 210 can also displace angularly about axis 4.

The articulated arm 210A includes a plurality of links 220 connected together at joints 222. Articulated arm 210A has appropriately positioned electric motors to provide for feedback as described in greater detail below. Furthermore, appropriately positioned positional sensors, e.g., encoders, or potentiometers, or the like, are positioned on the joints 222 so as to enable joint positions of the master control to be determined as further described herein below. Axes A, B, and C indicate the positional degrees of freedom of articulated arm 210A. In general, movement about joints of the master control 210B primarily accommodates and senses orientational movement of the end effector, and movement about the joints of arm 210A primarily accommodates and senses translational movement of the end effector. The master control 210 is described in greater detail in U.S. Provisional patent application Ser. No. 60/111,710, and in U.S. patent application Ser. No. 09/398,507, filed concurrently herewith, the full disclosures of which are incorporated herein by reference.

As described more fully in co-pending U.S. patent application Ser. No. 09/373,678, the full disclosure of which is incorporated herein by reference, the orientation of the viewer relative to the master control input devices will generally be compared with the position and orientation of the end effectors relative to a field of view of the image capture device. The relative locations of the input devices can be derived from knowledge regarding the input device linkage joint configurations (as sensed by the joint sensors), the construction and design of the master controller structure, and in some cases, calibration measurements taken from a specific master control console system after fabrication. Such calibration measurements may be stored in a non-volatile memory of the console.

In FIG. 4 of the drawings, the cart 300 is adapted to be positioned close to a surgical platform in preparation for surgery, and can then be caused to remain stationary until a surgical procedure has been completed. The cart 300 typically has wheels or castors to render it mobile. The control station 200 may optionally be positioned remote from the cart 300, but will often be in or adjacent the operating room. The cart 300 carries three robotic arm assemblies. One of the robotic arm assemblies, indicated by reference numeral 302, is arranged to hold an image capturing device 304, e.g., an endoscope, or the like. Each of the two other arm assemblies 310 is arranged to carry a surgical instrument 100. The robotic arms are supported by positioning linkages 395, which can be manually positioned and then locked in place before (or repositioned during) the procedure.

The positioning linkages or "set-up joints" are described in Provisional Application Ser. No. 60/095,303, the full disclosure of which is incorporated herein by reference. Preferably, the set-up joints include joint sensors which transmit signals to the processor indicating the position of the remote center of rotation. It should be noted that the manipulator arm assemblies need not be supported by a single cart. Some or all of the manipulators may be mounted to a wall or ceiling of an operating room, separate carts, or the like. Regardless of the specific manipulator structures or their mounting arrangement, it is generally preferable to provide information to the processor regarding the location of insertion/pivot points of the surgical instruments into the patient body. The set-up joint linkages need not have joint drive systems but will often include a joint brake system, as they will often hold the manipulators in a fixed position during some or all of a surgical procedure.

The endoscope 304 has a viewing end 306 at a remote end of an elongate shaft. The elongate shaft of endoscope 304 permits it to be inserted into an internal surgical site of a patient's body. The endoscope 304 is operatively connected to the viewer 202 to display an image captured at its viewing end 306 on the viewer 202.

Each robotic arm 302, 310 can be operatively connected to one or more of the master controls 210 so that the movement of instruments mounted on the robotic arms is controlled by manipulation of the master controls. The instruments 100 carried on the robotic arm assemblies 310 have end effectors, generally indicated at 102, which are mounted on wrist members, the wrists in turn being pivotally mounted on distal ends of elongate shafts of the instruments. It will be appreciated that the instruments have elongate shafts to permit them to be inserted into an internal surgical site of a patient's body. Movement of the end effectors relative to the ends of the shafts of the instruments is also controlled by the master controls.

Figure 5:
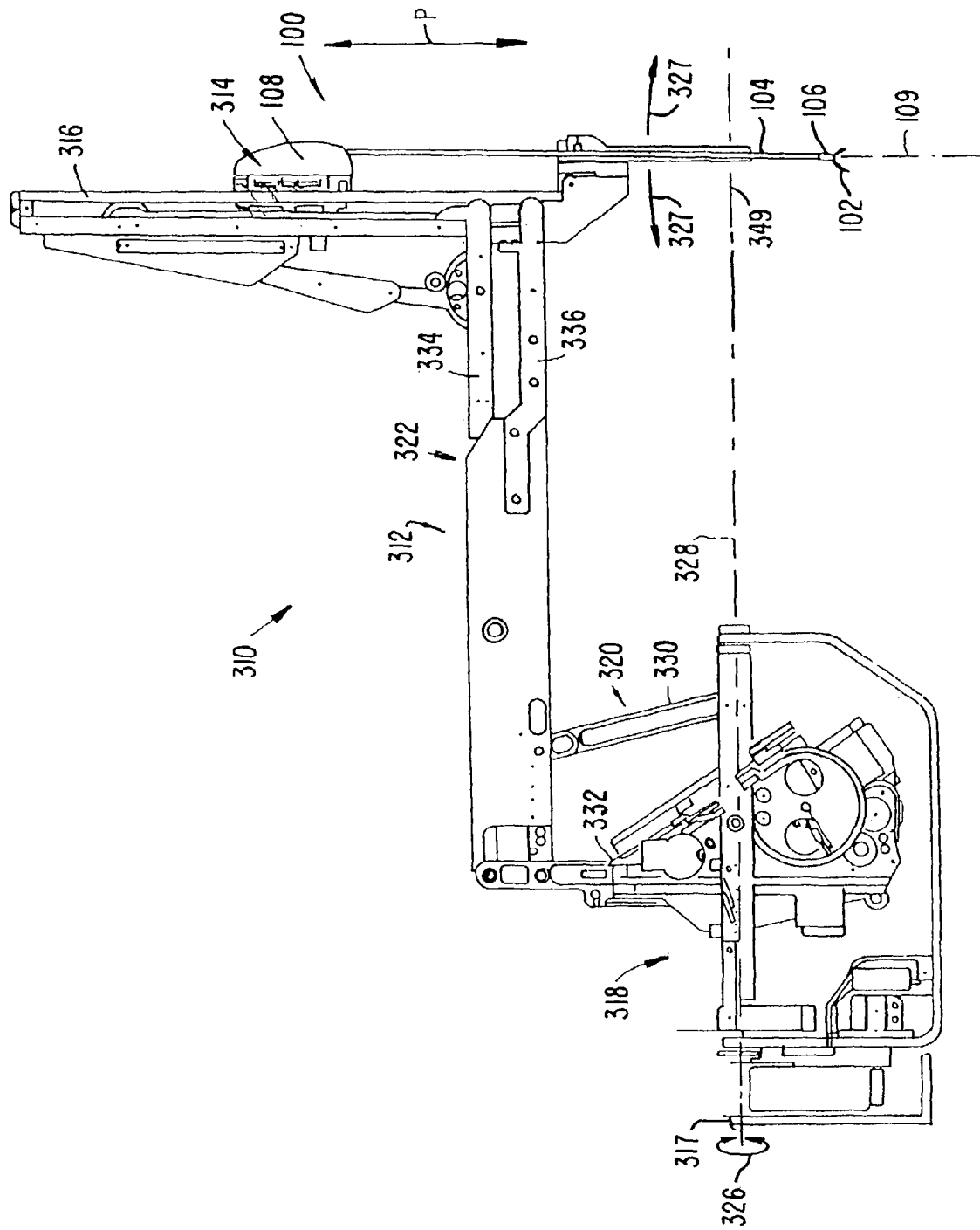
FIGS. 5 and 5A show a side view and a perspective view, respectively, of a robotic arm and surgical instrument assembly in accordance with the invention.
Figure 5A:
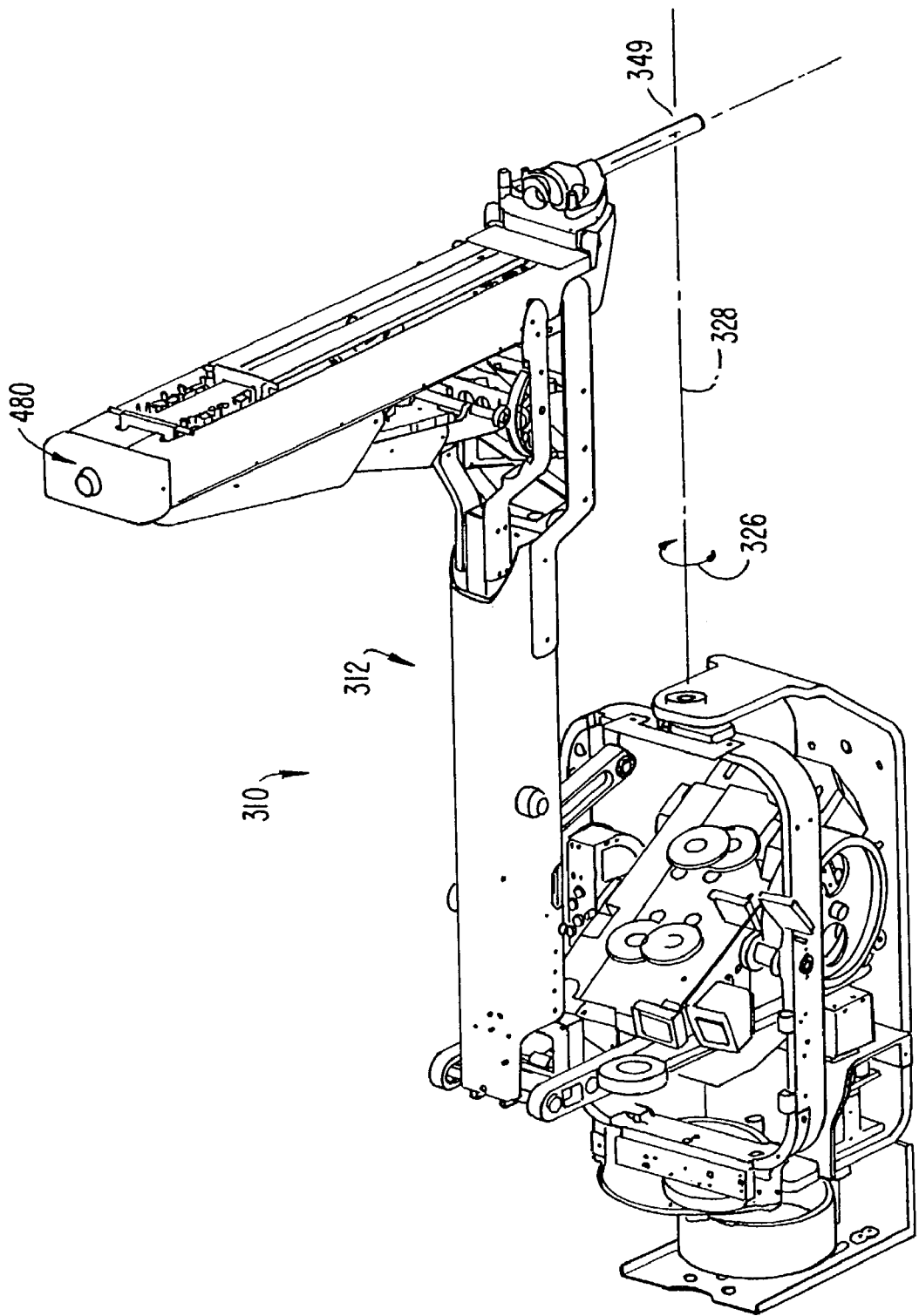

In FIGS. 5 and 5A of the drawings, one of the robotic manipulator arm assemblies 310 is shown in greater detail. Assembly 310 includes an articulated robotic arm 312, and a surgical instrument, schematically and generally indicated by reference numeral 100, mounted thereon.

Figure 6:
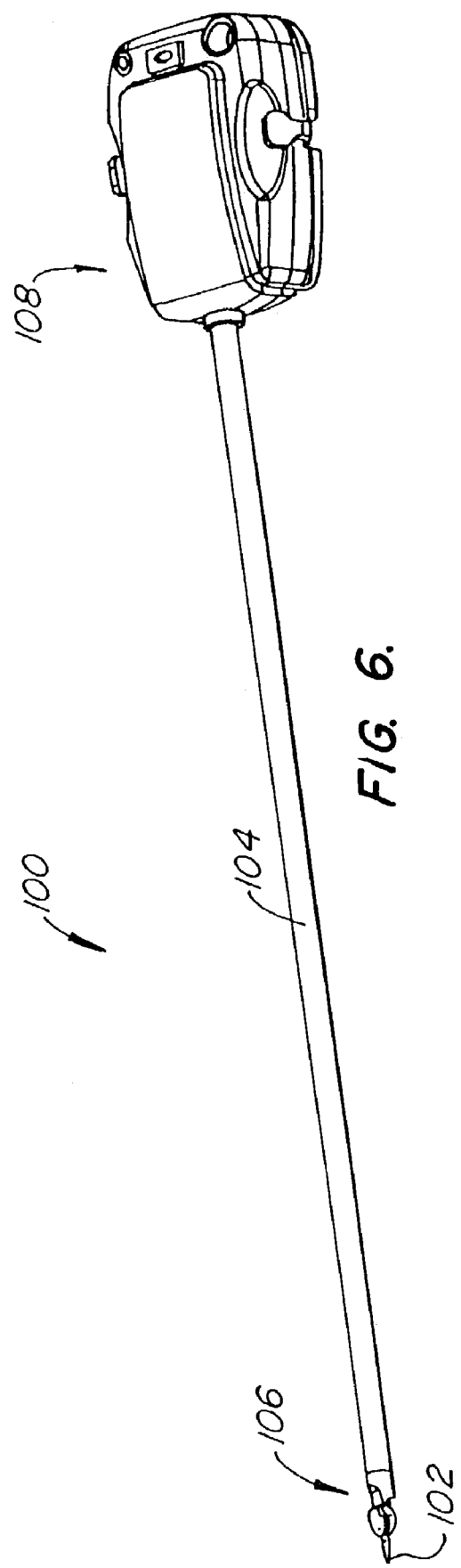
FIG. 6 shows a three-dimensional view of a surgical instrument of the invention.

FIG. 6 indicates the general appearance of the surgical instrument 100 in greater detail. The surgical instrument 100 includes an elongate shaft 104. The wrist-like mechanism, generally indicated by reference numeral 106, is located at a working end of the shaft 104. A housing 108, arranged to releasably couple the instrument 100 to the robotic arm 312, is located at an opposed end of the shaft 104. In FIG. 6, and when the instrument 100 is coupled or mounted on the robotic arm 312, the shaft 104 extends along an axis indicated at 109.

Referring again to FIGS. 5 and 5A, the instrument 100 is typically releasably mounted on a carriage 314, which is driven to translate along a linear guide formation 316 of the arm 312 in the direction of arrows P. The robotic arm 312 is typically mounted on a base by means of a bracket or mounting plate 317, which is affixed to the passively movable set-up joints 395. Set-up joints 395 are held in a fixed configuration during manipulation of tissue by a set-up joint brake system. The base may be defined by the mobile cart or trolley 300, which is retained in a stationary position during a surgical procedure.

The robotic arm 312 includes a cradle, generally indicated at 318, an upper arm portion 320, a forearm portion 322 and the guide formation 316. The cradle 318 is pivotally mounted on the plate 317 in gimbaled fashion to permit rocking movement of the cradle in the direction of arrows 326 as shown in FIG. 5, about a pivot axis 328. The upper arm portion 320 includes link members 330, 332 and the forearm portion 322 includes link members 334, 336. The link members 330, 332 are pivotally mounted on the cradle 318 and are pivotally connected to the link members 334, 336. By use of this linkage, irrespective of the movement of the robotic arm 312, a pivot center 349 remains in the same position relative to plate 317 with which the arm 312 is mounted. In use, the pivot center 349 is positioned at an aperture or a port of entry into a patient's body when an internal surgical procedure is to be performed.

While this "remote" center of motion-type arrangement for robotic manipulation is described in connection with the preferred embodiments of this invention, the scope of the inventions disclosed herein is not so limited, encompassing other types of arrangements such as manipulator arms having passive or natural centers of motion at the point of insertion into a patient body.

The robotic arm 312 provides three degrees of freedom of movement to the surgical instrument 100 when mounted thereon. These degrees of freedom of movement are firstly the gimbaled motion indicated by arrows 326, pivoting movement as indicated by arrows 327 and the linear displacement in the direction of arrows P. These three degrees of freedom of movement are primarily coupled to translational degrees of movement of the end effector, although some rotational coupling may be present. Movement of the arm as indicated by arrows 326, 327 and P is controlled by appropriately positioned electrical motors which respond to inputs from an associated master control to drive the arm 312 to a required position as dictated by movement of the master control. Appropriately positioned sensors, e.g., potentiometers, or the like, are provided on the arm to determine joint positions as described in greater detail herein below.

Figure 7:
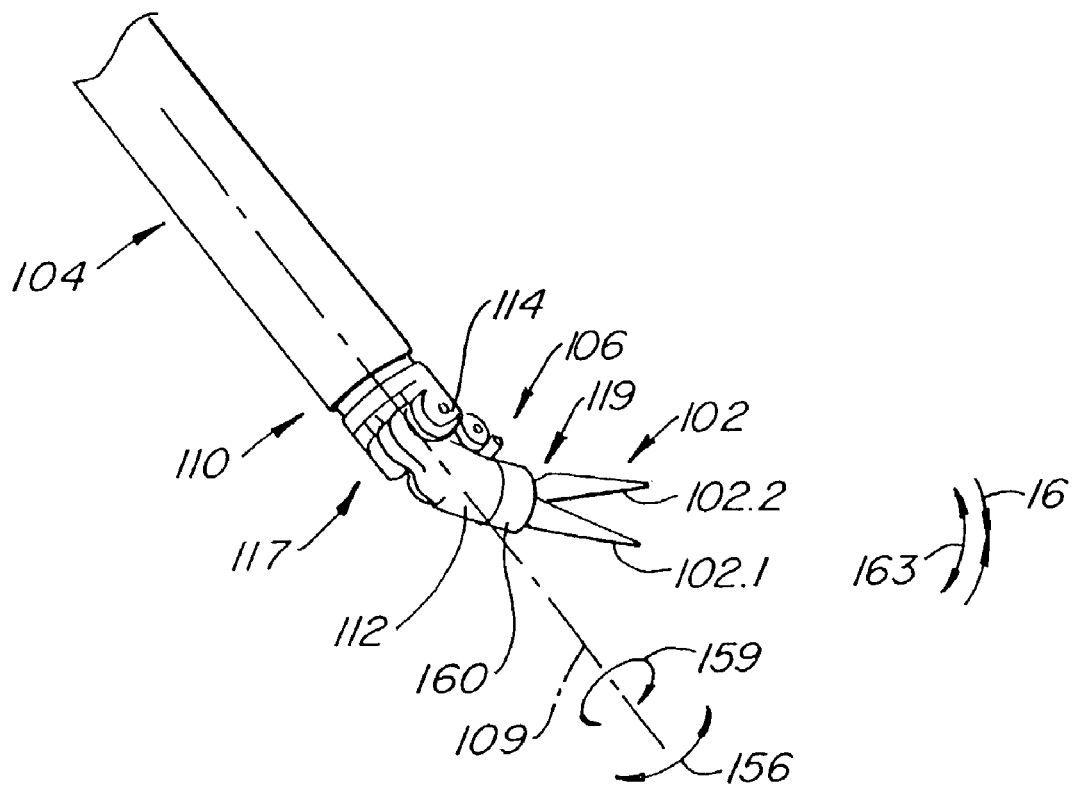
FIG. 7 shows, at an enlarged scale, a wrist member and end effector of the surgical instrument shown in FIG. 6, the wrist member and end effector being movably mounted on a working end of a shaft of the surgical instrument.

Referring now to FIG. 7 of the drawings, the wrist mechanism 106 will now be described in greater detail. In FIG. 7, the working end of the shaft 104 is indicated at 110. The wrist mechanism 106 includes a wrist member 112. One end portion of the wrist member 112 is pivotally mounted in a clevis, generally indicated at 117, on the end 110 of the shaft 104 by means of a pivotal connection 114. The wrist member 112 can pivot in the direction of arrows 156 about the pivotal connection 114.

An end effector, generally indicated by reference numeral 102, is pivotally mounted on an opposed end of the wrist member 127. The end effector 102 is in the form of, e.g., a clip applier for anchoring clips during a surgical procedure. Accordingly, the end effector 102 has two elements 102.1, 102.2 together defining a jaw-like arrangement. It will be appreciated that the end effector can be in the form of any surgical tool having two members which pivot about a common pivotal axis, such as scissors, pliers for use as needle drivers, or the like. Instead, it can include a single working member, e.g., a scalpel, cautery electrode, or the like. Alternative non-articulated tools may also be used, including tools for aspiration and/or irrigation, endoscopes, or the like. When a tool other than a clip applier is required during the surgical procedure, the tool 100 is simply removed from its associated arm and replaced with an instrument bearing the required end effector, e.g., a scissors, or pliers, or the like.

The end effector 102 is pivotally mounted in a clevis, generally indicated by reference numeral 119, on an opposed end of the wrist member 112, by means of a pivotal connection 160. Elements 102.1, 102.2 are angularly displaceable about the pivotal connection 160 toward and away from each other as indicated by arrows 162, 163. It will further be appreciated that the elements 102.1, 102.2 can be displaced angularly about the pivotal connection 160 to change the orientation of the end effector 102 as a whole, relative to the wrist member 112. Thus, each element 102.1, 102.2 is angularly displaceable about the pivotal connection 160 independently of the other, so that the end effector 102, as a whole, is angularly displaceable about the pivotal connection 160 as indicated in dashed lines in FIG. 7. Furthermore, the shaft 104 is rotatably mounted on the housing 108 for rotation as indicated by the arrows 159. Thus, the end effector 102 has three degrees of freedom of movement relative to the arm 112 in addition to actuation of the end effector, preferably namely, rotation about the axis 109 as indicated by arrows 159, angular displacement as a whole about the pivot 160 and angular displacement about the pivot 114 as indicated by arrows 156. Other wrist structures and combinations of joints also fall within the scope of the present inventions, however. For example, while this arrangement and these resulting degrees of freedom of movement are preferred, a wrist having fewer degrees of freedom of movement, such as a single distal articulating joint, or a wrist having other singularities, may also be used, as desired.

The three degrees of freedom of movement of instrument 100 are primarily coupled to orientational degrees of freedom of movement of the end effector. This is somewhat a simplification, as movement about these three axes will result in some change in position of the end effector. Similarly, movement about the above-described translational axes may cause some changes in orientation. It will be appreciated that orientational movement of the end effector, like translational movement, is controlled by appropriately positioned electrical motors which respond to inputs from the associated master control to drive the end effector 102 to a desired position as dictated by movement of the master control. Furthermore, appropriately positioned sensors, e.g., encoders, or potentiometers, or the like, are provided to determine joint positions as described in greater detail herein below. In this specification the actuation or movement of the end effectors relative to each other in the directions of arrows 62, 63 is not regarded as a separate degree of freedom of movement.

Figure 8C:
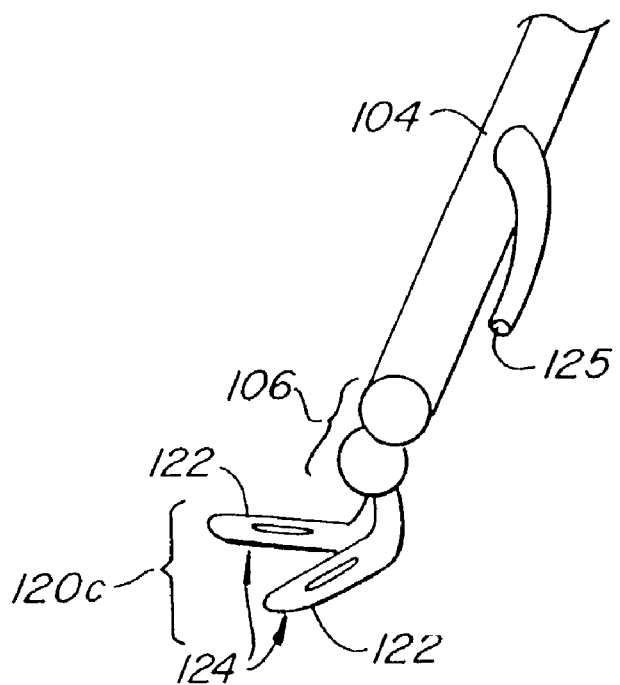
FIGS. 8A-C illustrate alternative end effectors having surfaces for stabilizing and/or retracting tissue.
Figure 8A:
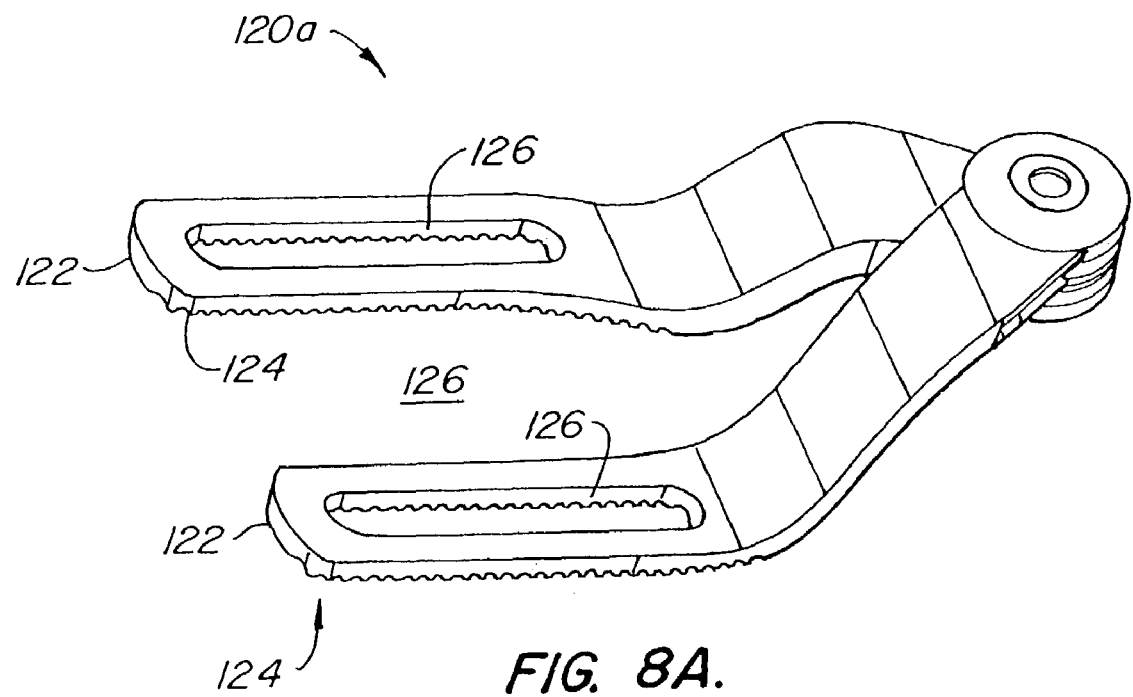
Figure 8B:
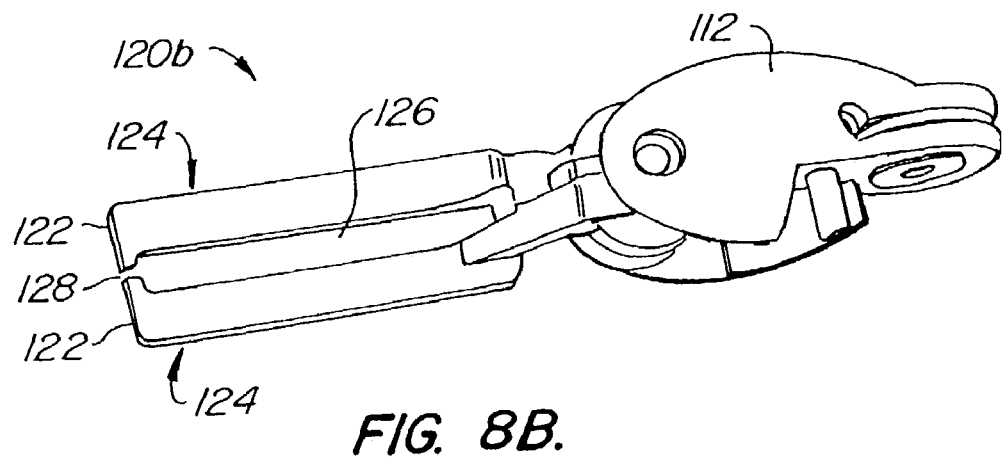

Tissue stabilizer end effectors 120a, b, and c, referred to generally as tissue stabilizers 120, are illustrated in FIGS. 8A-C. Tissue stabilizers 120 may have one or two end effector elements 122 that preferably are pivotally attached to the distal end of the shaft or wrist of a surgical instrument and are moveable with respect to one another, and that preferably comprise tissue-engaging surfaces 124. The tissue-engaging surfaces optionally include protrusions, ridges, vacuum ports, or other surfaces adapted so as to inhibit movement between the engaged tissue and the stabilizer, either through pressure applied to the engaged tissue or vacuum applied to draw the tissue into an at least partially stabilized position, or a combination of both pressure and vacuum. The ideal tissue engaging surface will constrain and/or reduce motion of the engaged tissue in the two lateral (sometimes referred to as the X and Y) axes, along the tissue-engaging surface, and the stabilizer configuration and engagement with the tissue will at least partially decrease motion normal to the surface. Other configurations for traditional stabilizers are known to those of skill in the art, such as the Octopus II of Medtronic, Inc. and various HeartPort, Inc. and CardioThoracic Systems stabilizers having multipronged and doughnut configurations. These manners of contacting tissue allow stabilizers 120 to firmly engage a moving tissue such as a beating heart of a patient and reduce movement of the tissue adjacent the stabilizer.

To facilitate performing a procedure on the stabilized tissue, an opening 126 may be formed in an individual stabilizer element 122, and/or between independently moveable end effector elements. As illustrated in FIG. 8B, stabilizer 120b includes cooperating tissue grasping surfaces 128 disposed between stabilizer end effector elements 122. This allows the stabilizer to grasp tissues, providing a dual function robotic stabilizer/grasper tool. Stabilizer 120b may be used, for example, as a grasper while harvesting and/or preparing an internal mammary artery (IMA) for a coronary artery bypass graft (CABG) procedure, and/or to hold the IMA during formation of the anastomosis on the stabilized beating heart.

In general, tissue stabilizers 120 will have a sufficiently small profile, when aligned with shaft 104 of instrument 100, to allow the stabilizer to advance axially through a cannula. Similar (or modified) end effectors having high friction tissue-engaging surfaces may be used as retractors to hold tissue clear of a surgeon's line of sight during a procedure.

Referring now to FIG. 8C, and generally for the robotic endoscopic stabilizers disclosed herein, each stabilizer may comprise an irrigation port 125, the port preferably in fluid communication with a lumen integrated into the shaft of the stabilizer tool. While an irrigation and/or aspiration capability is particularly beneficial when incorporated into a stabilizer, such capabilities may also be incorporated into the shaft of any robotic surgical tool, as desired. The port system, comprising a lumen preferably situated inside the shaft of the stabilizer and extending out of an aperture or port in the distal portion of the shaft, may be used to perform a number of tasks during a surgical procedure (e.g., a beating heart procedure) in which stabilization of tissue is desired. Those tasks may include removing undesired fluid from the surgical site (either through suction to outside the patient's body), blowing the fluid into some other portion of the surgical site, and/or delivering fluid (such as spray humidified carbon dioxide) to clear the surgical site of material (such as body fluids which might otherwise interfere with the surgeon's view). Preferably, at least the distal portion of the port system is flexible to permit bending. The exemplary port structure will be malleable or plastically deformable enough that it will hold its position when repositioned.

To take advantage of the irrigation aspect of this multi-functional stabilizer, the stabilizer is inserted with the distal external portion of the irrigation device preferably flush with the shaft of the stabilizer. After the stabilizer has reached the surgical site, the operator may reposition the irrigation port distal end with one of the other surgical manipulators by grasping the port structure and moving it to a desired location and/or orientation relative to shaft 104, wrist 106, or end effector element 122 (depending on the structure to which the port is mounted). The device may remain in that location for the duration of the surgery, or may be moved around as desired. In addition to simply being moveable at the surgical site, the device also may be extendable from/retractable into the stabilizer shaft, so that the distal end can be moved towards or away from the surgical site itself, as desired.

Figure 9A:
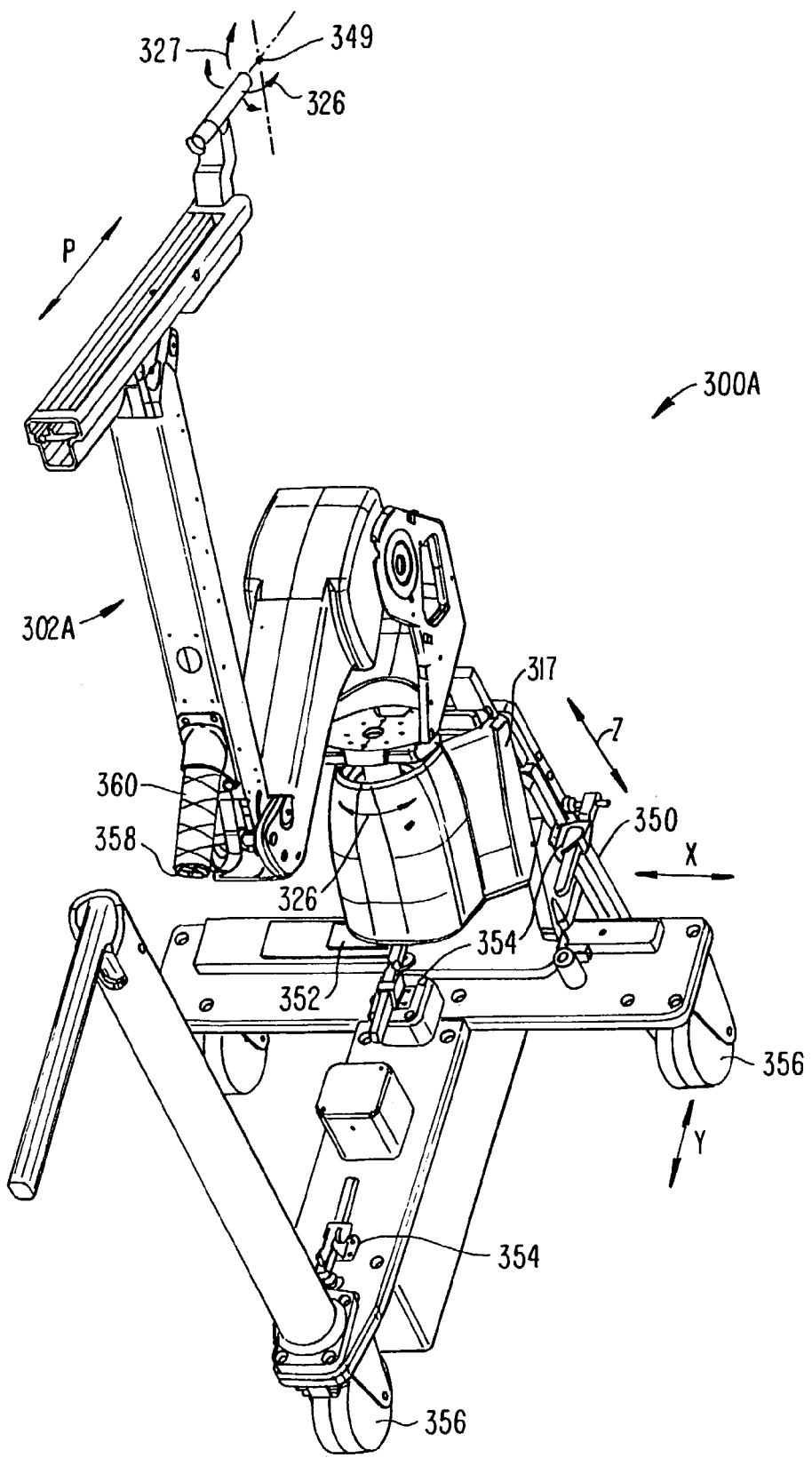
FIGS. 9A-E illustrate another cart supporting a fourth robotic manipulator arm in the telesurgical system of FIG. 1, and a bracket for mounting a tool on the manipulator arm.
Figure 9B:
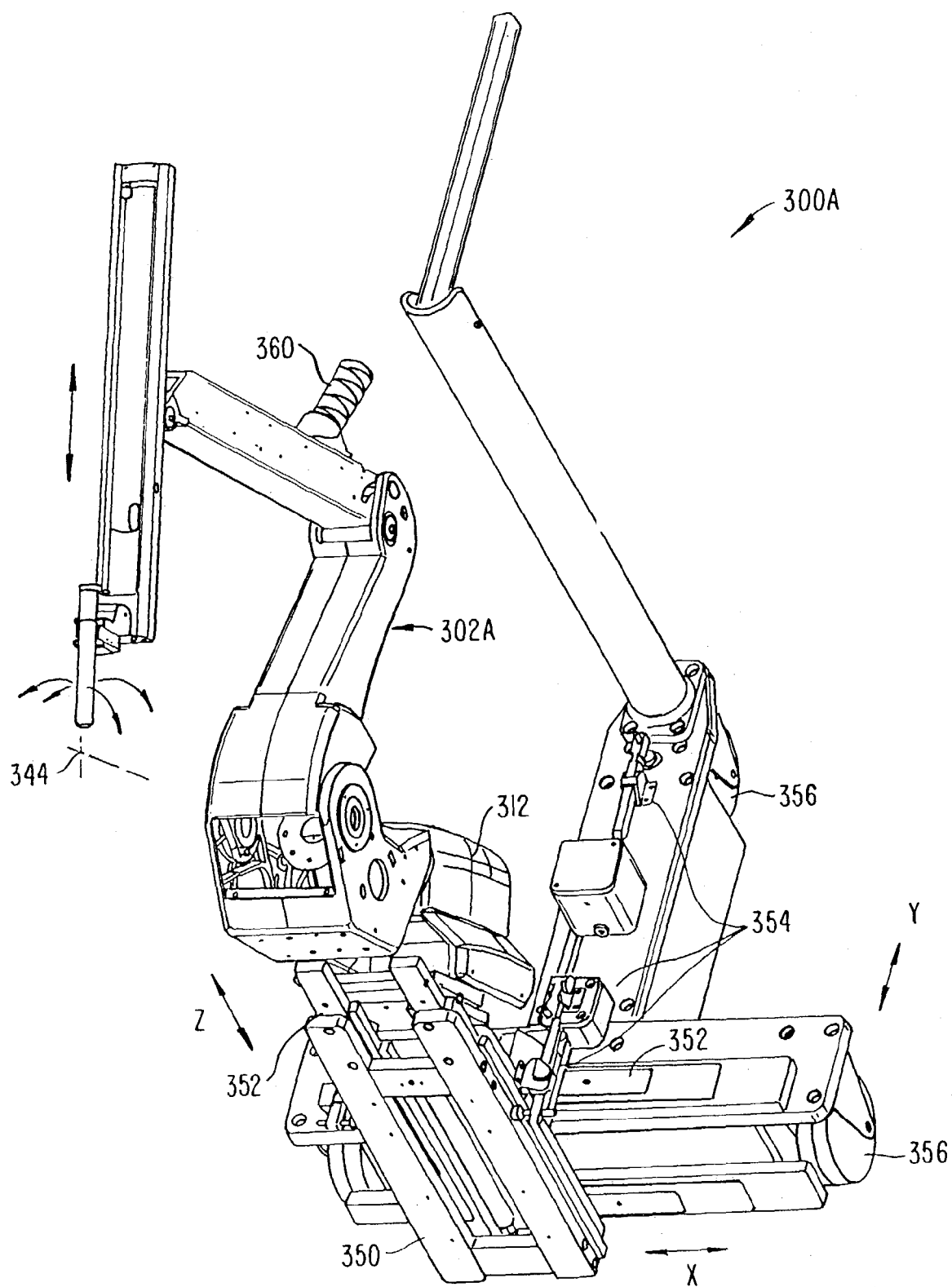

An example of a preferred auxiliary cart 300A is seen in more detail in FIGS. 9A and B. Auxiliary cart 300A includes a simple linkage 350 with sliding joints 352 which can be releasably held in a fixed configuration by latches 354. Linkage 350 supports an auxiliary remote center manipulator arm 302A having a structure similar to arm 302 used to support the endoscope on cart 300. (See FIG. 4.) The linkage structure of auxiliary arm 302A is described more fully in co-pending U.S. Patent Application Ser. No. 60/112,990, filed on Dec. 16, 1998, the full disclosure of which is incorporated herein by reference. Generally, auxiliary arm 302A effectively includes a parallel linkage mechanism providing a remote center of spherical rotation 349 at a fixed location relative to base 317, similar to that described above with reference to arm 312 in FIG. 5. Although this arm is described as preferably being of different structure that other instrument manipulator arms also described herein, it should be understood that a other manipulator arm can also be used either to support an endoscope or to serve as the fourth arm on the auxiliary cart 300A.

Sliding joints 352 and wheels 356 (which can also be releasably locked in a fixed configuration by latches 354) allow remote center or fulcrum 349 to be positioned at an insertion point into a patient body using translational movement along X, Y, and Z axes. Auxiliary arm 302A may optionally be actively driven so as to translationally position a shaft of a surgical instrument within a patient body. Alternatively, auxiliary arm 302A may be used as a passive manipulator arm. Auxiliary arm 302A (like all manipulator arms of the robotic network) preferably includes a repositioning configuration input device or button 358, ideally disposed on a manual positioning handle 360. When repositioning button 358 is depressed, the joints of auxiliary arm 302A move freely so as to pivot the arm about fulcrum 349 manually. Once actuator 358 is released, auxiliary arm 302A remains in a substantially fixed configuration. The arm will resist movement until repositioning button 358 is again held down, or until the arm receives an actuation signal from an associated master control input device. Hence, auxiliary cart 300A may be used to support a surgical instrument such as an endoscope, a stabilizer, a retractor, or the like, even if not actively driven under direction of an input device.

Manual repositioning of the supported surgical instrument will generally be performed by an assistant under the direction of a surgeon in charge of the surgical procedure. Typically, even when the set-up joints 395, cart linkages 350, arms 302, 312, and/or other structures of the robotic system support the end effectors in a fixed configuration, the brake or motor drive systems inhibiting movement of the instruments can be safely overridden using manual force without damaging the robotic system. This allows repositioning and/or removal the instruments if a failure occurs. Preferably, the override force will be sufficient to inhibit inadvertent movement from accidental bumping, interference between manipulators, and the like.

Auxiliary arm 302A and arm 302 used to support endoscope 304 need not necessarily include a drive system for articulating a wrist and/or end effectors within the patient body, unless, e.g., a wrist is to be used in connection with a stabilizer to improve positioning of the particular tissue to be stabilized. When auxiliary cart 300A is to be used to actively drive an articulated tool under the direction of an operator O or assistant via a processor, arm 302 may optionally be replaced by arm 312. Alternatively, where the auxiliary cart is to be used as a passive structure to hold an articulated surgical instrument at a fixed position and configuration within a patient body, a manual tool articulation bracket 370 may be used to mount the tool 100 to auxiliary arm 302A. The manual tool bracket 370 is illustrated in FIGS. 9C-9E.

Figure 9C:
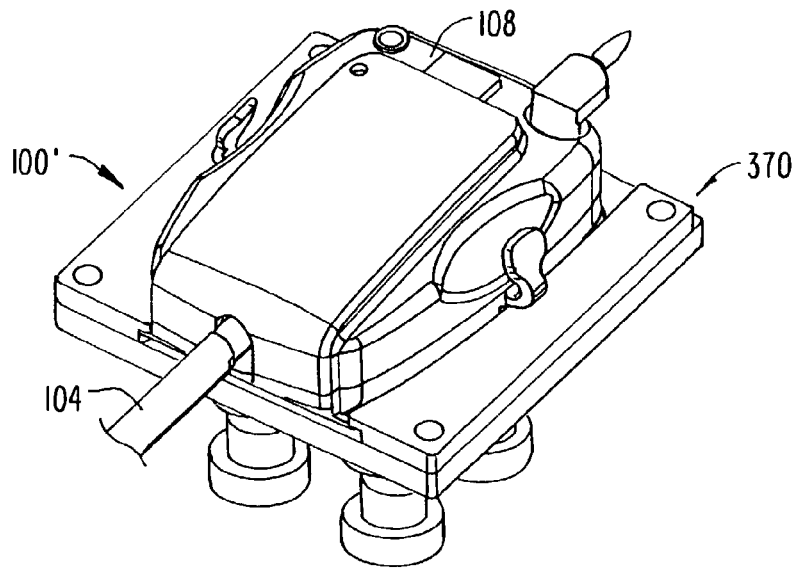
Figure 9D:
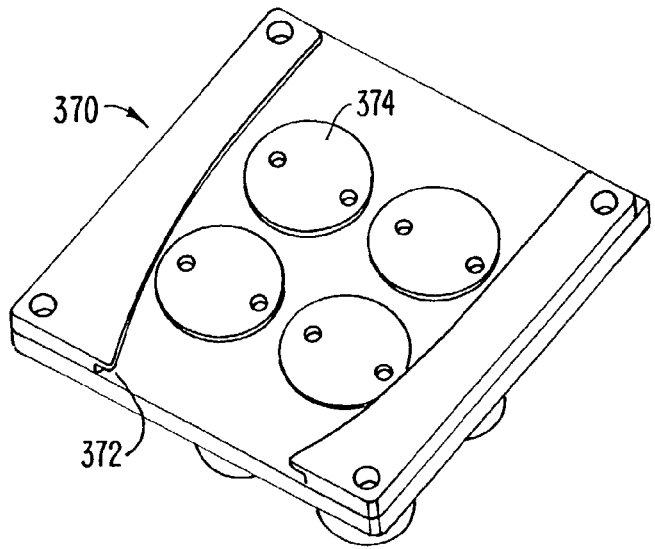

As can be understood with references to FIGS. 9C and 9D, bracket 370 comprises a plate 372 with sidewalls which fittingly receive housing 108 of tool 100. Discs 374 have drive surfaces which drivingly engage the drive system of tool 100 so as to rotate shaft 104 about its axis, articulate the end effector about the wrist, and move the first and second end effector elements, as described above.

Figure 9E:
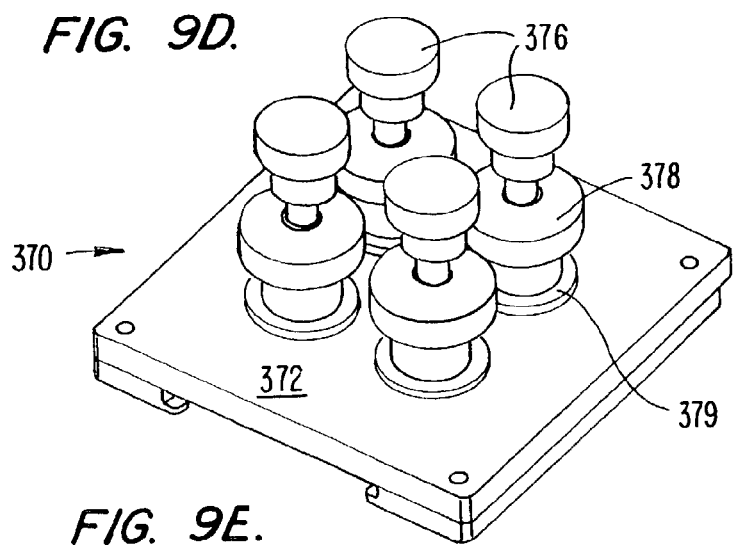

As seen most clearly in FIG. 9E, the rotational position of discs 374 can be changed by manually rotating adjustment knobs 376, which are rotationally coupled to the discs. Once the instrument 100 is in the desired configuration, lock nuts 378 may be tightened against washers 379 to rotationally affix knobs 376 and discs 374. In the exemplary embodiment, bracket 372 comprises a polymer, while knobs 376 and nuts 378 may be polymeric and/or metallic. Washer 379 may comprise a low friction polymer, ideally comprising a PTFE such as Teflon™, or the like. While the disclosure herein shows a preferred embodiment for manual manipulation of a stabilizer by a surgical assistant, it should be apparent that the stabilizer might just as easily be controlled from a remote robotic control console, from which the operator would manipulate the stabilizer and any associated wrist in the same way as other instruments are controlled, as herein described.

Telesurgical Methods and Component Interactions. In use, the surgeon views the surgical site through the viewer 202. The end effector 102 carried on each arm 312, 302, 302A is caused to perform movements and actions in response to movement and action inputs of its associated master control. It will be appreciated that during a surgical procedure images of the end effectors are captured by the endoscope together with the surgical site and are displayed on the viewer so that the surgeon sees the movements and actions of the end effectors as he or she controls such movements and actions by means of the master control devices. The relationship between the end effectors at the surgical site relative to the endoscope tip as viewed through the viewer and the position of the master controls in the hands of the surgeon relative to the surgeon's eyes at the viewer provides an appearance of at least a substantial connection between the master controls and the surgical instrument for the surgeon.

To provide the desired substantial connection between the end effector images and the master controller input devices, the processor of master control station 200 and/or assistant control station 200A will generally map the internal surgical worksite viewed by the endoscope onto the master controller work space in which the operator and/or assistant moves his or her hands. The position of the arms holding the surgical tools relative to the arm holding the endoscope in use may be used to derive the desired coordinate transformations so as to provide the desired level of substantial connectedness, as more fully explained in co-pending U.S. Patent Provisional Application Ser. No. 60/128,160, previously incorporated herein by reference.

Where a tool is to be viewed through an endoscope, and the tool and endoscope are supported by independent support structures (for example, when viewing a tool supported by arm 312 within the internal surgical site via an endoscope supported by auxiliary cart 300A) it is particularly beneficial to have a known orientation between the two independent support structures to allow the desired transformations to be derived. This may be provided, for example, by ensuring that the base structure of cart 300 is accurately parallel to the base structure of auxiliary cart 300A. As positional transformations and modifications are relatively straightforward when orientations are accurately aligned, this allows a processor to provide substantial connection despite the separately mounted robotic network components.

The operation of telesurgical robotic network 10 will first be explained with reference to interaction between master control station 200 and cart 300. Many of the aspects of this interaction appear in the interactions among the remaining network components.

Master-Slave Controller. In FIG. 10, the Cartesian space coordinate system is indicated generally by reference numeral 902. The origin of the system is indicated at 904. The system 902 is shown at a position removed from the endoscope 304. In the minimally invasive telesurgical system of the invention, and for purposes of identifying positions in Cartesian space, the origin 904 is conveniently positioned at the viewing end 306. One of the axes, in this case the Z-Z axis, is coincident with the viewing axis 307 of the endoscope. Accordingly, the X-X and Y-Y axes extend outwardly in directions perpendicular to the viewing axis 307.

It will be appreciated that in the case of angular displacement of the endoscope to vary the orientation of the displayed image as described above, the reference plane defined by the X-X and Y-Y axis is angularly displaced together with the endoscope.

As mentioned earlier, when the surgical instruments are mounted on the arms 112, a fulcrum 349 or pivot point is defined for each arm assembly 310. Furthermore, as also already mentioned, each fulcrum 349 is positioned at a port of entry into the patient's body. Thus, movements of the end effectors at the surgical site is caused by angular displacements about each fulcrum 349. As described above, the location of the fulcrums may be sensed using joint sensors of the set-up joints, or using a variety of alternative position sensing systems.

When the remote center or fulcrum positions relative to the viewing end 306 of the endoscope 304 are determined, the coordinates in the X-X and Y-Y plane of the Cartesian coordinate system 902 are determined. It will be appreciated that these (X,Y) coordinates of each fulcrum 349 can vary depending on the chosen entry ports to the surgical site. The location of these entry ports can vary depending on the surgical procedure to be performed. It will further be appreciated that the (X,Y) coordinates of each fulcrum 349 can readily be determined with reference to the coordinate system 902 by means of the position sensors at the various pivot points on each robotic arm 112 since the endoscope 304 and the arms 310 are mounted on the same cart 300. Naturally, the endoscope arm 302 is also provided with appropriately positioned positional sensors. Thus, to determine the (X,Y) coordinates of each fulcrum 349, relative to the coordinate system 902, the position of the coordinate system 902 can be determined relative to any arbitrary point in space by means of the positional sensors on the endoscope arm 302 and the positions of each fulcrum relative to the same arbitrary point can readily be determined by means of the positional sensors on each robotic arm 112. The positions of each fulcrum 349 relative to the coordinate system 902 can then be determined by means of routine calculation.

Figure 11:
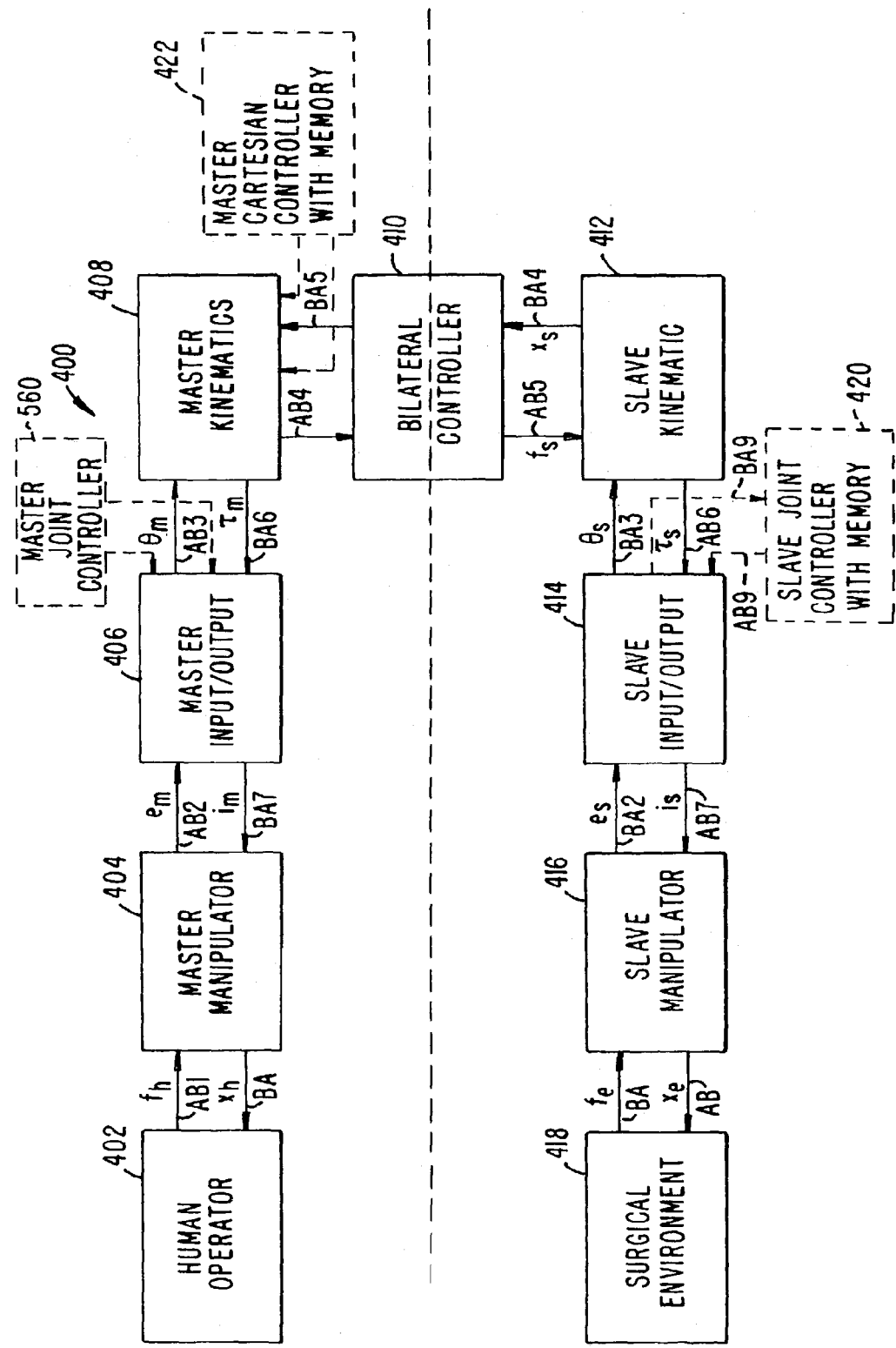
FIG. 11 shows a block diagram indicating one embodiment of a control system of the telesurgical system of the invention.

With reference to FIG. 11, a control system defining a control loop which links master control inputs to end effector outputs, and vice versa for feedback, is schematically indicated by reference numeral 400. Master control inputs and corresponding end effector outputs are indicated by arrows AB and end effector inputs and corresponding master control outputs in the case of feedback is indicated by arrows BA.

In this specification, for the sake of clarity, positions sensed by the encoders on the master which relate to joint positions are referred to as "joint space" positions. Similarly, for the sensors on the joints of the robotic arm and the wrist mechanism, positions determined by these sensors are also referred to as "joint space" positions. The robotic arm and wrist mechanism will be referred to as the slave in the description which follows. Furthermore, references to positions and positioned signals may include orientation, location, and/or their associated signals. Similarly, forces and force signals may generally include both force and torque in their associated signals.

For ease of explanation, the system 400 will be described from an initial condition in which the master is at an initial position and the slave is at a corresponding initial position. However, in use, the slave tracks master position in a continuous manner.

Referring to the control system 400, the master is moved from the initial position to a new position corresponding to a desired position of the end effector as viewed by the surgeon in the image displayed on the viewer 202. Master control movements are input by a surgeon at 402, as indicated by arrow AB1 by applying a force to the master control at 404 to cause the master control to move from its initial position to the new position.

As the master is moved, signals $e_m$ from the encoders on the master is input to a master input controller at 406 as indicated by arrow AB2. At the master input controller 406, the signals $e_m$ are converted to a joint space position $\theta_m$ corresponding to the new position of the master. The joint space position $\theta_m$ is then input to a master kinematics converter 408 as indicated by arrow AB3. At 408 the joint position $\theta_m$ is transformed into an equivalent Cartesian space position $x_m$. This is optionally performed by a kinematic algorithm including a Jacobian transformation matrix, inverse Jacobian ($J^{-1}$), or the like. The equivalent Cartesian space position $x_m$ is then input to a bilateral controller at 410 as indicated by arrow AB4.

Position comparison and force calculation may, in general, be performed using a forward kinematics algorithm which may include a Jacobian matrix. Forward kinematics algorithm generally makes use of a reference location, which is typically selected as the location of the surgeon's eyes. Appropriate calibration or appropriately placed sensors on console 200 can provide this reference information. Additionally, the forward kinematics algorithm will generally make use of information concerning the lengths and angular offsets of the linkage of the master input device 210. More specifically, the Cartesian position $x_m$ represents the distance of the input handle from, and the orientation of the input handle relative to, the location of the surgeon's eyes. Hence, $x_m$ is input into bilateral controller 410 as indicated by AB4.

In a process similar to the calculations described above, the slave location is also generally observed using sensors of the slave system. In the exemplary embodiment, the encoder signal $e_s$ are read from the slave joint sensors at 416 as indicated by BA2, and are then converted to joint space at step 414. As indicated by BA3, the joint space position of the slave is also subjected to a forward kinematics algorithm at step 412. Here, the forward kinematics algorithm is preferably provided with the referenced location of tip 306 of endoscope 304. Additionally, through the use of sensors, design specifications, and/or appropriate calibration, this kinematics algorithm incorporates information regarding the lengths, offsets, angles, etc., describing the linkage structure of patient cart 300, set-up joints 395, and robotic manipulator arms 310, so that the slave Cartesian position $x_s$ transferred at BA4 is measured and/or defined relative to the endoscope tip.

At bilateral controller 410, the new position of the master $x_m$ in Cartesian space relative to the surgeon's eyes is compared with the initial position $x_s$ of the instrument tip in Cartesian space relative to the camera tip. This relationship is depicted in FIG. 10 showing the triangle connecting the surgeon's eye and the master controllers in the hands of the surgeon, as well as the triangle coupling camera tip 306 and the end effectors of tools 104. Advantageously, the comparison of these relative relationships occurring in controller 410 can account for differences in scale between the master controller space in which the input device is moved as compared with the surgical workspace in which the end effectors move. Similarly, the comparison may account for possible fixed offsets, should the initial master and slave positions not correspond.

At 410, the new position $x_m$ of the master in Cartesian space is compared with the initial position of the slave, also in Cartesian space. It will be appreciated that the positions of the master and slave in Cartesian space are continually updated in a memory. Thus, at 410, the initial position of the slave in Cartesian space is downloaded from the memory so as to compare it with the new position of the master in Cartesian space. Thus, the initial position of the slave in Cartesian space was derived from the joint space position of the slave when both the master and the slave were at their initial positions. It will further be appreciated that, at 410, and where the position of the master in Cartesian space conforms with a corresponding position of the slave in Cartesian space, no positional deviation results from the comparison at 410. In such a case no signals are sent from 410 to cause movement of the slave or the master.

Since the master has moved to a new position, a comparison of its corresponding position $x_m$ in Cartesian space with the Cartesian space position of the slave corresponding to its initial position, yields a positional deviation. From this positional deviation in Cartesian space, a force $f_s$ in Cartesian space is computed at 410 which is necessary to move the slave position in Cartesian space to a new position corresponding to the new position of the master $x_m$ in Cartesian space. This computation is typically performed using a proportional integral derivative (P.I.D.) controller. This force $f_s$ is then input to a slave kinematics converter 412 as indicated by arrow AB5. Equivalent joint torques $\tau_s$ are computed in the slave kinematics module, typically using a Jacobian transpose method. This is optionally performed by a Jacobian Transpose ($J^T$) controller.

The torques $\tau_s$ are then input to a slave output converter at 414 as indicated by arrow AB6. At 414 currents is are computed. These currents is are then forwarded to the electrical motors on the slave at 416 as indicated by arrow AB7. The slave is then caused to be driven to the new position $x_e$ which corresponds to the new position into which the master has been moved.

The control steps involved in the control system 400 as explained above are typically carried out at about 1300 cycles per second or faster. It will be appreciated that although reference is made to an initial position and new position of the master, these positions are typically incremental stages of a master control movement. Thus, the slave is continually tracking incremental new positions of the master.

The control system 400 makes provision for force feedback. Thus, should the slave, typically the end effector, be subjected to an environmental force $f_e$ at the surgical site, e.g., in the case where the end effector pushes against tissue, or the like, such a force is fed back to the master control. Accordingly, when the slave is tracking movement of the master as described above and the slave pushes against an object at the surgical site resulting in an equal pushing force against the slave, which urges the slave to move to another position, similar steps as described above take place.

The surgical environment is indicated at 418 in FIG. 11. In the case where an environmental force $f_e$ is applied on the slave, such a force $f_e$ causes displacement of the end effector. This displacement is sensed by the encoders on the slave 416 which generate signals $e_s$. Such signals $e_s$ are input to the slave input converter 414 as indicated by arrow BA2. At the slave input 414 a position $\theta_s$ in joint space is determined resulting from the encoder signals $e_s$. The joint space position $\theta_s$ is then input to the slave kinematics converter at 412 and as indicated by arrow BA3. At 412 a Cartesian space position $x_s$ corresponding to the joint space position $\theta_s$ is computed and input to the bilateral controller at 410 as indicated by arrow BA4. The Cartesian space position $x_s$ is compared with a Cartesian space position $x_m$ of the master and a positional deviation in Cartesian space is computed together with a force $f_m$ required to move the master into a position in Cartesian space which corresponds with the slave position $x_s$ in Cartesian space. The force $f_m$ is then input to the master kinematics converter at 408 as indicated by arrow BA5.

From the $f_m$ input, desired torque values $\tau_m$ are determined at 408. This is typically performed by a Jacobian Transpose ($J^T$) controller. The torque values are then input to the master output converter at 406 as indicated by arrow BA6. At 406, master electric motor currents $i_m$ are determined from the torque values $\tau_m$ and are forwarded to the master at 404 and as indicated by arrow BA7 to cause the motors to drive the master to a position corresponding to the slave position.

Although the feedback has been described with respect to a new position desired by the master to track the slave, it will be appreciated that the surgeon is gripping the master so that the master does not necessarily move. The surgeon however feels a force resulting from feedback Torques on the master which he counters because he is holding onto the master.

The discussion above relating to the control system 400 provides a brief explanation of one type of control system which can be employed. It will be appreciated that instead of using a Jacobian Transpose controller, an Inverse Jacobian Controller arrangement can be used. When using an inversed Jacobian controller, bilateral controller 410 may output a Cartesian slave position command $x_{sd}$ at AB5 to the kinematics module 412, with the Cartesian slave position command indicating the desired position of the slave. Kinematics algorithm module 412 may then use, for example, an inverse Jacobian algorithm to determine a desired joint space position $\theta_{sd}$ which can be compared against the initial joint space position of the slave $\theta_s$. From this comparison, joint torques may be generated to compensate for any positioning errors, with the joint torques passed via AB6 to the slave input/output module 414 as described above.

It should also be noted that control system 400 may couple actuation of the master handle (in the exemplary embodiment, variation of the gripping angle defined between grip members 218 as shown in FIG. 3B) to articulation of the end effector (in the exemplary embodiment, opening and closing the end effector jaws by varying the end effector angle between end effector elements 102.1, 102.2 as illustrated in FIG. 7) in the matter described above, by including the master grip input and the end effector jaw actuation in the joint and Cartesian position effectors, equivalent torque vectors, and the like, in the calculations which have been described.

It should be understood that additional controllers or controller modules may be active, for example, to provide friction compensation, gravity compensation, active driving of redundant joint linkage systems so as to avoid singularities, and the like. These additional controllers may apply currents to the joint drive systems of the master and slaves. The additional functions of these added controllers may remain even when the master/slave control loop is interrupted, so that termination of the master/slave relationship does not necessarily mean that no torques are applied.

An exemplary controller block diagram and data flow to flexibly couple pairs of master controllers with manipulator arms are shown in FIGS. 11A-11D. As described above, the operator 402 manipulates manipulators 404, here inputting actuation forces against both the left and right master manipulators $f_h$(L, R). Similarly, both left and right positions of the master input devices will also be accommodated by the control system, as will forces and positions of four or more slave manipulator arms $f_e$(1, 2, 3, and 4), $x_e$(1, 2, 3, and 4). Similar left, right, and slave notations apply throughout FIGS. 11A-11D.

Figure 11A:
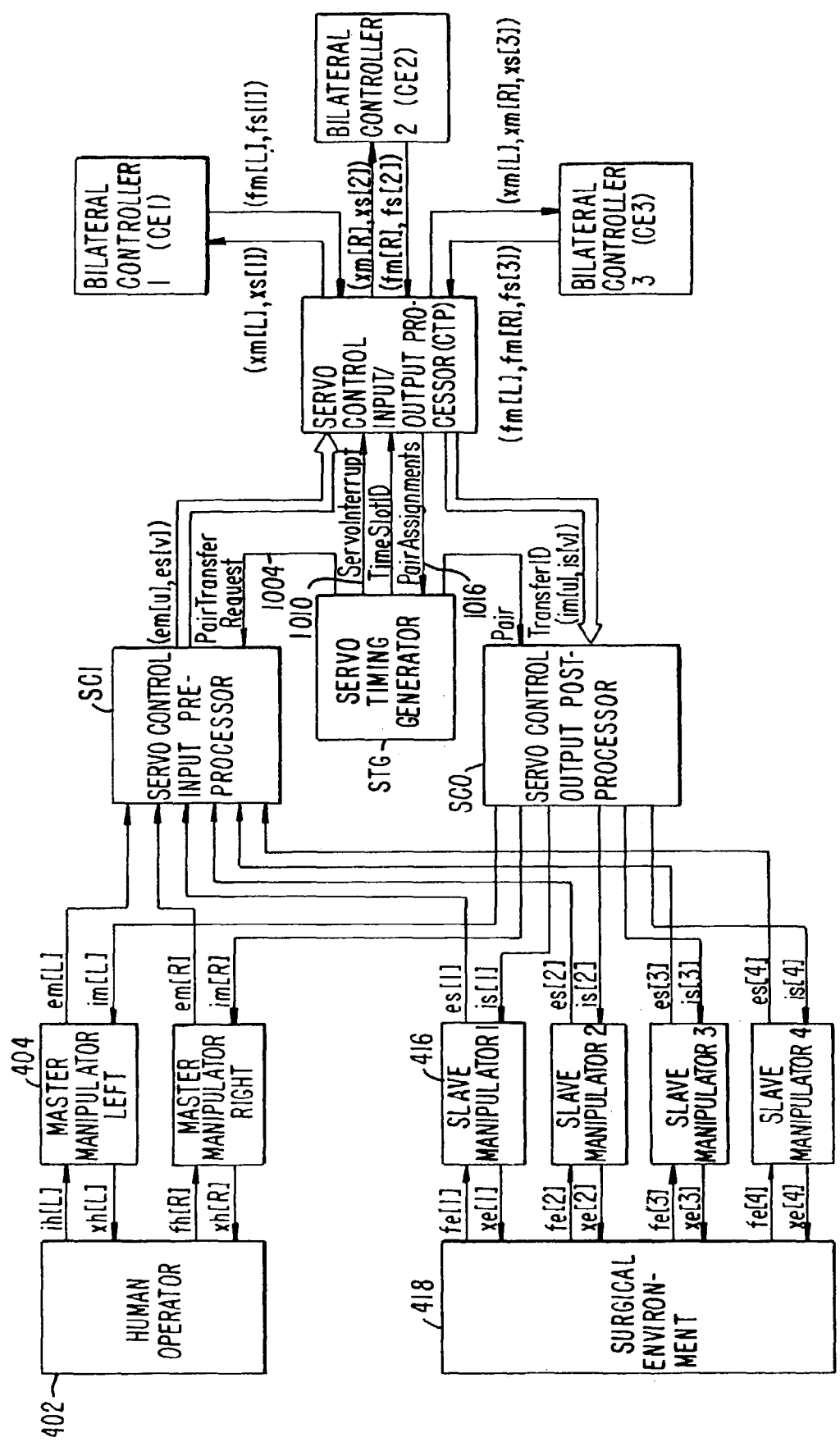
FIGS. 11A-D schematically illustrate block diagrams and data transmission time lines of an exemplary controller for flexibly coupling master/slave pairs.
Figure 11B:
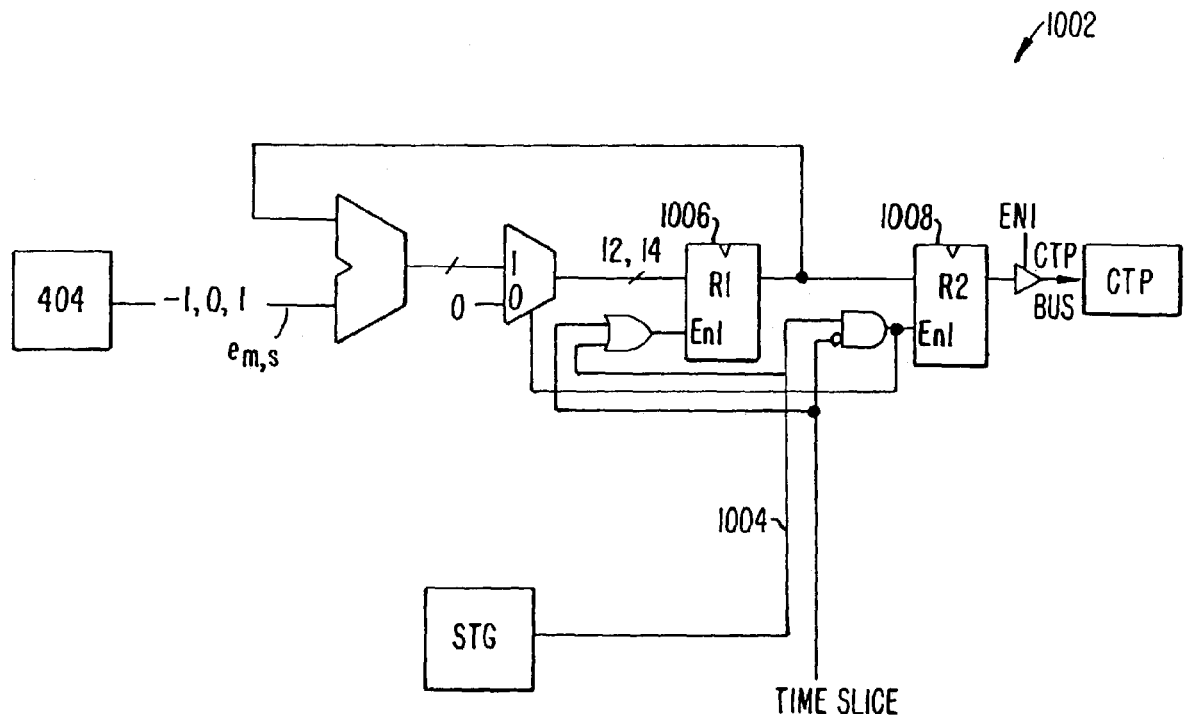

The encoder increments from each joint of the master input devices 404 and the slave manipulators 416 are all input into a servocontrol input pre-processor SCI. In some or all of the joints of the master or slave structures, this information may be provided in an alternative format, such as with an analogue signal (optionally providing absolute position indication) from a Hall effect transducer, a potentiometer, or the like.

Where at least some of the signals transmitted from master input devices 404 or slave manipulators 416 comprise encoder increments, pre-processor SCI may include one or more accumulators 1002 as illustrated in FIG. 11B. Positive and/or negative encoder increments are counted between servocycle transfer requests 1004, which are provided from a servo timing generator STG are accumulated in a first register 1006. After receipt of transfer request 1004, the accumulated encoder increments from throughout the servocycle are transferred to second register 1008.

Figure 11C:
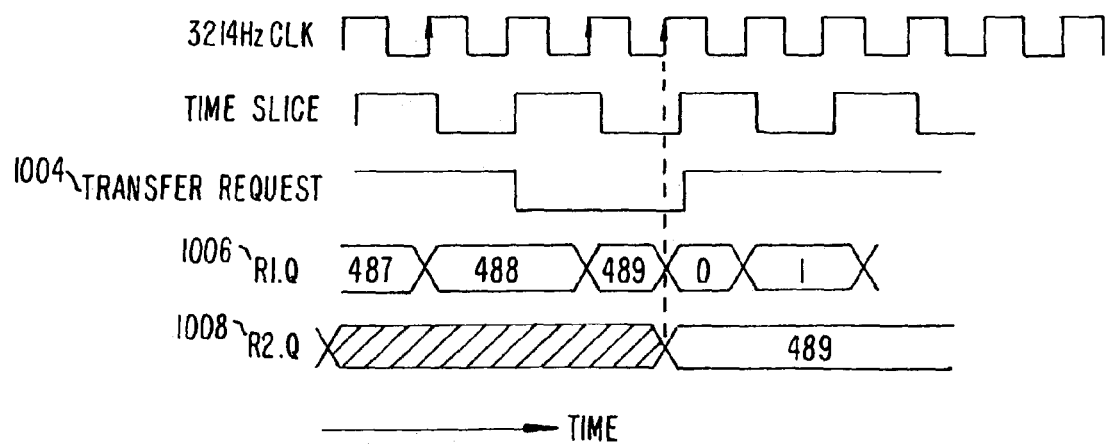

As schematically illustrated in FIG. 11C, the transfer request is preferably offset from an encoder increment clock so as to avoid inadvertent encoder reading errors during servocycle data transfer. In other words, to avoid losing encoder increments during data transfer, an asynchronous transfer request/encoder increment sample rate is preferably provided, as illustrated in FIG. 11C. The sample rate will often be higher than the rate at which the encoder can produce increments, and the accumulators will generally hold incremental position information for all encoder-equipped freely moveable joints of the input and slave manipulators over a servocycle, the servocycle preferably having a frequency of over 900 Hz, more preferably having a frequency of 1,000 Hz or more, often having a frequency of at least about 1,200 Hz, and ideally having a frequency of about 1,300 Hz or more.

Preferably, an accumulator 1002 will be included in pre-processor SCI for each encoder of the master input devices 404 and slave manipulators 416. Each encoder accumulator will preferably accommodate at least a 12-bit joint position signal, and in many cases will accommodate a 14-bit joint position signal. Where analogue position signals are provided, they will typically be converted to digital signals at or before storage in the pre-processor SCI, with as many as 48 joint signals or more being provided in the exemplary pre-processor.

Figure 11D:
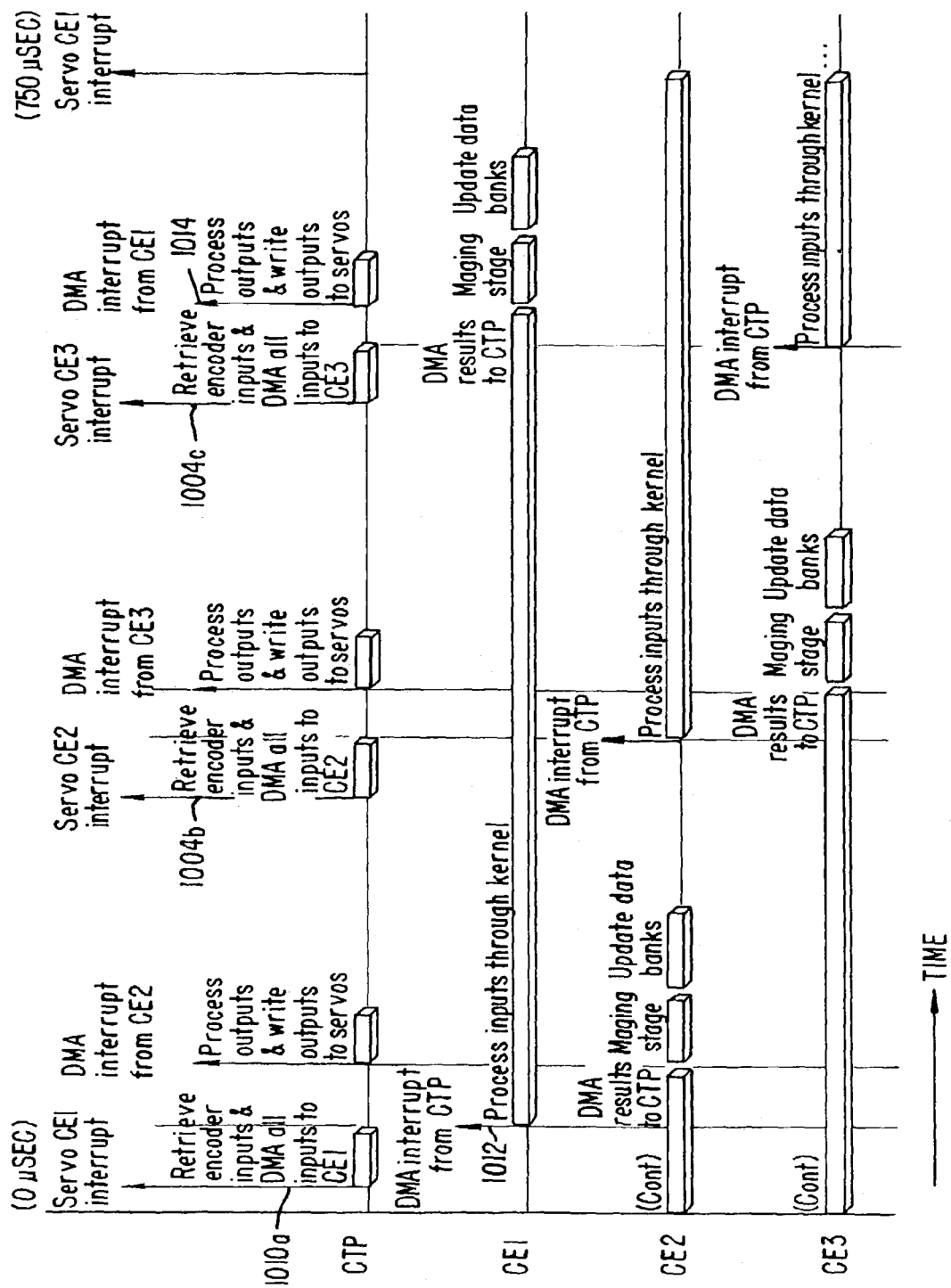

Referring now to FIGS. 11A and 11D, and first concentrating on transmission to and from a first bilateral controller CE1 during a servocycle, joint positional information $e_m$, $e_s$ for a particular master input device 404/slave manipulator 416 pair is retrieved in response to a servointerrupt signal 1010 from the servo timing generator STG. The control processor CTP may transform these joint position signals to the desired coordinate reference frame, or may alternatively transfer this information in joint space on to the bilateral controller CE1 for conversion to the desired reference frame. Regardless, the position is preferably transmitted from the control processor CTP to the bilateral controller CE1 using a direct memory access DMA controller or other high-speed data transmission system.

Once the positional information has been transferred from the control processor CTP to controller CE1 at DMA interrupt 1012 (see FIG. 11D), the controller processes the positional information, comparing the end effector positions in the surgical workspace with the input device positions (including both location and orientation) in the master controller workspace.

As more fully explained in co-pending U.S. patent application Ser. No. 09/373,678, filed Aug. 13, 1999, the full disclosure of which is incorporated herein by reference, the surgical and controller se workspaces may be scaled and positioned relative to each other as desired, often using positional information provided by the sensors of the set-up joints, and incorporating calibration and/or assembly information of the master control console so as to identify the location and/or orientation of the master input device relative to the viewer. In general, as the structure supporting the image capture device and end effectors on the slave side are known, and as the location of the viewer relative to the master input device can be calculated from similar knowledge regarding the lengths of the master input lengths, the master controller joint angles, and the like, an appropriate coordination transformation may be derived so as to mathematically couple the master space of the master control workstation and the slave space in the surgical environment. The information on both the master and slave linkages in structure may be based on a model of these linkage and support structures, on design specifications for the linkage and support structures, and/or on measurements of individual linkages, which may be stored in a non-volatile memory of the slave and/or master control, such as by burning calibration information into a memory of the appropriate structure.

As illustrated in FIG. 11D, much of a servocycle time is used by the controller CE1 to calculate appropriate high-level instructions for the master and slave systems. The results of these calculations are transferred to control processor CTP via yet another DMA interrupt 1014. These high-level commands, typically in the form of desired forces to be applied on the master and slave $f_m$, $f_s$ in a suitable reference frame such as a Cartesian coordinate system are converted by the control processor CTP to desired motor current signals, which are directed to the appropriate motors by post-processor SCO.

While the pre- and post-processors, timing generator, control processor, and controllers are illustrated schematically in FIG. 11A as separate blocks, it should be understood that some or all of these functional components may be combined, for example, on a single processor board, or that multiple processor boards may be used with the functions of one or more of these components being separated on to separate processors.

As can be understood with reference to FIGS. 11A and 11D, while the first controller CE1 is processing the position and other information associated with the first master/slave pair, the pre- and post-processors and control processor are processing and transferring data for use by the second and third controllers CE2, CE3. Hence, the individual controllers have asynchronous input and output times. It should be understood that more than three controllers may be provided for additional master/slave pairs. In the exemplary embodiment illustrated in FIG. 11A, for example, the first and second controllers CE1 and CE2 might be dedicated to left and right hand inputs from the surgeon, while the third controller CE3 may be used to move the endoscope using the left and/or right input device, or any other desired input system.

In the embodiment of FIG. 11A, servo timing generator STG includes a memory storing the master/slave pair assignments 1016. These pair assignments are communicated to the pre- and post-processors SCI, SCO, so that the information transferred to and from the control processor CTP is appropriate for the controller, and so that the commands from the appropriate controller are properly understood and transmitted to the drive system for the appropriate joints. Reallocation of the master/slave pair assignments is transmitted to the timing generator STG from the control processor CTP, and is then communicated from the timing generator to the pre-and post-processors during an intermittent initialization phase, which may also be used to set up appropriate processor time intervals. Alternatively, the time intervals may be fixed.

As should be understood by those of skill in the art, the flexible master/slave pairing controller of FIG. 11A is still a simplification, and an appropriate controller will include a number of additional systems. For example, it is highly beneficial to include fault-checking software to ensure that all encoders or other joint sensors are read during each servocycle, and that the drive systems of each driven joint of the master and slave are written to during each servocycle. If the fault-check is not successfully completed, the system may be shut down. Similarly, the control system may check for changes in pair assignments, for example, during data transfer to and/or from the camera controller. Similarly, pair assignments may be reviewed during and/or after a tool change, during a left/right tool swap, when handing off tools between two different master controllers, when the system operator requests a transfer, or the like.

It should be noted that the control system of FIGS. 11A-11D may accommodate flexible tool mountings on the various manipulators. As described above, the first and second controllers CE1, CE2 may be used to manipulate tools for treating tissue, while the third controller CE3 is dedicated to tool movements using inputs from both master input devices. In general surgical procedures, it may desirable to remove the endoscope or other image capture device from a particular manipulator and instead mount it on a manipulator which was initially used to support a treatment tool. By appropriate commands sent via the control processor CTP to the servo timing generator STG, the pair assignments for the three controllers may be revised to reflect this change without otherwise altering the system operator's control over the system.

During pair re-assignment, appropriate data sets and/or transformations reflecting the kinematics of the master/slave pairs, the relationship of the image capture device with the end effectors, and the like, may be transmitted to the controller. To facilitate swapping the image capture device from one manipulator to another, it may be beneficial to maintain a common manipulator structure throughout the system, so that each manipulator includes drive motors for articulating tools, endoscope image transfer connectors, and the like. Ideally, mounting of a particular tool on a manipulator will automatically transmit signals identifying the tool to the control system, as described in co-pending U.S. patent application Ser. No. 60/111,719, filed on Dec. 8, 1998, entitled "Surgical Robotic Tools, Data Architecture, and Use." This facilitates changing of tools during a surgical procedure.

A variety of adaptations of the exemplary control system will be obvious to those of skill in the art. For example, while the exemplary embodiment includes a single master bus and a single slave bus, one or both of these individual busses may be replaced with a plurality of busses, or they may be combined into a single bus. Similarly, while the exemplary servocycle time for an individual control pair is preferably about 1,000 msec or less, and ideally about 750 msec or less, the use of higher speed processing equipment may provide servocycle times which are significantly faster.

The master/slave interaction between master control station 200 and cart 300 is generally maintained while the operator O is actively manipulating tissues with surgical instruments associated with his or her left and right hands. During the course of a surgical procedure, this master/slave interaction will be interrupted and/or modified for a variety of reasons. The following sections describes selected interruptions of the master/slave control interaction, and are useful for understanding how similar interruptions and reconfigurations of the telesurgical robotic network may be provided to enhance the capabilities of the overall robotic system. The exemplary interruptions include "clutching" (repositioning of a master control relative to a slave), repositioning of an endoscope, and a left-right tool swap (in which a tool previously associated with a master control input device in a right hand of a surgeon is instead associated with an input device in a left hand of the surgeon, and vice versa.) It should be understood that a variety of additional interruptions may occur, including during removal and replacement of a tool, during manual repositioning of a tool, and the like.

Clutching. In the course of performing a surgical procedure, the surgeon may wish to translationally reposition one or both of the master controls relative to the position or positions of a corresponding end effector or effectors as displayed in the image. The surgeon's dexterity is generally enhanced by maintaining an ergonomic orientational alignment between the input device and the image of the end effector. The surgeon may reposition the master relative to the end effector by simply interrupting the control loop and re-establishing the control loop in the desired position, but this can leave the end effector in an awkward orientation, so that the surgeon repeatedly opens the control loop to reorient the end effectors for each translational repositioning. Advantageously, the ergonomic rotational alignment between input devices and the images of the end effectors can be preserved after the master control or controls have been repositioned by a modified clutching procedure, which will now be described with reference to FIGS. 12 and 13.

Figure 12:
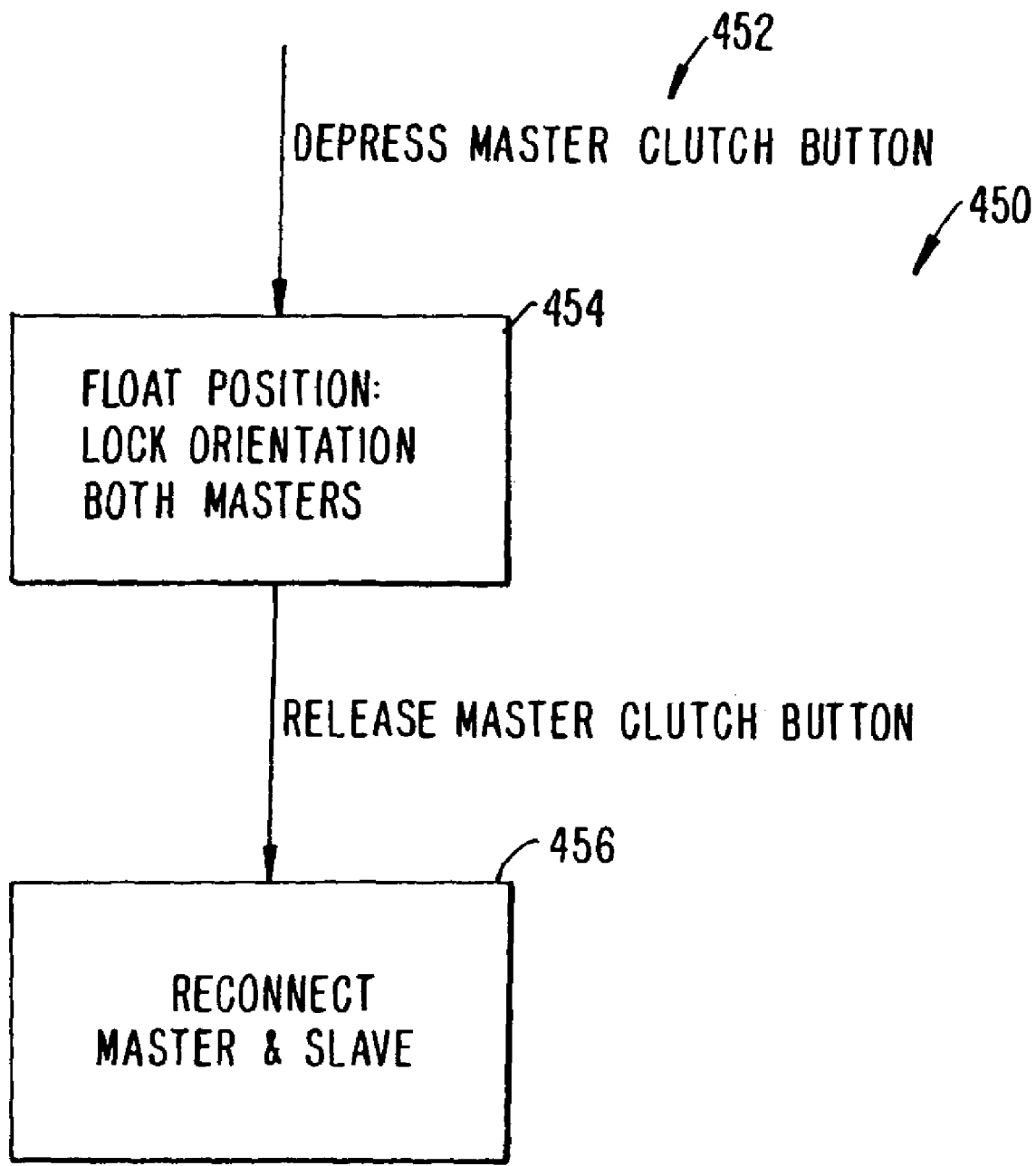
FIG. 12 shows a block diagram indicating the steps involved in moving the position of one of the master controls relative to its associated end effector.
Figure 13:
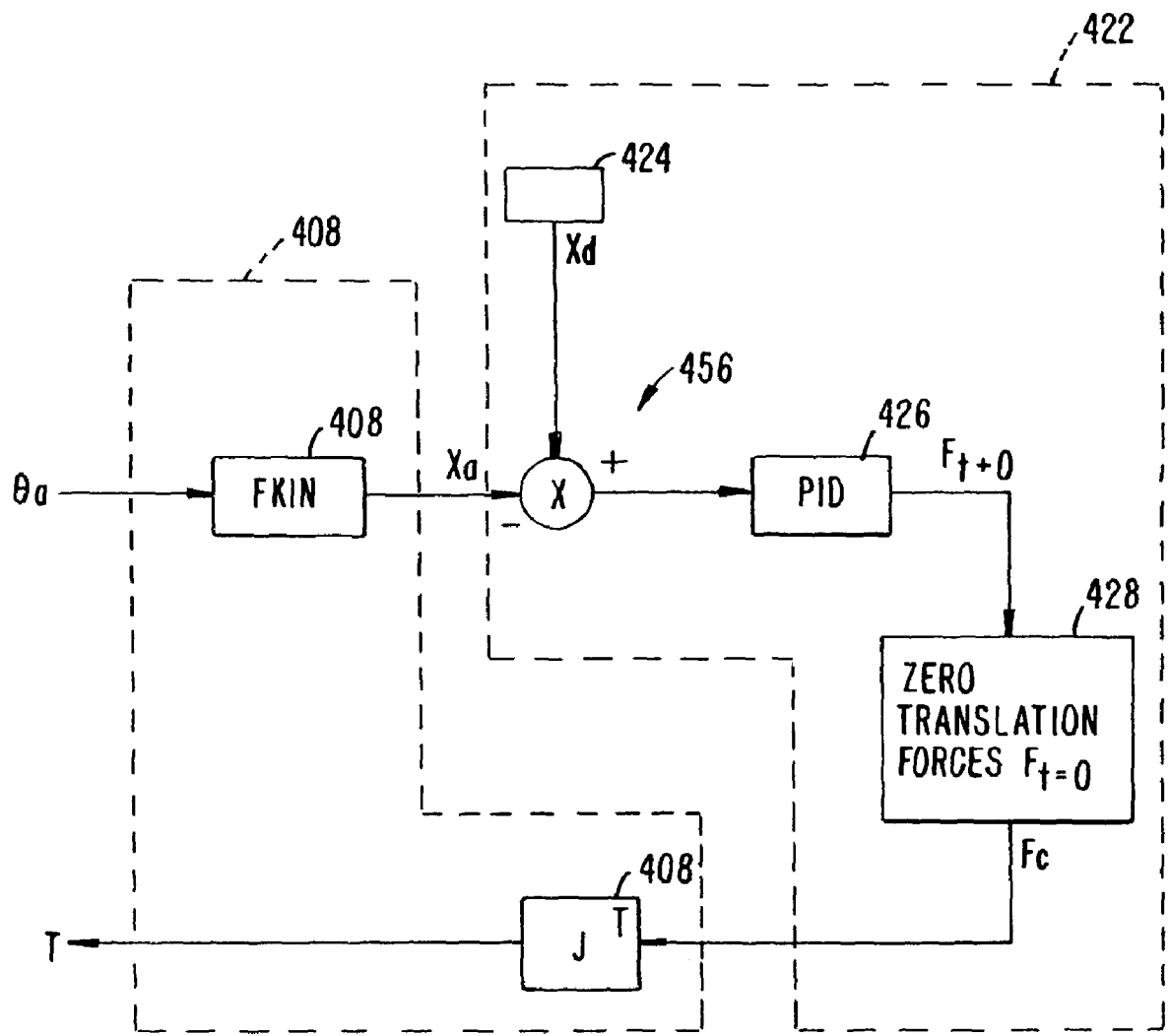
FIG. 13 shows a control diagram which indicates control steps involved when the master control is moved relative to its associated end effector as indicated in the block diagram of FIG. 12.

Referring to FIG. 12, a block diagram indicating the repositioning of one of the master controls is indicated generally by reference numeral 450 and will now be described. It will be appreciated that both master controls can be re-positioned simultaneously. However, for ease of description, the repositioning of a single master control will be described. To reposition the master control relative to its associated slave, the surgeon causes the control loop 400 linking master control movement with corresponding slave movement to be interrupted. This is accomplished by activation by the surgeon of a suitable input device, labeled "Depress Master Clutch Button" at 452 in FIG. 12. It has been found that such a suitable input device can advantageously be in the form of a foot pedal as indicated at 208 in FIG. 2. It will be appreciated that any suitable input can be provided such as voice control input, a finger button, or the like. It is advantageous to provide an input device which does not require the surgeon to remove his or her hands from the master controls so as to preserve continuity of master control operation. Thus, the input device can be incorporated on the master control device itself instead of having a foot pedal.

Once the input has been activated, e.g., by depressing the foot pedal, the control loop 400 between master and slave is interrupted. The slave is then locked in its position, in other words in the position in which it was at immediately before the foot pedal was depressed.

As can be described with reference to FIG. 11, upon depression of the foot pedal, the link 410 in the control system 400 between master and slave is interrupted. The position in joint space of the slave immediately before depression of the foot pedal is recorded in a memory of a slave joint controller indicated at 420 in dashed lines. Should a force then be applied to the slave to cause it to displace to a new joint position, the encoders on the slave relay signals to 414 where a new joint space position for the slave is computed and forwarded to the slave joint controller 420 as indicated by arrow BA9. This new joint space position is compared with the joint space position in the memory, and joint space deviations are determined. From this joint space deviation, torques are computed to return the slave to the joint position as recorded in the memory. These torques are relayed to 414 as indicated by arrow AB9 where corresponding electric motor currents are determined which are forwarded to the slave motors to cause it to restore its joint space position. Thus, the slave position is servo locked.

Referring again to FIG. 11, upon depression of the foot pedal at 452, the translational movement of the master is caused to float while its orientation is locked, as indicated at 454 in FIG. 12. This step is achieved by a master Cartesian controller with memory as indicated at 422 in FIG. 11. The functioning of the master Cartesian controller with memory will now be described with reference to FIG. 13.

Upon activation of the foot pedal and repositioning of the master, the joint space position input of the master control as indicated by $\theta_a$ is converted from joint space to Cartesian space at 406. From this conversion, a Cartesian space position $x_a$ of the master is obtained. The position in Cartesian space of the master immediately before activation of the foot pedal is recorded in a memory at 424 and is indicated by $x_d$. The current position $x_a$ of the master as it moves to its new position is compared with the recorded position $x_d$ at 456 to obtain error signals, which correspond to positional deviations of current master position in Cartesian space when compared with the recorded position $x_d$ in Cartesian space. These deviations or errors are input to a feedback controller at 426 to determine a feedback force to return the master to a position corresponding to the recorded position $x_d$. The components of the feedback force which corresponds to translational movement are zeroed at 428. Thus, translational feedback force components are zeroed and only orientational force components are forwarded from 428. The orientational force components are then converted to corresponding torques at 408, which are then input to 406 (in FIG. 11) to determine currents for feeding to the electric motors on the master to cause its orientation to be urged to remain in a condition corresponding to the orientation determined by $x_d$. It will be appreciated that the orientation at the position $x_d$ corresponds to the orientation of the slave since the slave continuously tracks the master and the positions were recorded in memory at the same time. Since the translational forces were zeroed, the translational movement of the master is caused to float enabling the surgeon to translate the master to a new, desired position. Such translational floating may alternatively be provided by a variety of other methods. For example, the translational gains of controller 426 may be set to zero. In some embodiments, the translational elements of memory 424 may be continually reset to be equal to the input values $x_a$, so that the difference between the measured position and the stored position is zero. It should also be understood that despite the zeroing of the translational terms, additional controller functions such as friction compensation, gravity compensation, or the like, may remain unaltered.

Referring again to FIG. 12 of the drawings, when the master controls have been moved to their desired position the foot pedal is released. Upon release, the translational deviations relating to the new position of the master control relative to its associated slave is incorporated into 410 to define a new Cartesian space position at which the slave position corresponds to the master position. In particular, the translational derivations may be incorporated in the fixed offsets described above, preferably using the algorithm described herein to avoid inadvertent sudden movements or forces.

Since the orientation of the end effector was held at the same position, and since the master orientation was caused to remain in a corresponding orientation, realignment of the end effector and master is normally not necessary. Re-connection of master and slave takes place upon release of the foot pedal as indicated at 456. The re-connection will now be described with reference to FIG. 19.

Figure 19:
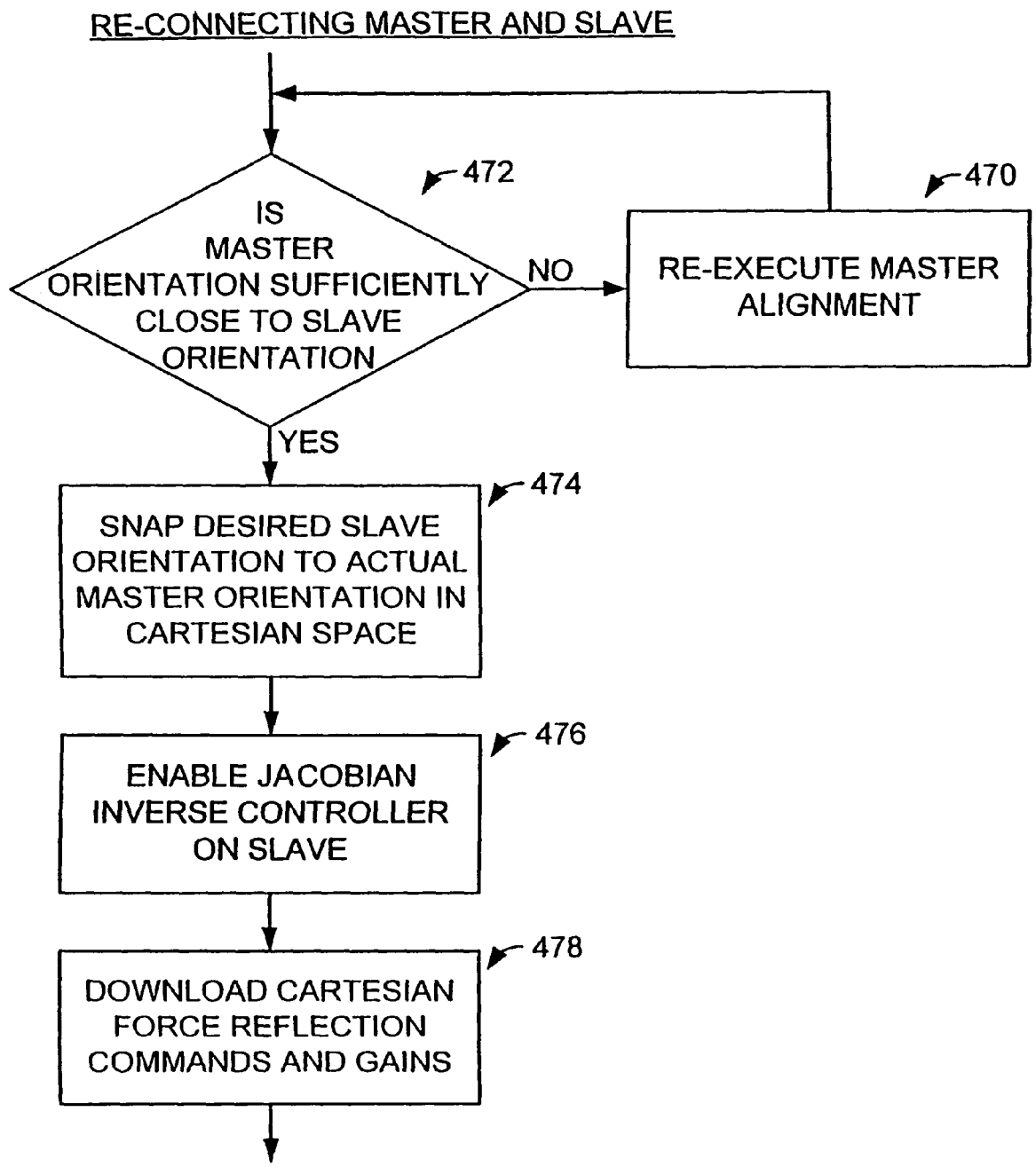
FIG. 19 shows a block diagram indicating the steps involved in re-connecting a control loop between a master control device and its associated end effector.

Referring to FIG. 19, a block diagram illustrating the steps involved in re-connecting the control system 400 between the master and the slave is generally indicated by reference numeral 470.

The first step involving in re-connecting control between the master and the slave, and as indicated at 472, is to determine whether or not the master orientation is sufficiently close to the slave orientation. It will be appreciated that it could happen that during repositioning of the master as described above, the surgeon could be urging the pincher formation on the master away from its orientationally aligned position relative to the slave. Should re-connection of control between master and slave then occur, it could result in reactive motion by the slave resulting from the urging force applied by the surgeon on the pincher formation. This reactive motion by the slave could cause unnecessary damage to organs, or tissue, or the like, at the surgical site and should be avoided. Accordingly, at 472 the orientation of master and slave is compared. If the orientation of the master does not coincide with the orientation of the slave or does not fall within an acceptable orientational deviation, re-connection of control between master and slave will not be enabled. In such a case an appropriate message is typically displayed on the viewer indicating to the surgeon that a required corrective action is required to cause the orientation of the master to be within the acceptable deviational range relative to the orientation of the slave. An example of such a message is one indicating to the surgeon to relax his or her grip on the pincher formation. Simultaneously, the master alignment algorithm may be executed as described hereinbelow with reference to FIG. 18.

When the orientations of master and slave are sufficiently similar, the slave orientation is optionally snapped with the master orientation in Cartesian space as indicated at 474. Once the orientation is snapped, the Jacobian Inverse controller on the slave is enabled as indicated at 476. Thereafter, the Cartesian force reflection commands and gains are downloaded as indicated at 478.

As used herein, the snapping of the slave orientation to the master orientation means that the orientational offsets in bilateral controller 410 are reset to zero, so that the master and slave orientations begin tracking each other. In synchronization with this snapping, the control system 410 is reconfigured to normal bilateral control, preferably using a Jacobian inverse, as indicated at step 476. The appropriate commands and gains are downloaded as indicated at step 478.

In many embodiments, rather than instantaneously snapping the master to the slave, the orientational offsets in bilateral controller 410 may alternatively be slowly and smoothly reduced to zero, thereby providing a smoother transition between operating modes. This may be effected by, for example, filtering the orientational offset values to zero.

In general, some and/or all transition of control system 400 between operating configurations or modes, including those described with reference to steps 454 and 456 of the master repositioning algorithm of FIG. 12, as well as a variety of similar steps described hereinbelow, may include potentially substantially instantaneous changes in configuration or perimetric values of the control system. For example, interrupting or opening the loop of bilateral controller 410, enabling master Cartesian controller 422, resetting memory 424 or the controller gains in P.I.D. controller 426 might be performed by substantially instantaneously changing the perimetric values and/or configurations. Such instantaneous changes may be fundamentally different than normal master/slave operation, where the computations are continually repeated using fixed perimetric values and operational configurations, with only the sensor readings changing.

Where substantially instantaneous changes in perimetric values and/or configuration are imposed, it is possible that a sudden change in motor currents may result, causing the system to jerk. Such inadvertent instantaneous movements of the system may be transmitted to the surgeon or other system operator, and can be disconcerting and/or reduce the overall feel of control the operator has over the system. Additionally, unexpected rapid movements of a surgical instrument at a surgical site are preferably minimized and/or avoided. Hence, rather than effecting these changes in perimetric values and/or configuration instantaneously, the changes will preferably be timed and executed in a manner so as to avoid significant instantaneous changes in the computed motor currents applied before, during, and after the change in configuration. This smooth change of perimetric values and/or controller configurations may be provided by a "no-jerk" algorithm which will be described with reference to FIG. 19A.

The relevant control system mode transitions typically involve a configuration change, a change in a fixed memory value, or the like. In particular, bilateral controller 410 makes use of fixed offsets in its memory. Controllers 420, 422, and 560 also contain fixed commands in their memories. The no-jerk algorithm, which generally decreases and/or eliminates rapid inadvertent movement of the master or slave, utilizes known sensor readings, configuration information, and memory values immediately before a control system operating mode transition. By assuming that sensor readings will remain predictable, changing only slightly during the controller mode transition, the no-jerk algorithm computes desired memory reset values by also taking into account the known end values or configuration, and by synchronizing the change in values so as to promote smooth motor current changes during the mode transition. For some uses, the no-jerk algorithm my reduce or eliminate sudden changes in motor torques by using pre-transition (and optionally filtered) motor currents or joint torque values in place of or in combination with the pre-transition sensor configuration and memory values as inputs.

Figure 19A:
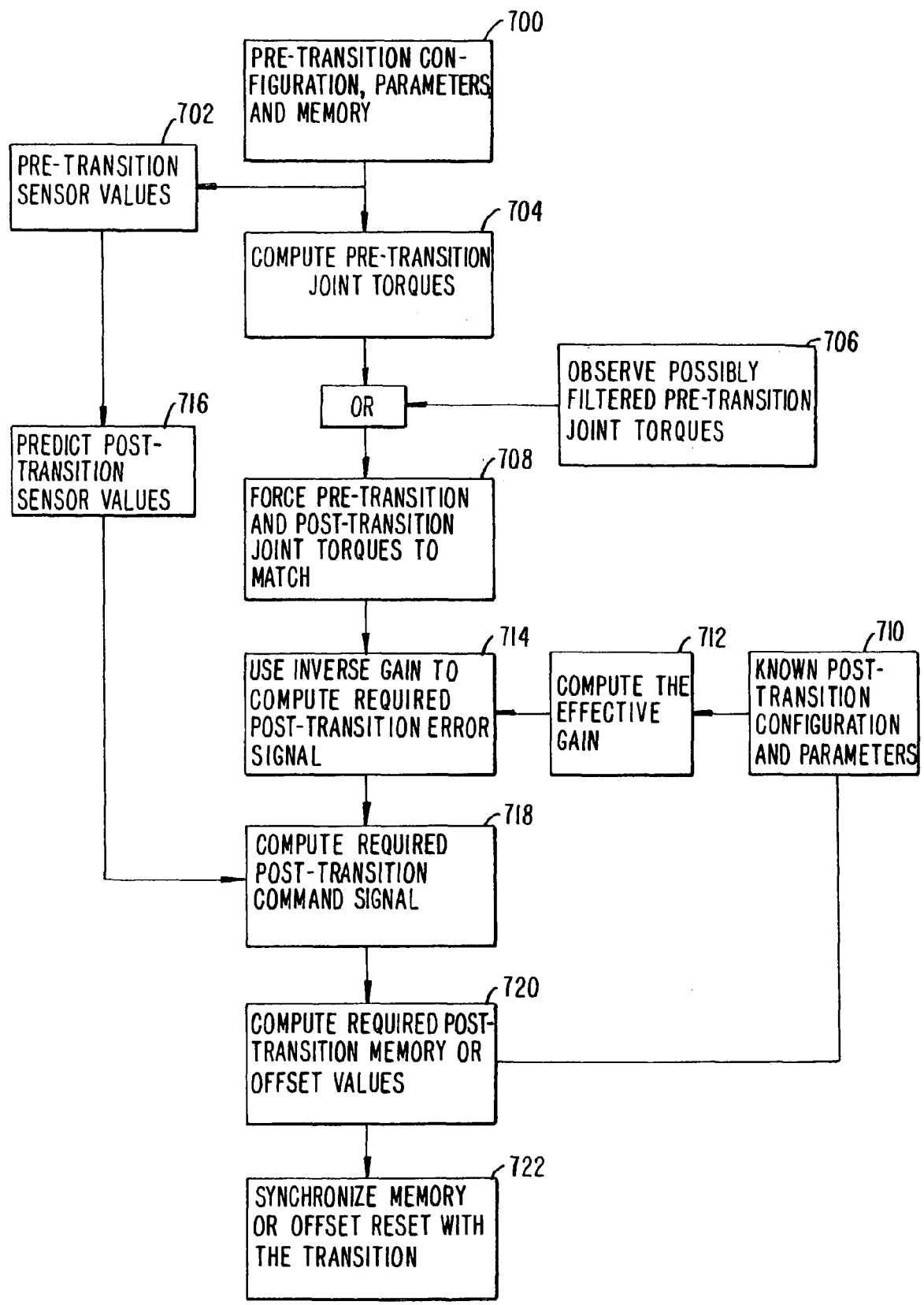
FIG. 19A shows a block diagram indicating the steps involved in smoothly recoupling an input device with an end effector so as to avoid inadvertent sudden movements.

Referring now to FIG. 19A, pre-transition configuration, perimetric values, and memory values are used, together with sampled pre-transition sensor values 702 to compute pre-transition joint torques at step 704. Alternatively, these pre-transition joint torques may be directly observed, optionally with filtering, at step 706. Regardless, post-transition joint torque values are forced to match the pre-transition joint torque values at step 708. Meanwhile, using known post-transition configuration and perimetric values 710, the post-transition effective feedback gains may be determined at step 712. These post-transition effective feedback gains may be inverted and used together with the post-transition joint torques to calculate a desired post-transition error signal at step 714. The post-transition sensor values may be predicted at step 716. These post-transition sensor values may be estimated by assuming that smooth sensor readings will be provided, and knowing the time it takes to effect transition.

The desired post-transition error signal and predicted sensor values may be used to derive a desired post-transition command signal at step 718.

Based on the known post-transition configuration, the post-transition command signal will generally determine the desired memory or offset value through calculations performed at step 720. This post-transition memory or offset value is reset in synchronization with the transition at step 722. Hence, once the desired mode transition is input, information about the configuration of the system before and after the change takes place allows smoothing of the transition.

Repositioning of one of the slaves relative to one of the masters will now be described with reference to FIGS. 14 and 15. It is to be appreciated that both slaves can be repositioned relative to their associated masters simultaneously. However, for ease of explanation the repositioning of a single slave relative to its associated master will now be described.

Figure 14:
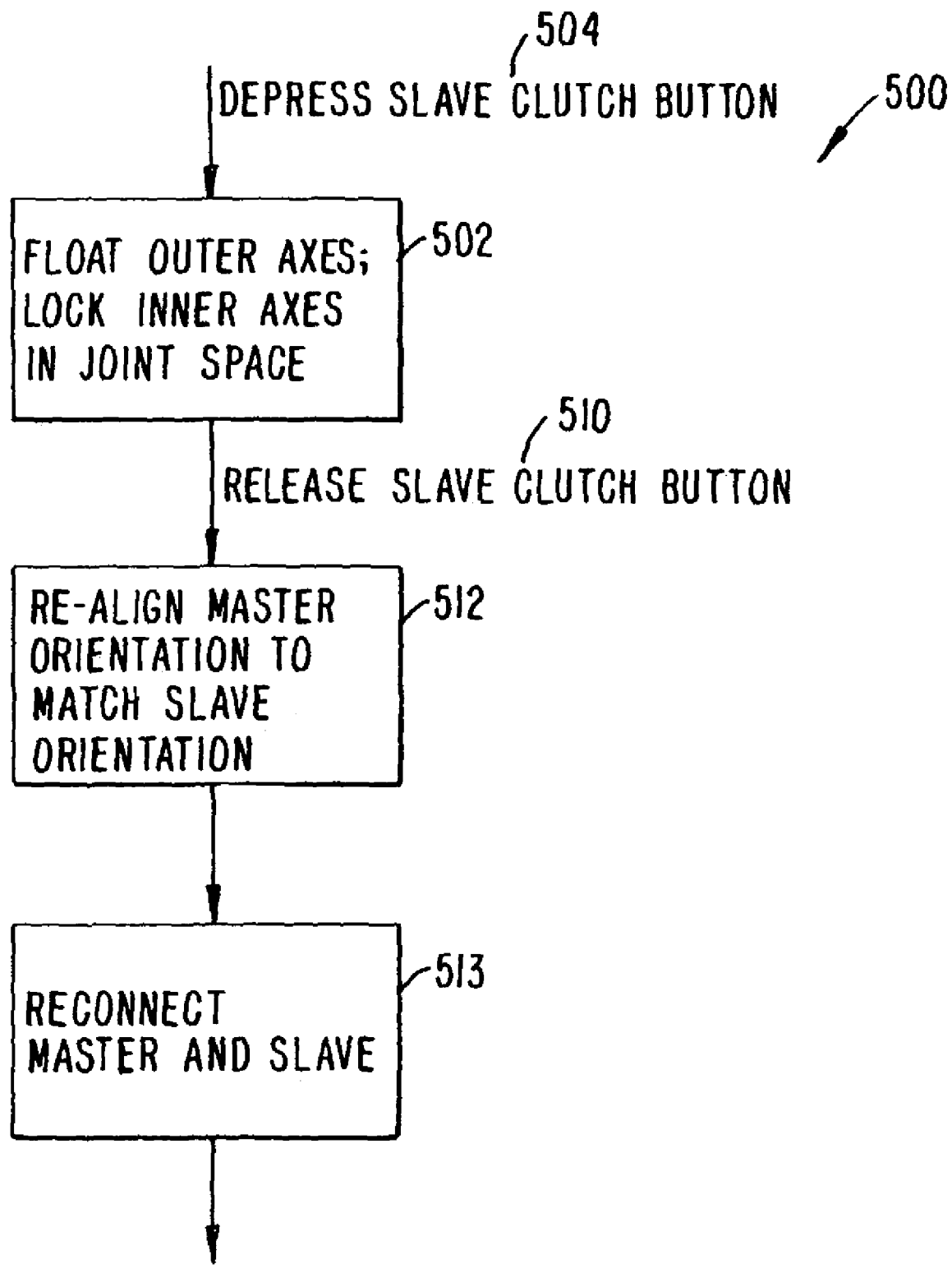
FIG. 14 shows a block diagram indicating the steps involved in moving the position of one of the end effectors relative to its associated master control.
Figure 15:
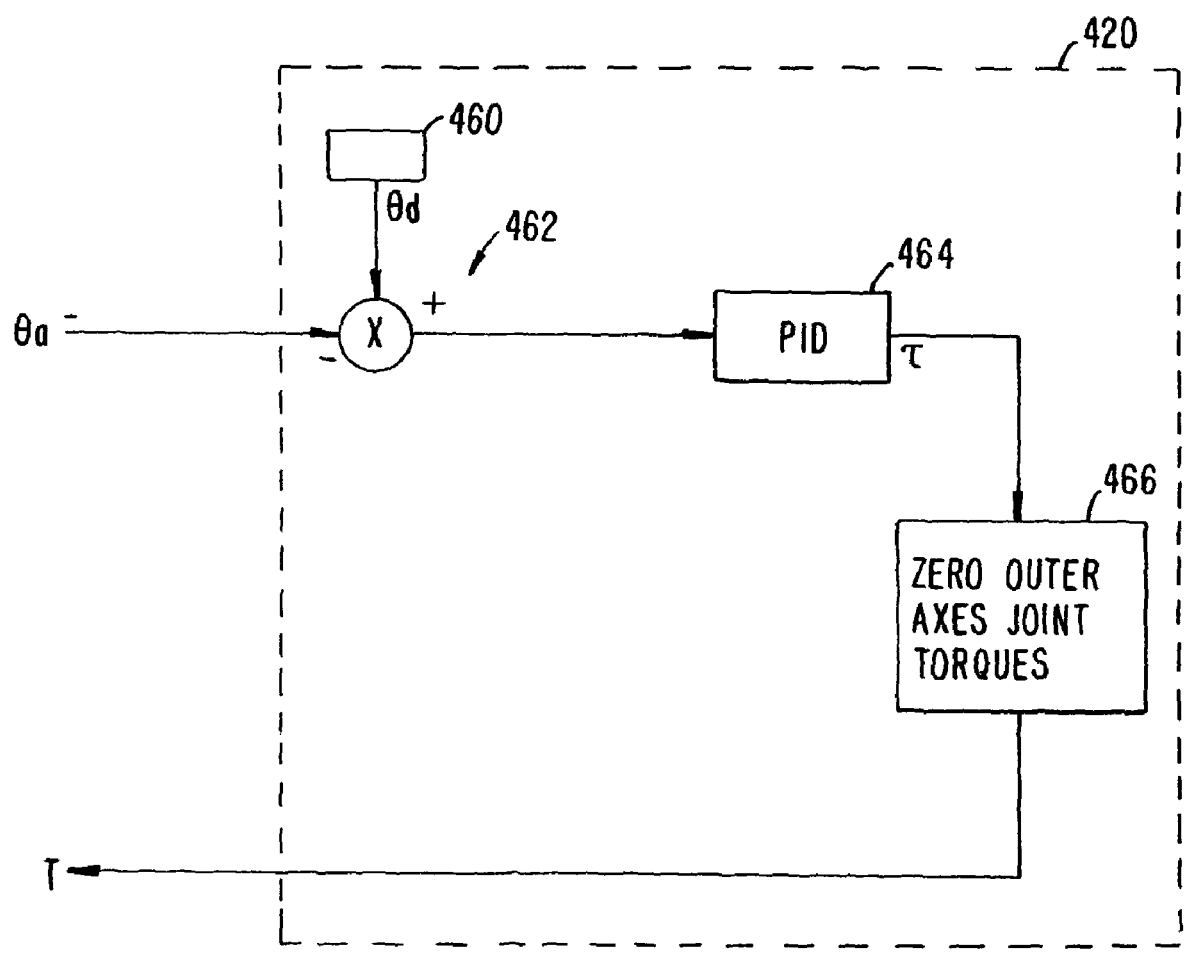
FIG. 15 shows a control diagram which indicates control steps involved when the end effector is moved relative to its associated master control as indicated in FIG. 14.

In FIG. 14 a block diagram indicating steps involved in repositioning a slave relative to its associated master is generally indicated by reference numeral 500. When it is desired to move the end effector of a slave to a new position, a suitable input is activated to interrupt the control loop 400 between the master and the slave. Such a suitable input can be in the form of a button on the robotic arm as indicated at 480 in FIG. 5A. Depressing such a button to interrupt the control loop 400 is indicated by the term "Depress Slave Clutch Button" at 504 in FIG. 14. Once the button is depressed, the control between master and slave is interrupted to cause the translational movements of the slave to float while the orientation of the end effector is locked as indicated at 502 in FIG. 14.

In general, when movements of one or more joints of a master or slave linkage are allowed to float, the floating joints may optionally still have some forces imposed against the joint by their associated joint-drive systems. More specifically, as described more fully in co-pending U.S. patent application Ser. No. 09/287,513, the full disclosure of which is incorporated herein by reference, the controller may impose actuation forces on the master and/or slave so as to compensate for gravity, friction, or the like. These compensation forces may be maintained on the floating joint or joints even when the control link for actuating the joint is otherwise open.

The step indicated at 502 will now be described in greater detail with reference in particular to FIG. 15, and also with reference to FIG. 11. When the button 480 is depressed, the position $\theta_d$ of the slave in joint space immediately before depression of the button is recorded in a memory of the slave joint controller 420, and as indicated at 460. As the slave is moved thereafter, its position in joint space indicated by $\theta_a$ is compared with $\theta_d$ at 462. As $\theta_a$ deviates from $\theta_d$ error signals corresponding to the positional deviation in joint space is determined at 462 and is passed to 464. At 464 required torques for the electric motors on the slave are determined to cause the slave to return to the $\theta_d$ position. The torques thus determined which relate to translational torques of the slaves are zeroed at 466 to permit the slave translational movements to float. The torques corresponding to orientational movement are not zeroed. Thus, any environmental forces on the end effector urging an orientational position change are fed back to the end effector to cause it to retain its orientation. In this way the orientation of the end effector relative to the end of the instrument shaft 104 is locked in position. Although the orientation of the end effector does not change relative to the end of the shaft, it does change in position in Cartesian space as a result of translational position change. It should be understood that zeroing of the outer joint torques at step 466 may be effected by a variety of methods, including zeroing of the appropriate gains in P.I.D. controller 464, continually updating the appropriate elements in memory 460 so as to compute a zero error signal at comparison 462, or the like.

It should be also be understood that a variety of additional operation configurations may be implemented which allow slave transitional movements to float free of the master control. For example, slave transitional forces may be zeroed in Cartesian space (analogous to the master clutching algorithm described with reference to FIGS. 12 and 13). Alternatively, control system 400 and/or bilateral controller 410 may be interrupted only for translational motions, locking the master translational position and allowing the slave to float in transnational position, all while connecting the master orientation to the slave orientation. Once the slave is at the desired position the button is released as indicated at 510 in FIG. 14.

When the button is released, the master orientation is re-aligned with the slave orientation as indicated at 512. The re-aligning of the orientation of the master and slave is now described with reference to FIG. 18. The steps involved in such re-alignment are generally indicated by reference numeral 550.

At 552 the slave position $\theta_s$ in joint space is read. The position $\theta_s$ is then converted to a position $x_s$ in Cartesian space at 554 using slave forward kinematics. Thereafter at 556, the desired orientation of the master is set to equal the slave orientation in Cartesian space. Thus $x_m$, the master orientational position in Cartesian space is set to equal $x_s$, the slave orientational position in Cartesian space. Thereafter at 558, inverse master kinematics is employed to determine the master joint position $\theta_m$ in joint space which corresponds to $x_m$, the master position in Cartesian space. Finally, the master is then caused to move to $\theta_m$ by causing appropriate signals to be sent to the motors on the master as indicated at 560. It will be appreciated that the surgeon will generally release the master to enable it to move into an orientation aligned with the slave orientation.

Referring again to FIG. 14, after the re-alignment step at 512, the master is reconnected to the slave as indicated at 513. It will be appreciated that the step 513 is the same as that described above with reference to FIG. 19. The master realignment is described in more detail in Application Serial No. 60/116,842.

Figure 16:
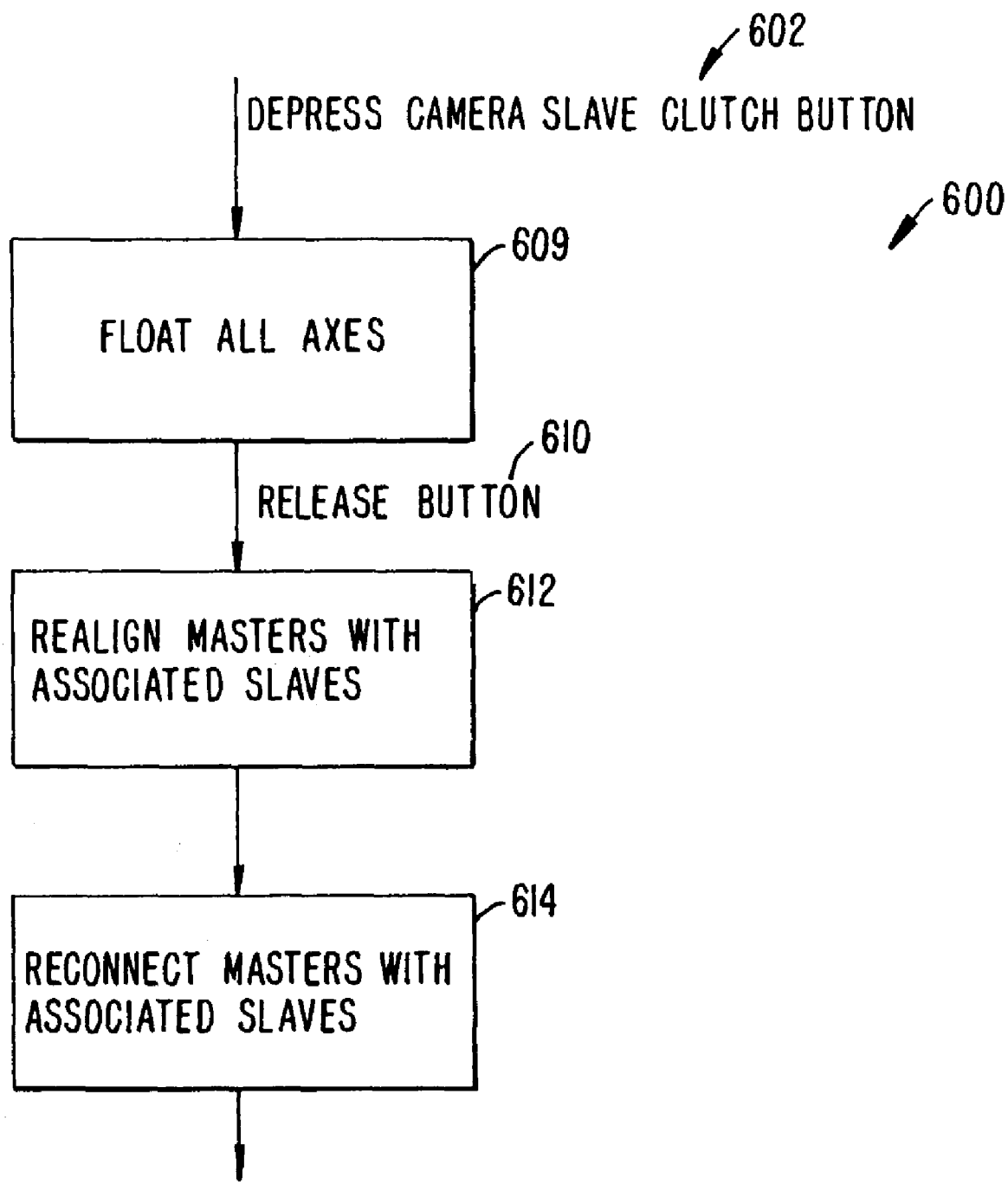
FIG. 16 shows a block diagram indicating the steps involved in moving the position of a viewing end of an endoscope of the minimally invasive telesurgical system relative to the end effectors.
Figure 17:
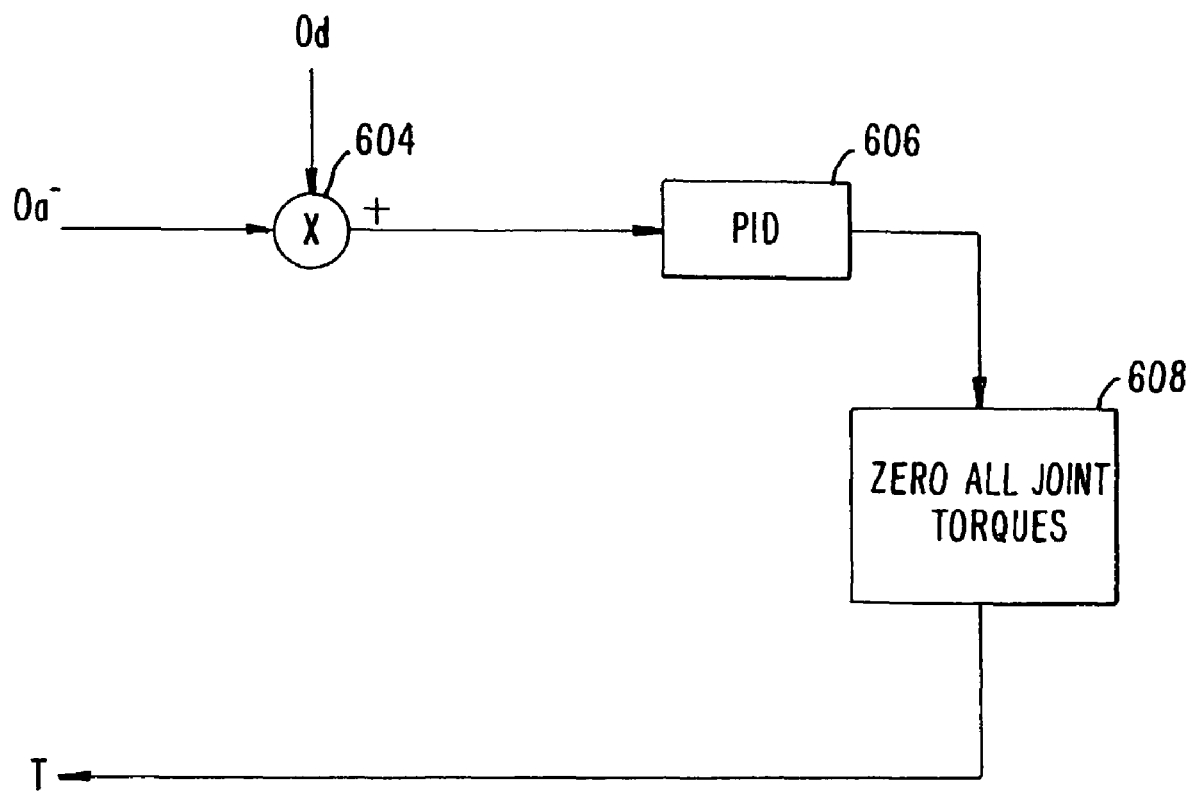
FIG. 17 shows a control diagram which indicates control steps involved when the end of the endoscope is moved relative to the end effectors as indicated in FIG. 16.

Endoscope Movement. Referring now to FIGS. 11, 16, and 17, repositioning of the endoscope to capture a different view of the surgical site will now be described. As the surgeon may wish to view the surgical site from another position, endoscope arm 302 can selectively be caused to vary its position so as to enable the surgical site to be viewed from different positions and angular orientations. The arm 302 includes appropriately positioned electrical motors controllable from the control station 200. The endoscope arm can thus be regarded as a slave and is typically controllable in a control loop similar to that shown in FIG. 11. Regarding the endoscope as another slave, cart 300 has three slaves, the robotic arm assemblies 310 and 304, and two masters 210.

To vary the position of the endoscope, the surgeon activates an input at the control station 200. The input can be generated from any appropriate input device, which can include a depressible button, or a voice control system, or the like. Upon such activation, the control loops between master 210 and slaves 310 one of which is indicated in FIG. 11, are interrupted and the parts of the control loop on both master sides are operatively linked to a dormant control loop portion similar to that of the slave in FIG. 11, but which is arranged to control endoscope arm movement. The surgeon can then change the position of the endoscope to obtain a different view of the surgical site by means of manual inputs on the master controls 210. When the endoscope has been moved to a desired position, control between master and slave is re-established in accordance with the methods described above including automatic assessment of left and right hand allocation between masters and slaves as already discussed.

An exemplary method and system for robotic movement of the endoscope using both of the master controllers is described in more detail in Application Serial No. 60/111,711, filed on Dec. 8, 1998, and entitled "Image Shifting for a Telerobotic System," the full disclosure of which is incorporated herein by reference.

At times, such as when the scope is moved to an alternative minimally invasive aperture, or when a scope is removed and replaced, the endoscope may be manually positioned. The steps involved in repositioning the endoscope are indicated by reference numeral 600 in FIG. 16. To do this a suitable input device is activated.

The suitable input device is typically in the form of a depressible button on the endoscope arm 302. However other methods such as voice control or the like can be used instead. The button is similar to the button on the arm 312 as described above. The depressing of such a button is indicated at 602 in FIG. 16 and is labeled "Depress camera slave clutch button". Upon activation of the input button the tool slaves and masters are servo locked at the positions they were at immediately before activation of the input button.

When the button is depressed, all the joints on the endoscope arm 302 are caused to float as indicated at 609. This will now be described in greater detail with reference to FIG. 17. As soon as the button is depressed, the position of the endoscope in joint space immediately before depression of the button is recorded as indicated by $\theta_d$. When the endoscope arm 302 is then moved to a new desired position, its present position indicated by $\theta_a$ in FIG. 17 is compared with $\theta_d$ at 604 to determine joint positional errors or deviations. These errors are passed to 606. The torques then determined are zeroed at 608 to cause the joints on the endoscope arm to float to enable repositioning.

It will be appreciated that floating the endoscope arm can also be achieved by setting the gains in 606 to zero or continually updating $\theta_d$ to watch $\theta_a$ as to compute a zero error signal at 604. Similarly one might disable the endoscope arm controller altogether or zero the motor commands.

It will also be appreciated that the endoscope could be freed to move in translation while locked in orientation, analogous to the above-described methods. Furthermore, one could control the orientation to keep the image aligned with horizontal or vertical, that is keep the top of the image facing upward (for example, so that gravity is consistently downward in the image shown to the system operator), while floating translational degrees of freedom. Again this is analogous to methods described above, and can be used to disable and/or float aspects of the endoscope controller in Cartesian space.

When the endoscope arm is brought into the required position the button is released as indicated at 610 in FIG. 17. Thereafter the masters are realigned with the slaves as indicated at 612 and as already described with reference to FIG. 18. Thereafter at 614 control between master and slave is re-established and as already described with reference to FIG. 19.

Though the above algorithms for repositioning masters, slaves and/or the endoscope arm were described in isolation, they can also be executed in parallel, allowing for simultaneous repositioning of any number of system components.

Figure 20:
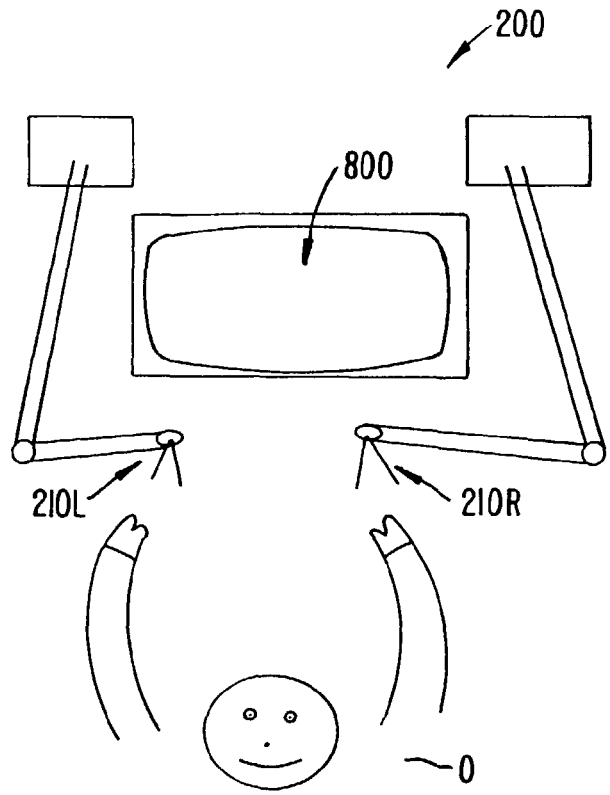
FIG. 20 shows a schematic diagram indicating an operator of the minimally invasive telesurgical system of the invention at the control station shown in FIG. 2.

Left-Right Tool Swap. Referring now to FIG. 20 of the drawings, in which like reference numerals are used to designate similar parts unless otherwise stated, an image as viewed by the surgeon, and as captured by the endoscope, is generally indicated by reference numeral 800.

During the course of a surgical procedure, the surgeon is often controlling the actions and movements of the end effectors by inputting manual movements and actions on the master controls while viewing the corresponding end effector movements and actions in the image displayed on the viewer. The left hand master control is typically operatively associated with the end effector displayed on the left hand side of the image and the right hand master control is operatively associated with the end effector displayed on the right hand side of the image.

As described above, the surgeon may wish to perform an image shift by moving the viewing end of the endoscope relative to the surgical site to view the surgical site from a different position or angle. It could happen that during the conducting of the surgical procedure, such as subsequent to an image shift, the end effector which was on the left of the displayed image is now on the right, and similarly the end effector which was on the right of the displayed image is now on the left. Furthermore, during the course of, e.g., training, or the like, an operator of the minimally invasive system may wish to operatively associate the two master controls with a single end effector so as to enhance a training procedure of the system. This invention provides a minimally invasive telesurgical system which provides for selectively permitting operative association of any one or more of a plurality of master controls with any one or more of a plurality of end effectors.

Figure 21:
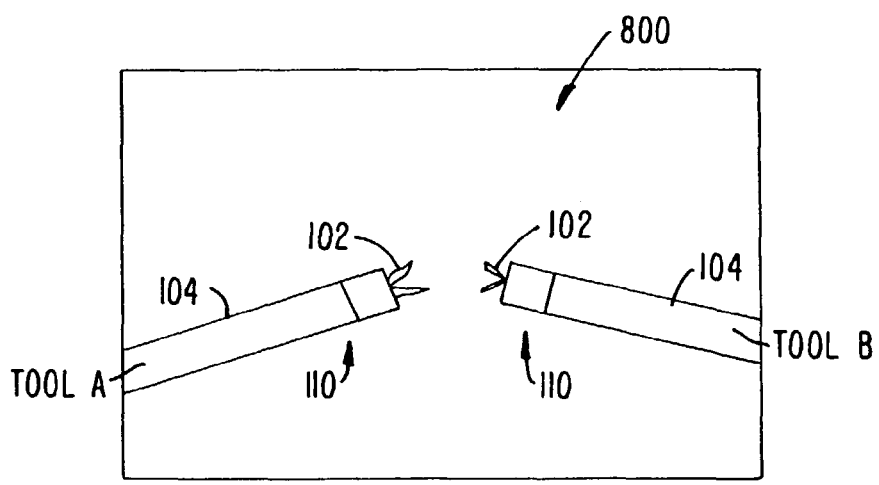
FIG. 21 shows a schematic diagram of an image captured by an endoscope of the minimally invasive telesurgical system of the invention as displayed on a viewer of the system.

The image 800 is schematically indicated in FIG. 21 at an enlarged scale. The image 800 indicates the end effectors 102 at the working ends 110 of two surgical instruments similar to the surgical instrument 100 shown in FIG. 6. In the image, the portions of the shafts 104 of the surgical instruments extend outwardly from the image on respectively a right hand side and a left hand side of the image. Referring again to FIG. 20 of the drawings, the master control device 210 on the right hand side of the surgeon is operatively associated with the slave including the medical instrument defining the shaft extending outwardly toward the right hand side of the image 800. Similarly, the master control device 210 on the left hand side of the surgeon is operatively associated with the slave including the medical instrument defining the shaft extending outwardly toward the left hand side of the image 800. Accordingly, an anthropomorphic or immersive surgical environment is created at the workstation 200 and the surgeon experiences an atmosphere of directly controlling actions and movements of the end effectors 102.

Figure 21A:
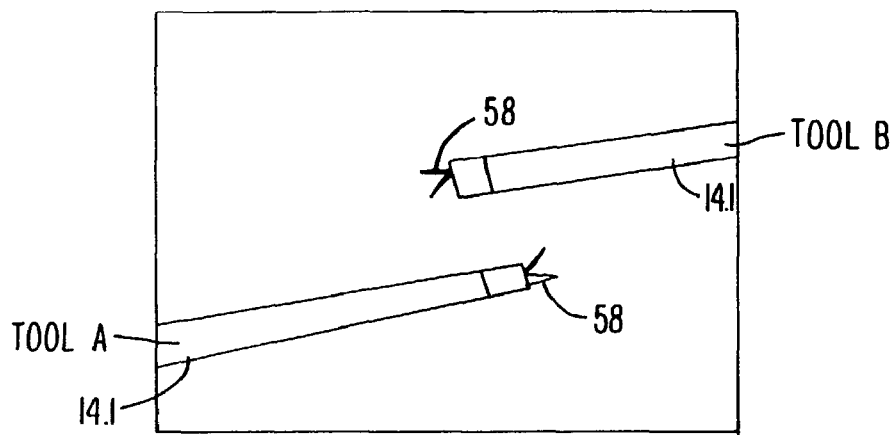
FIG. 21A shows a schematic diagram of another image captured by the endoscope of the minimally invasive telesurgical system of the invention as displayed on the viewer of the system.

In FIG. 21A, the end effectors are shown to be at different positions in the image. However, it is still clear which shaft 104 extends outwardly to the left and right of the image. Accordingly, the same association between the master control devices and the slaves prevails.

Figure 22:
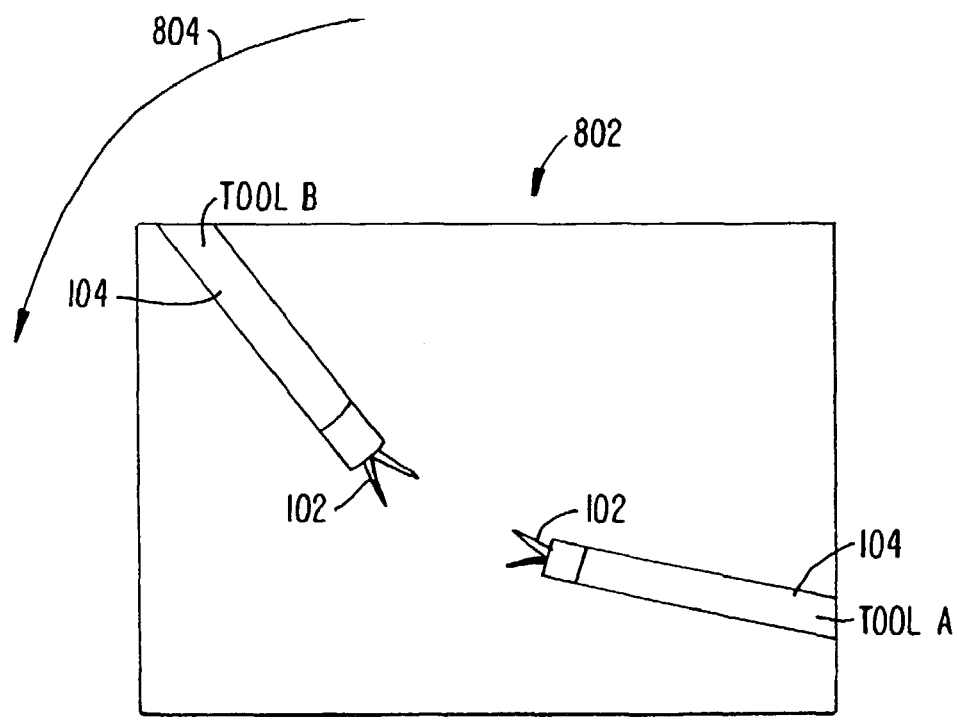
FIG. 22 shows another image captured by the endoscope of the minimally invasive telesurgical system of the invention as displayed on the viewer of the system.

Referring now to FIG. 22 of the drawings, an image shift has taken place. This can happen, for instance, where the surgeon wishes to change the orientation of the surgical site as viewed through the viewer. This can be accomplished by causing the endoscope to displace angularly about its viewing axis. It will be appreciated that the endoscope mounted on the robotic arm 302, as can best be seen in FIG. 5, can be caused to displace angularly about its viewing axis from the control station 200.

The new image 802 shown in FIG. 22 for the sake of example, was brought about by such angular displacement of the endoscope. Accordingly, the image 802 has undergone an angular displacement, as indicated by arrow 804. The shaft of the medical instrument which extended to the right of the image now extends to the left of the image and the shaft of the medical instrument which extended to the left of the image now extends to the right of the image. If the association between masters and slaves which existed immediately before the image shift was to prevail, this would severely impede the surgeon's ability to carry on with the surgical procedure since left hand control would be associated with right hand actions and movements of the end effector as displayed on the viewer, and vice versa.

To compensate for such a situation, the minimally invasive surgical system of the invention causes the association between masters and slaves which prevailed immediately before the image shift, to be interrupted and then to be switched or swapped automatically. Once this has taken place, master control on the surgeon's right hand side is associated with the slave which includes the shaft extending outwardly to the right of the new image and the master control on his or her left hand side is associated with the slave defining the medical instrument having the shaft which extends outwardly to the left of the new image. Thus, the anthropomorphic surgical environment is retained at the control station 200.

Figure 22A:
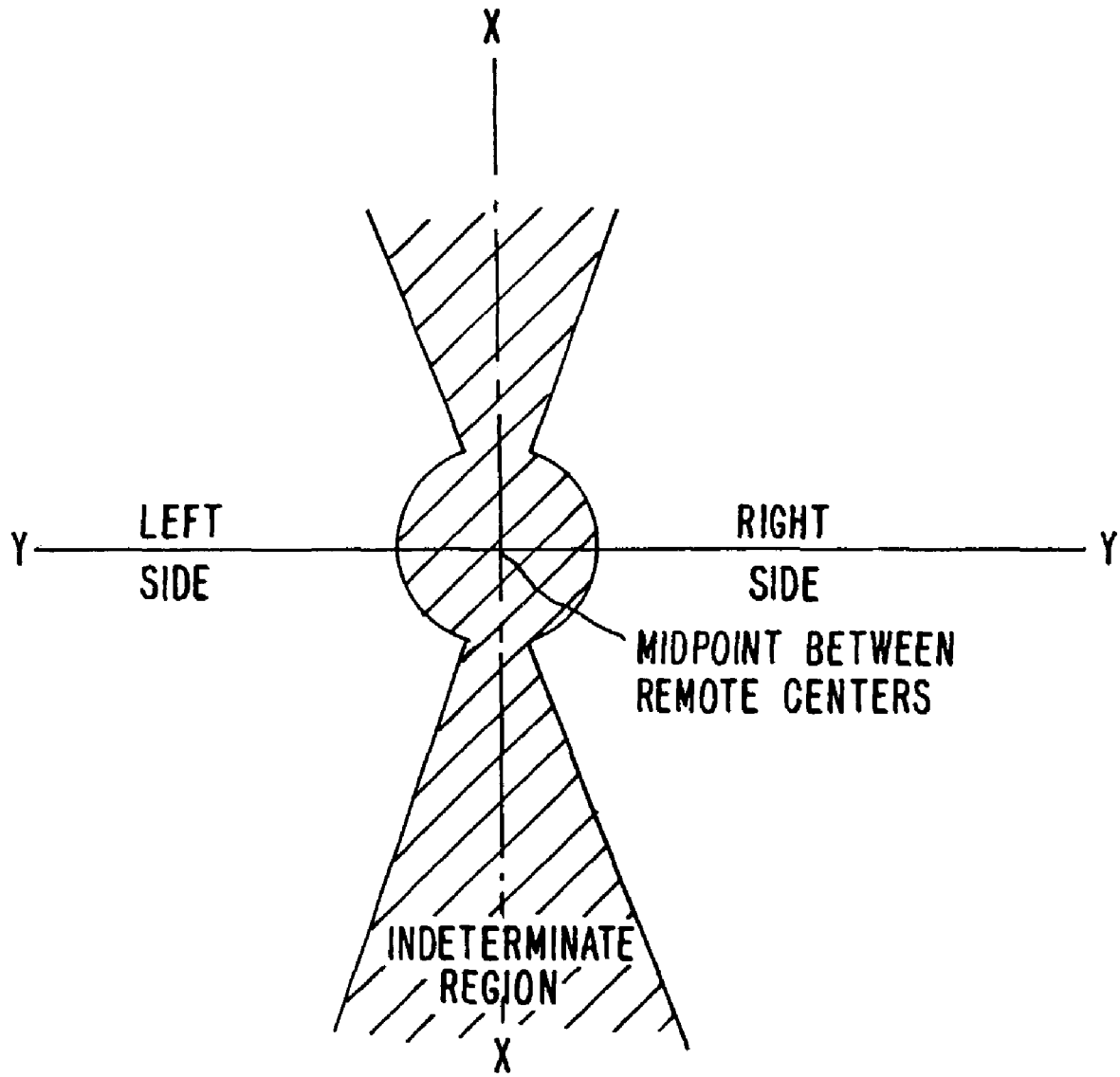
FIG. 22A shows a reference plane indicating a region in dashed lines which corresponds to an area where an automated determination of which of two master control devices of the system is to be associated with which of two slaves of the system is not desired.
Figure 22B:
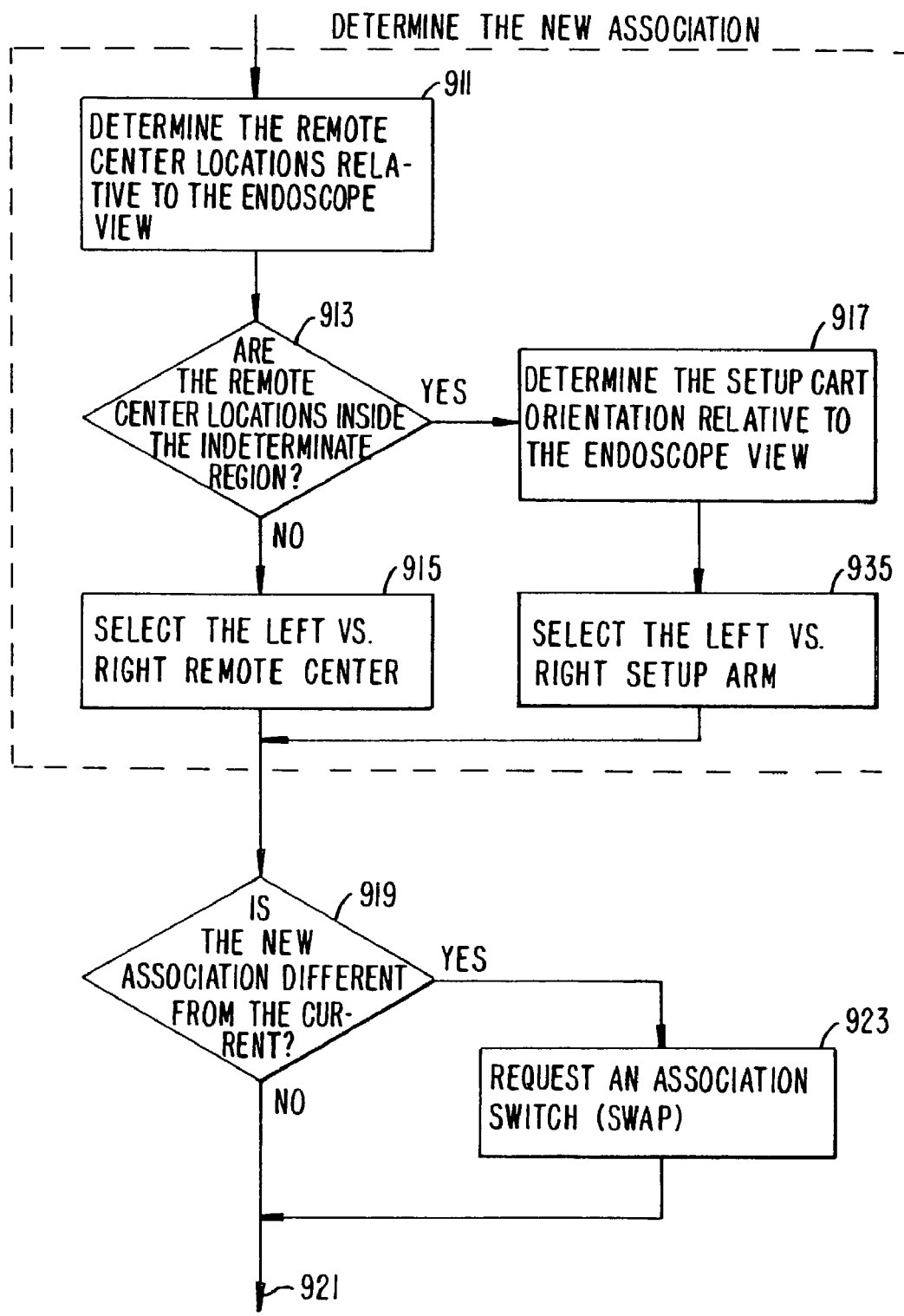
FIG. 22B shows a block diagram indicating steps involved in determining an association between which of the two master control devices is to be associated with which of the two slaves of the system.

Referring now to FIG. 22B of the drawings, the steps involved in causing the association between a master and a slave to be swapped with the association of another master and slave will now be discussed.

The first step, indicated by reference numeral 900 in FIG. 22B of the drawings, is to determine the positions of the remote centers or fulcrums 349 of the slaves relative to a Cartesian space coordinate system having its origin at the viewing end of the endoscope. This step will now be described in greater detail and with reference to FIG. of the drawings.

In other words, in the above discussion, and throughout the remainder of the following discussion, the remote centers or fulcrums 349 are considered coincident with the port of entry (as is typical in the preferred embodiment). In other embodiments, however, these points may not coincide (or even exist, for example, when a distal portion or an endoscopic tool is free to pivot above the insertion point, relying on the tendency of the tool to pivot at this point with no remote center imposed) in which case all calculations should be based on the location of the port of entry. It will also be appreciated that the system may determine these port locations from sensor information and pre-existing knowledge of the cart 300, set-up joints, and manipulator arms. Alternatively, the locations could be determined by other sensors or by processing the image 800 directly to observe and extrapolate the pivot points of the displayed tool shafts.

As described above with reference to FIG. 10, the positions of each fulcrum are generally determined relative to the Cartesian coordinate system 902, optionally using sensors of the set-up joints. This is indicated at step 911 in the method of FIG. 22B after which (at step 913) a determination is made as to whether or not the (X,Y) positions of each fulcrum are sufficiently spaced apart relative to each other to permit the minimally invasive surgical system of the invention to determine a left hand and right hand allocation for the robotic arm assemblies or slaves. This step will now be described in greater detail.

It will be appreciated that the cart or trolley 300 and the robotic arm assemblies 395, 310, and 302 mounted thereon are not mechanically perfect structures. Thus, in computing the (X,Y) coordinates for each fulcrum 349 positional errors can arise due to, e.g., external forces such as gravity, mechanical misalignments, miscalibration and the like. The range of such positional errors which can arise is indicated in FIG. 22A. FIG. 22A indicates the x-x and y-y axes of the coordinate system 902. The circular part of the shaded area in FIG. 22A represents an area corresponding to an error range or margin resulting from such errors as described above. The parts of the shaded area diverging outwardly along the x-x axis and from the circular part represent regions where the positions of the fulcrums are too close to the x-x axis for an appropriate allocation to be made.

To determine whether or not the (X,Y) positions of the fulcrums 349 fall in the shaded area, a midpoint between the (X,Y) positions is transformed onto the x-x and y-y axis as indicated in FIG. 22A such that the midpoint coincides with the origin 904. With reference again to FIG. 22B of the drawings, should the positions of the fulcrums 349 fall outside the shaded error region, the next step as indicated by reference numeral 915 is performed. If not, an alternative method to allocate left and right position is followed as indicated by the step 917, as further described herein below.

The step 915 involves a selection or allocation of a right hand and left hand position to the slaves. Accordingly, the slave defining the fulcrum to the left of the x-x axis in FIG. 22A is assigned the left hand position and similarly the slave defining the fulcrum to the right of the x-x axis is assigned the right hand position.

When this allocation has been made the step indicated at 919 is performed. The step at 919 involves making a comparison between the allocated left and right hand positions with a previous left and right hand allocation. Should these allocations be the same, the association between masters and slaves stays as it was as indicated at 921. Should the allocation not be the same, the step indicated at 923 is performed.

Figure 22C:
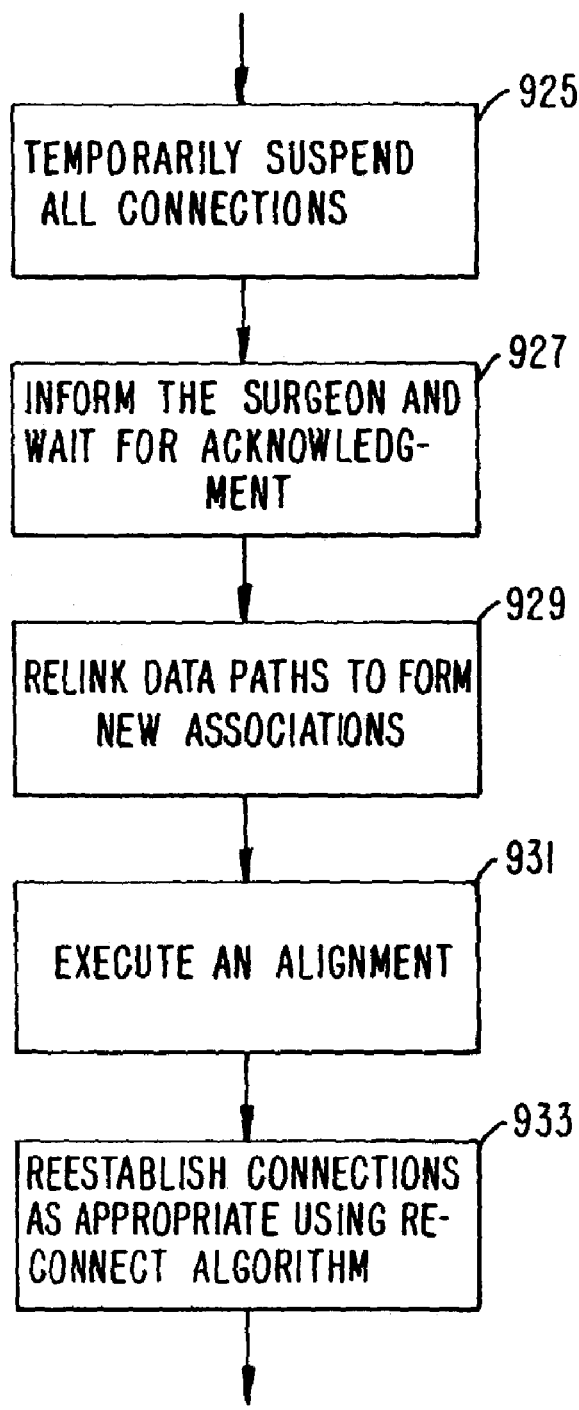
FIG. 22C shows a block diagram indicating steps involved when the association of one of the master control devices with a slave is to be switched or swapped with the association of another master control device and slave.

The step 923 involves requesting a swap between the master and slave associations and will now be described with reference to the block diagram shown in FIG. 22C.

When performing a swap the control loops between the masters and slaves are temporarily interrupted as indicated at 925. This will now be described with reference to FIG. 11 of the drawings. It will be appreciated that the control loop 400 indicates a single control loop which operatively associates a single master with a single slave. The slave side of the loop is indicated below the dashed line in FIG. 11 and the master side of the loop is indicated above the dashed line. It will be appreciated that a similar control loop is provided for the other master and slave pair. The control loop of each master and slave pair are interrupted at the bilateral controller in step 925. Upon such interruption the positions of the masters and slaves are locked in position by means of the respective master and slave joint controllers 420, 560 in the case of each master and slave pair.

Referring again to FIG. 22C, after interruption of the control loops, the surgeon is then informed that a swap is about to take place at step 927. This step typically involves causing a message to be displayed in the image at the viewer. The message can require that the surgeon provide an input to acknowledge his or her awareness of the swap to take place. Such an input can be generated in any appropriate manner such as upon depression of a button, or by means of voice control, or the like. When such an input is generated, operative association between each master and its new associated slave is then established at step 929. Thus, referring once again to FIG. 11 of the drawings, the master side of the control system 400 is linked to the slave side of the other control loop and likewise the master side of the other control loop is linked to the slave side of the control loop 400.

Figure 18:
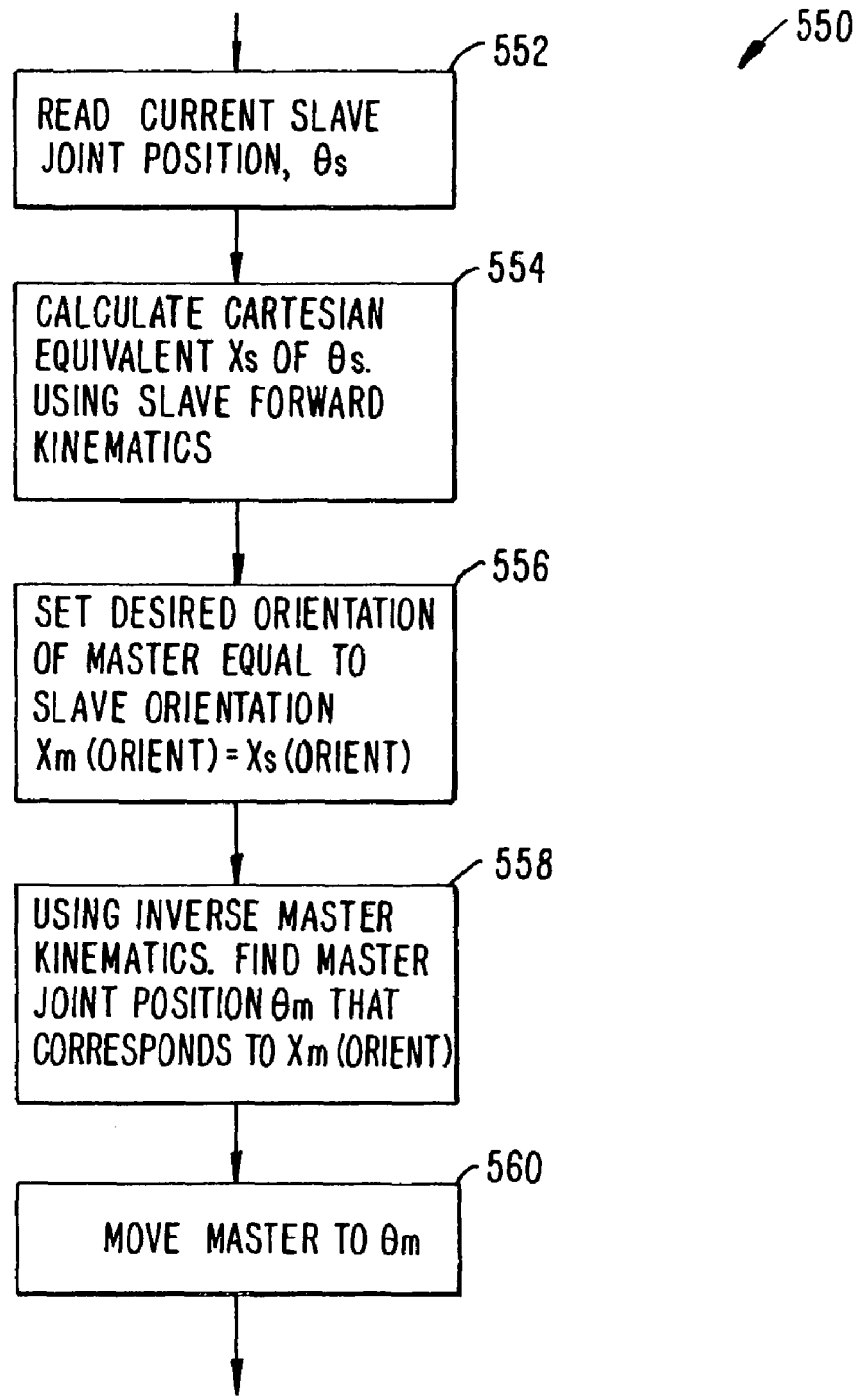
FIG. 18 shows a simplified block diagram indicating the steps involved in realigning a master control device relative to its associated end effector.

Once the control loops have been connected, each master is moved into alignment with its new associated slave at step 931, as described with reference to FIG. 18. Each master can then be connected with its new associated slave at step 933, as described with reference to FIG. 19 of the drawings. Once these steps have been performed, operative control between each master and its new slave is fully established as indicated at 914 in FIG. 22B.

Returning now to FIG. 22B of the drawings, and where the positions of the fulcrums 349 fall within the error margin as indicated in FIG. 22A as determined at 911 in FIG. 22B, the step indicated at 917 will now be described. At 917, an alternative method of determining positions of the fulcrums is employed. This step involves determining the orientation of the endoscope relative to the cart 300. To determine the orientation of the endoscope relative to the cart the positional sensors are employed to determine whether the viewing end of the endoscope is directed toward or away from the cart. Should the end of the endoscope be directed away from the cart, the right hand slave is automatically allocated a right hand position and the left hand slave is automatically allocated a left hand position at the step 935, this allocation presuming a direction of view as indicated by arrow K in FIG. 4. Should the viewing end of the endoscope be directed toward the cart, the left hand slave is allocated a right hand position and the right hand slave is allocated a left hand position at the step 935. Again, allocation presumes a direction of view as indicated by the arrow K in FIG. 4. This method is based on the presumption that set up joints, indicated by reference numerals 395 in FIG. 9 do not readily cross each other.

It will be appreciated that the endoscope arm 302 can selectively be caused to vary its position so as to enable the surgical site to be viewed from different positions and angular orientations. The arm 302 includes appropriately positioned electrical motors controllable from the control station 200. The endoscope arm can thus be regarded as a slave and is typically controllable in a control loop similar to that shown in FIG. 11.

Both masters can optionally be operatively associated with a single slave, e.g., for training purposes. Employing the methods described above will also enable a surgeon selectively to control any one or more of these multiple slave arms with only two masters. Furthermore, two control stations can be operatively associated with a single cart 200. Thus one master of each control station can then be operatively linked to a single slave arm and each other master control with a single other slave arm. This can be advantageous for e.g., training purposes, or the like.

Regarding the endoscope as another slave, the minimally invasive surgical system of the invention accordingly has three slaves, the robotic arm assemblies 310 and 304, and two masters 210. As described herein, further slave arms may be incorporated as an optional feature.

It will be appreciated that the allocation steps described above for allocating master and slave association are typically automatically carried out at the commencement of a surgical procedure after the slaves have been brought to initial starting positions at the surgical site. Naturally, in addition, or instead, the allocation steps can be initiated manually when appropriate by activating a suitable input to initialize the allocation steps. The steps are also automatically carried out when either one or both masters are repositioned relative to the slaves, when either one or both slaves are repositioned relative to the associated master or masters and when the endoscope is repositioned, as described earlier in this specification. It is to be appreciated that where an input is required in this specification and where appropriate such an input can be by way of any suitable input, such as buttons, cursor selection foot pedal toggling, voice control or any other suitable form of input.

It will furthermore be appreciated that the determination of master-slave association, which is computed automatically according to FIGS. 22A and 22B, may be specified manually by way of a suitable input device, such as buttons, a foot pedal, voice control, mouse input, or any other suitable form. If the association is specified manually, only steps 911 and 916 need be performed to execute the association.

In a system with more than two masters or more than two robotic arms with associated instruments, master-slave association will preferably be entered manually. This can be accomplished by interrupting the current association to allow the master to translate freely as described above with reference to FIGS. 12 and 13, then using the floating master as a mouse-like pointing device to highlight and/or select the image of one of the slaves. To complete the process, the master is locked and the new association activated using steps 919 and 923. Any slaves 9 that are not part of an existing association are locked in joint space using controller 420. The slave location at the time of disassociation is stored in memory in 420, and compared against the sensor signals to provide appropriate feedback torques.

Similarly, in a system with more masters than slaves, only masters selected by appropriate input devices are associated with slaves, while the remainder are locked using a controller such as controller 560.

Figure 23A:
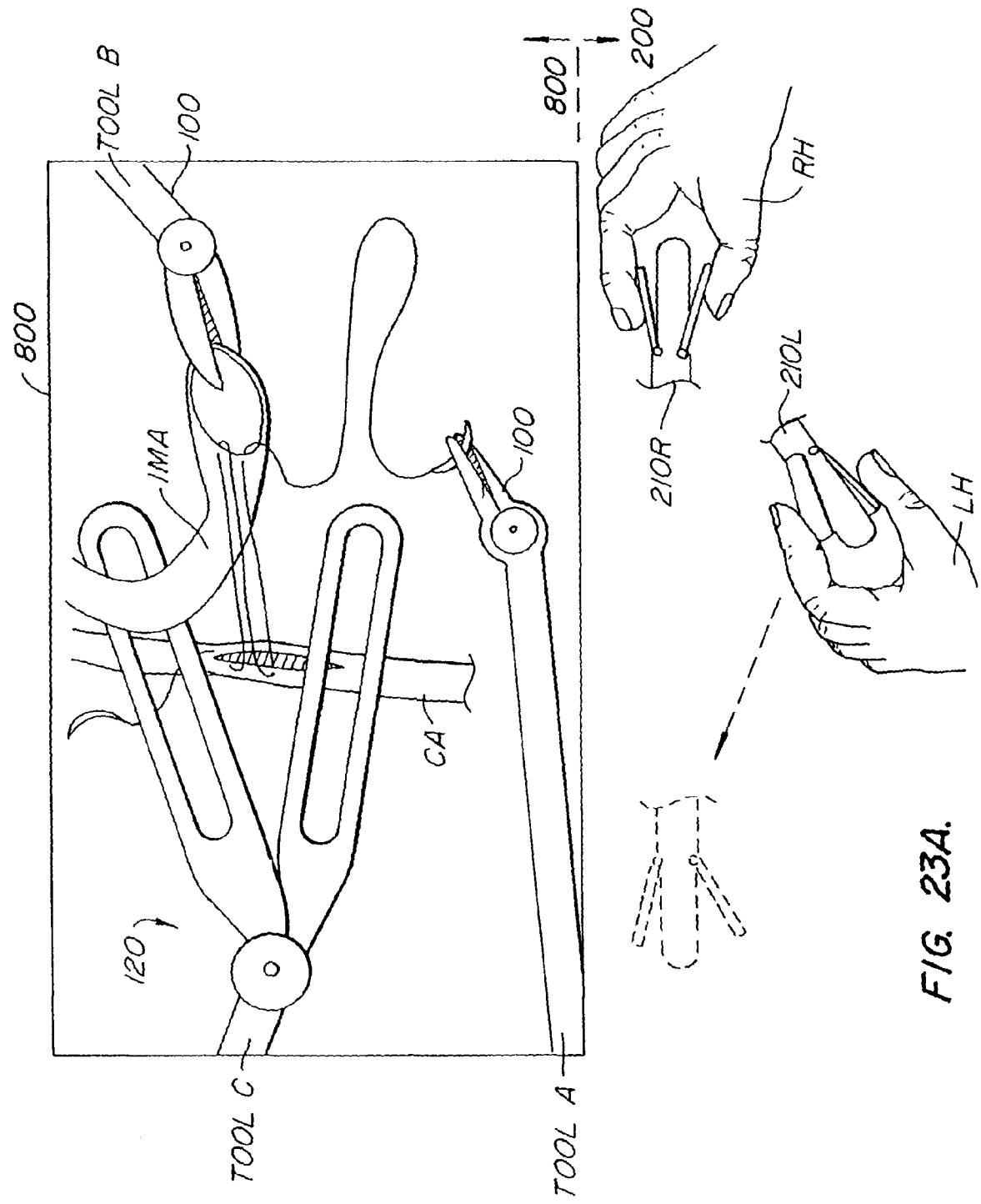
FIGS. 23A and 23B illustrate a system and method for performing coronary artery bypass grafting on a beating heart by selectively associating robotic surgical instruments with master input control devices.
Figure 23B:
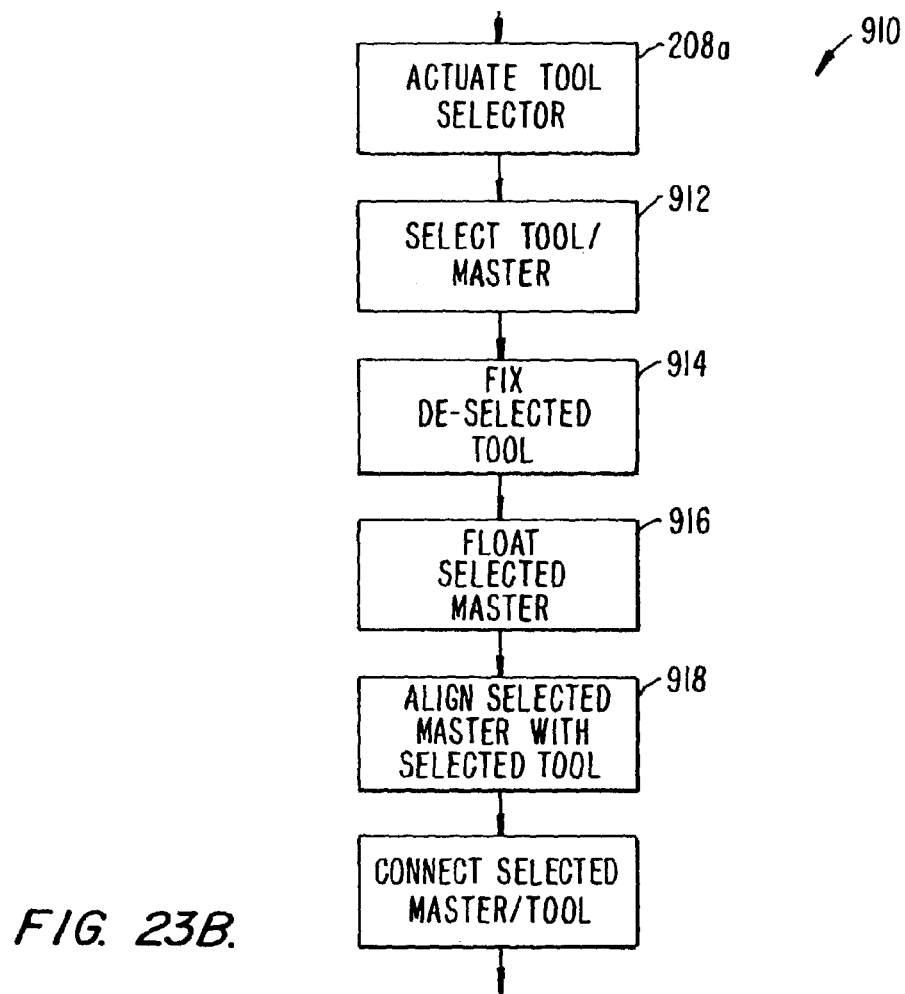

Robotic Network. Referring now to FIGS. 1, 23A and 23B, many of the above steps may be used to selectively associate any of a plurality of tools with any of a plurality of input devices. Operator O may initiate a tool selection subroutine 910 by actuating a tool selector input, such as by depressing foot activated button 208a of workstation 200 (illustrated in FIG. 2). Assuming operator O is initially manipulating tools A and B with input devices 210L and 210R using his or her left and right hands LH and RH, respectively, tool selector procedure 910 will be described with reference to a change of association so that input device 210L is instead associated with a tool C, here comprising a tissue stabilizer 120.

Once the tool selector subroutine is activated, the operator will generally select the desired tools to be actively driven by the robotic system. The surgeon here intends to maintain control over Tool B, but wishes to reposition stabilizer 120. Optionally, operator O will select between the left and right input devices for association with the newly selected tool. Alternatively, the processor may determine the appropriate left/right association based on factors more fully described in co-pending U.S. patent application Serial No. 60/116,891, filed on Jan. 22, 1999, and entitled "Dynamic Association Of Master And Slave In A Minimally Invasive Telesurgical System," the full disclosure of which is incorporated herein by reference.

Optionally, operator O may select the desired tools for use by sequentially depressing selector input 208a, with the processor sequentially indicating selection of, for example, Tools A and B, then B and C, then A and C, and the like. Controller station 200 may indicate which tools are selected on display 800, audibly, or the like. For example, the image of the selected tools viewable by the surgeon may be colored green to designate active manipulation status, and/or the deselected tools may be colored red. Preferably, any deselected tools (for example, Tool A) will be maintained in a fixed position per step 914. The tools may be held in position using a brake system and/or by providing appropriate signals to the drive motors of the tool and arm actuation system to inhibit movement of the tool. The tool fixation step 914 will preferably be initiated before a master input device is decoupled from the tool, so that no tool moves absent an instruction from an associated master. Tool fixation may occur simultaneously with tool selection. The selected master may be allowed to float, step 916, during and/or after tool fixation and tool selection.

Once the selected master has been allowed to float, the master may be moved into alignment with the selected tool as illustrated in FIG. 23A, as was described above with reference to FIG. 18. Often, this will occur while the surgeon keeps a hand on the input device, so that the drive motors of the master should move the master at a moderate pace and with a moderate force to avoid injury to the surgeon. Master input device 210L may then be coupled to tool C (stabilizer 120 in our example) while tool A is held in a fixed position. This allows the operator to reposition stabilizer 120 against an alternative portion of coronary artery CA. The tool selection process may then be repeated to re-associate the masters with tools A and B while tool C remains fixed. This allows the surgeon to control repositioning of stabilizer 120 without significantly interrupting anastomosis of the coronary artery CA with the internal mammary artery IMA.

A number of alternative specific procedures may be used to implement the method outlined in FIG. 23B. Optionally, the interface may allow the operator to manually move the input devices into apparent alignment with the desired tools while the tool selector button is depressed. In FIG. 23A, the surgeon might manually move master 210L from alignment with tool B into approximate alignment with tool C. The processor could then determine the tools to be driven based on the position of the input devices when the button is released, thereby allowing the operator to "grab" the tools of interest. Some or all of the tools (Tools A, B, and C) may optionally be maintained in a fixed configuration when the operator is moving the master controllers to grab the tools.

Allowing an operator to sequentially control more than two robotic tools using the operator's two hands can provide significant advantages. For example, referring again to FIG. 1, by allowing operator O the ability to select in real time and control any one or two tools 100 of cart 300 and auxiliary cart 300A, the surgeon will often be able to act as his or her own assistant.

In addition to allowing the operator to safely reposition a stabilizer 100 against a coronary artery and the underlying beating heart during beating heart coronary artery bypass grafting, a variety of alternative procedures would also be facilitated by such capabilities. As another example, in the procedure of gall bladder removal (cholecystectomy), the surgeon will generally want to first to provide exposure of the organ (retraction) to expose the area of interest. This generally involves guiding a retractor tool (mounted, for example, to a first manipulator arm) to expose an area of interest. The area of interest may be exposed for viewing through an endoscope mounted, for example, to a second manipulator arm. The surgeon might thereafter want to use two hands to direct tools in dissecting tissue covering the cystic duct and artery while the retractor remains stationary. One of the two tools (which may be mounted on third and fourth manipulator arms) can be used to stretch the tissue (traction or grasping) while the other tool is used to cut tissue (sharp dissection) to uncover the vessel and duct structures. Hence, the ability to selectively control four manipulators from a single console allows the surgeon to control the manipulation, retraction/stabilization, and viewing angle of the procedure, without having to verbally instruct an assistant.

At any time during the dissection, the surgeon could have the capability of adjusting the exposed area of the cystic duct by again selectively associating a master input device in his or her left or right hand with the retractor. Once the desired change in exposure is obtained by repositioning the retractor, the surgeon can deselect the retraction tool, and then select and move the endoscope to a more appropriate viewing angle for work on the newly exposed tissue. Thereafter, the surgeon can again select the grasping and cutting tools to manipulate the tissues using both hands.

The ability to control four or more surgical arms also gives the surgeon the capability of selecting from among alternative tools based on tool function and/or anatomical constraints. For example, tools A, B, and C may all have end effectors comprising universal graspers. If the surgeon is afforded a better approach to tissue dissection by using the manipulator arms associated with tools A and B in certain parts of a two-handed dissection procedure, but would prefer to use tools B and C for alternative portions of the two-handed dissection procedure, the operator is free to switch back and forth between tools A and C using tool selection subroutine 910. Similarly, if a cauterizing electrode blade is desired intermittently during a dissection, the operator may switch back and forth between tools A and C to dissect, and then cauterize, and then dissect, etc., without having to wait for an assistant to repeatedly swap tools.

Advantageously, providing a "redundant" manipulator may reduce the need for a laparoscopic surgical assistant who might otherwise be called on to perform intermittent functions by manually manipulating a tool handle extending from an aperture adjacent the manipulator arms. This can help avoid interference between manual tools, personnel, and the moving manipulator arms, and may have economic advantages by limiting the number of highly skilled personnel involved in a robotic surgical procedure. The procedure time may also be decreased by avoiding the time generally taken for a lead surgeon to verbally direct an assistant.

Figure 24:
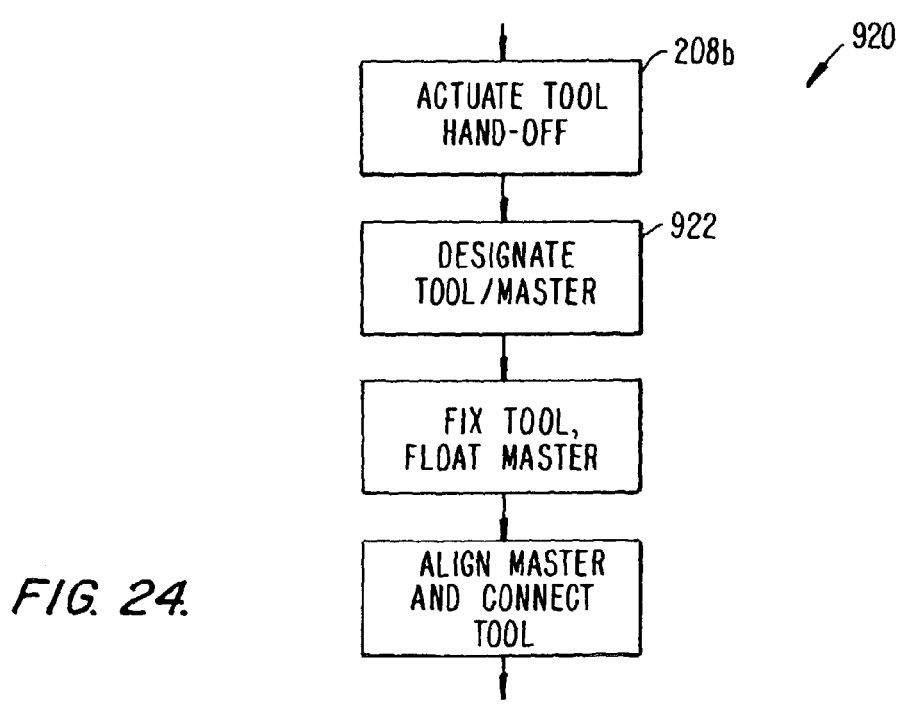
FIG. 24 shows a block diagram indicating steps involved in a method for handing-off control of robotic tools between a surgeon and an assistant.

Tool Hand-Off. Many of the steps described above will also be used when "handing-off" control of a tool between two masters in a tool hand-off subroutine 920, as illustrated in FIG. 24. Tool hand-off is again initiated by actuating an appropriate input device, such as by depressing foot pedal 208b shown in FIG. 2.

The tool to be transferred will typically be designated, again using any of a variety of designation input methods or devices. The transfer tool may be coupled to any master input device or devices, including an input device of master control station 200, assistant control station 200A, or auxiliary input 12 of auxiliary cart 300A (as illustrated in FIG. 1). Optionally, the input device which will assume control of the designated tool is also selected in designation step 922, although selection between left and right masters may again be left to the processor, if desired.

Once the tool and master are designated, the hand-off tool (and any tool previously associated with the designated master) is fixed, and the designated master is allowed to float. The master is then aligned and connected with the tool as described above.

Figure 25A:
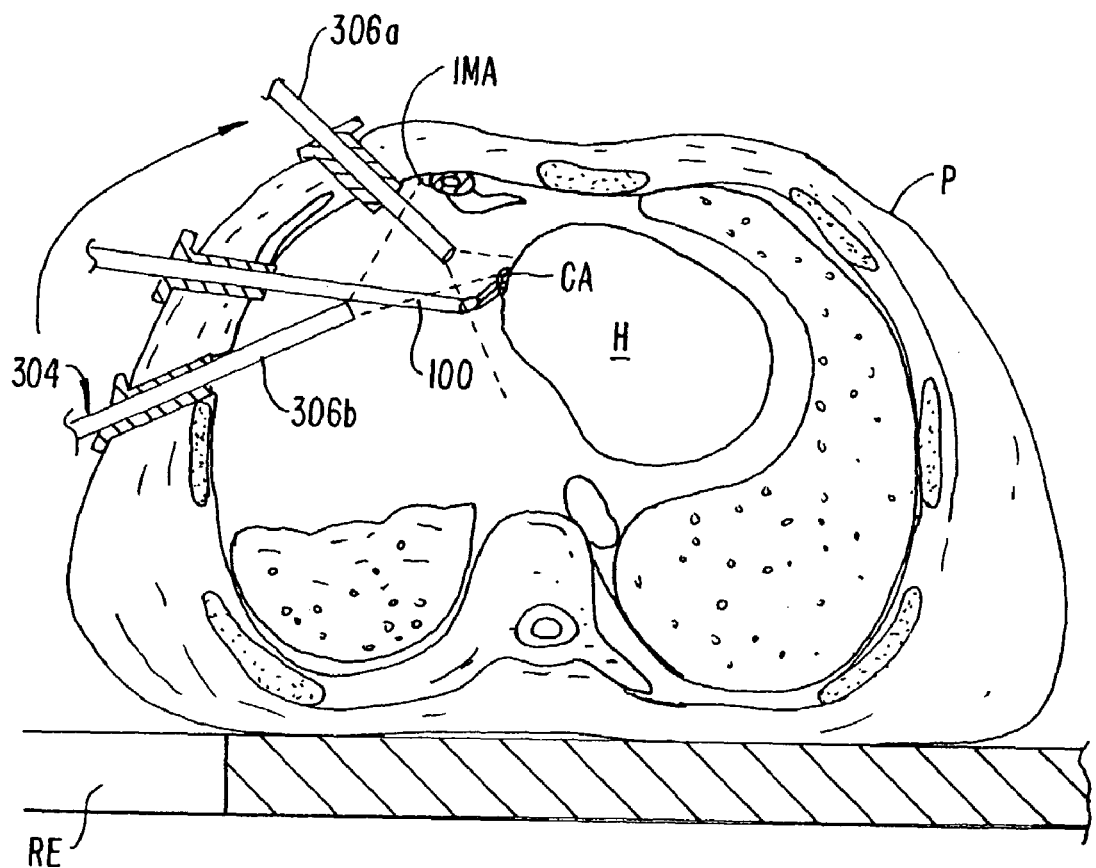
FIG. 25A is a cross section, looking towards the head, through a chest of a patient body, illustrating an endoscopic coronary artery bypass graft procedure in which the heart is treated by robotic tools introduced via a pattern of apertures on the right side of the patient.
Figure 25B:
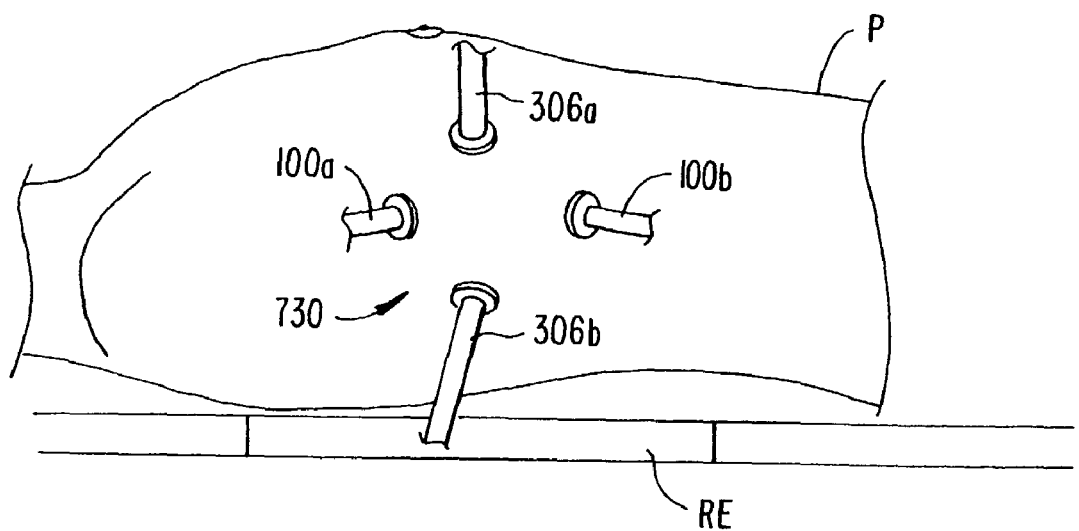
FIG. 25B illustrates an exemplary pattern of four apertures for four robotic endoscopic instruments as used in the procedure of FIG. 25A.

Camera Switch and Right Access Robotic CABG. The following pertains to an exemplary robotic surgery procedure that may be performed with the foregoing apparatuses and methods. Referring now to FIGS. 1, 25A, and 25B, a single complex minimally invasive surgery will often involve interactions with tissues that are best viewed and directed from different viewing angles. For example, in performing a Coronary Artery Bypass Grafting (CABG) procedure on patient P, a portion of the internal mammary artery IMA will be harvested from along the internal surface of the abdominal wall. The internal mammary artery IMA can be used to supply blood to coronary artery CA downstream of an occlusion, often using an end-to-side anastomosis coupling the harvested end of the IMA to an incision in the side of the occluded coronary artery. To provide appropriate images to Operator O at master control station 200, the operator may sequentially select images provided by either a first scope 306a or a second scope 306b for showing on display 800 of the workstation. The camera switch procedure can be understood through a description of an exemplary CABG procedure in which different camera views may be used. Two scopes are shown in FIG. 25A for illustrative purposes only. If only one image is desired, however, the procedure need not employ two endoscopes but instead need only use one together with various instruments for actually performing the procedure.

As seen in FIGS. 1 and 25A, it may generally be beneficial to access heart H primarily through a pattern of apertures 930 disposed along a right side of patient P. Although the heart is primarily disposed in the left side of the chest cavity, approaching the heart from the left side of the chest as is typically done for MIS heart surgery may limit the amount of working volume available adjacent the target coronary tissues. This lack of working volume can complicate thoracoscopic robotic procedures, as the lack of space can make it difficult to obtain a panoramic view of the heart surrounding the tissues targeted for treatment, to quickly insert and remove tools, and to retract the heart appropriately for multi-vessel cases.

By inserting the elongate shafts of instruments 100 through the right side of the patient, the apertures will be further away from the target anatomy, including the left internal mammary artery (LIMA) and heart H. This approach can allow the camera to be separated from the target tissues by a greater distance, such as when a panorama or "big-picture" view is desired, while the resolution of robotic movement maintains the surgeon's dexterity when the scope and tools extend across the chest to the heart tissues for close-up views and work. The right-side approach may also increase the speed with which tools can be changed, as the additional separation between the aperture and the heart helps to ensure that the heart is not in the way when delivering tools to harvest the IMA. When performing multi-vessel cases with the right-side approach, the heart can also be repeatedly retracted and repositioned so as to sequentially expose target regions of the heart to the significant working volume available. Hence, different coronary vessels may selectively be present to operator O for bypassing.

Advantageously, the right-side approach also facilitates dissection of the left internal mammary artery (LIMA) using a medial to lateral approach. This dissection approach can provide a well-defined dissection plane, can increase the ease with which branches can be seen, and may provide a view that is more familiar to surgeons accustomed to traditional CABG performed via a median sternotomy.

As can be seen most clearly in FIGS. 1 and 25B, cart 300 supports first and second tools 100a, 100b for manipulating tissues (more may be used but are not shown) and first scope 306a, while auxiliary cart 300A supports second scope 306b (and/or other manipulator tools, not shown). The arms of cart 300 preferably extend over the patient from the patient's left side, and the instruments extend through aperture pattern 930. The instrument shafts are generally angled to extend radially outwardly from aperture pattern 930 in a "spoked wheel" arrangement to minimize interference between the manipulators. The exemplary arrangement has scopes 306a, 306b extending through apertures defining the top and bottom (anterior and posterior relative to the patient) positions of aperture pattern 930, while the manipulation tool shafts define left and right (inferior and superior relative to the patient) positions. Second scope 306b may be positioned through a lower, more dorsal aperture than shown, with the patient optionally being supported on a table having an edge RE which is recessed adjacent aperture pattern 930 to avoid interference between the auxiliary cart manipulator and the table.

A robotic right-side approach CABG procedure might be outlined as follows:

1. General anesthesia is initiated.
2. Patient is prepped in a basic supine position with a small roll under the patient's scapula and back.
3. Patient is draped so that drapes start at about the posterior axillary line.

LIMA Dissection:

4. Camera aperture for second scope 306b is cut in an appropriate innerspace (usually the $5^{th}$ intercostal space) on approximately the anterior axillary line. The first camera port may be positioned more medially for directing anastomosis, and the like. If provided or desired, the camera aperture for the first scope 306a is cut in an appropriate innerspace (usually the $4^{th}$ or $5^{th}$ intercostal space) slightly posterior to the midclavicular line. Obviously, port placement for the endoscopic tools as well as other portions of this procedure may vary depending upon the anatomy of the particular patient in question.
5. Initiate insufflation at approximately 10 mm Hg.
6. Manipulation tool apertures are cut as appropriate (usually in the $3^{rd}$ and $6^{th}$ or $7^{th}$ intercostal spaces for manipulation instruments 100a, 100b) a few centimeters medial to the anterior auxiliary line. Additional tool ports are placed as desired.
7. Robotic instruments 100a, 100b, 306a, 306b introduced through apertures and robotic telesurgical control system is initiated.
8. LIMA harvesting is initiated by locating midline to establish the beginning of dissection. Harvesting may be viewed and directed using second scope 306b.
9. LIMA is located by moving laterally using blunt dissection and cautery as desired.
10. Left pleura need not be entered, although insufflation can help keep left lung out of the way.

RIMA Dissection (if Desired)

11. The right internal mammary artery (RIMA) may be harvested using steps similar to 1-10 above, optionally through apertures disposed along the left side of the patient's chest.

Pericardiotomy

12. Incision may be made at surgeon's discretion. Preferably, any incision will be high up on the pericardium, so that an attachment of the mediastinum to the chest forms a tent to enhance exposure of the heart.

IMA Preparation

13. IMA(s) may be prepared per surgeon's preference, typically while still attached to the chest.

Aorta Exposure

14. Aorta is exposed by extending the pericardiotomy cephalad as desired. The pulmonary artery and any other adhesions may be dissected off so that the aorta can be clamped for cardiopulmonary bypass and/or proximal grafts. As can be understood with reference to the description above of FIG. 23A, cardioplegia may be avoided by using a manual or robotic cardiac tissue stabilizer mounted to, for example, auxiliary cart 300A during the anastomosis.

Coronary Artery Exposure

15. Target coronary artery or arteries can be exposed to working volume by retracting and repositioning heart as desired, and standard techniques may be used to expose and incise the exposed coronary arteries.

Anastomosis

16. Anastomosis may be performed using needle-grasping tools 100a, 100b while viewing display 800, as illustrated in FIG. 23A.

Suturing and exposure of the aorta and coronary artery or arteries may at least in part be performed while viewing the more anterior-to-posterior field of view provided from first scope 306a, as may portions of all other steps throughout the CABG procedure. When the surgeon desires to change views between first and second image capture devices, the surgeon may initiate the view change procedure by activating a view change input device, possibly in the form of yet another foot switch. The tissue manipulation tools will be briefly fixed in position, and the display will shift between the image capture devices—for example, from the image provided from first scope 306a, to the image provided from second scope 306b.

Optionally, the processor can reconfigure the coordinate transformations between the masters and the end effectors when changing between two different image capture devices to re-establish an at least substantially connected relationship. This transformation modification is similar to the process described above for a change in scope position, but will generally also accommodate the differences in support structure of the image capture devices. In other words, for example, the master and/or slave kinematics 408, 412 (see FIG. 11) may be redefined to maintain a correlation between a direction of movement of the input device 210, and a direction of movement of an image of the end effector 102 as shown in display 202 when viewing the end effector from a different scope. Similarly, when moving second scope 306b (supported by auxiliary cart 300A) as a slave after a scope change from scope 306a (which is supported by cart 300), the slave kinematics 412, slave input/output 414, and slave manipulator geometry 416 may all be different, so that the control logic between the master and slave may be revised as appropriate.

More easily implemented approaches might allow the operator O to switch views between scopes 306a and 306b without major software revisions. Using software developed to perform telesurgery with a single master control station 200 coupled to a single three arm cart 300 (see FIG. 1), switching the view to scope 306b from scope 306a might be accomplished while maintaining the substantially connected relationship by "fooling" the processor of the master control station into believing that it is still viewing the surgery through scope 306a. More accurately, the processor may be fed signals which indicate that the middle set-up joint 395 and/or manipulator arm 302 of cart 300 are supporting scope 306a at the actual orientation of scope 306b. This may be accomplished by decoupling the position sensing circuitry of the middle set-up joint and/or manipulator of cart 300 from the processor, and instead coupling an alternative circuit that transmits the desired signals. The alternative "fooling" circuit may optionally be in the form of a sensor system of an alternative set-up joint and/or manipulator 302, which might be manually configured to hold a scope at the orientation of scope 306b relative to cart 300, but which need not actually support anything. The image may then be taken from scope 306b supported by auxiliary cart 300A, while the slave position signals $x_s$ (See FIG. (11) are taken from the alternative set-up joint. As described above, so long as the orientation of the end effectors relative to the scope are accurately known, the system can easily accommodate positional corrections (such as by the translational clutching procedure described above).

Alternative telesurgical networks are schematically illustrated in FIGS. 26 and 27. As mentioned above, an operator O and an Assistant A3 may cooperate to perform an operation by passing control of instruments between input devices, and/or by each manipulating their own instrument or instruments during at least a portion of the surgical procedure. Referring, now to FIG. 26, during at least a portion of a surgical procedure, for example, cart 305 is controlled by Operator O and supports an endoscope and two surgical instruments. Simultaneously, for example, cart 308 might have a stabilizer and two other surgical instruments, or an instrument and another endoscope A3. The surgeon or operator O and assistant A3 cooperate to perform a stabilized beating heart CABG procedure by, for example, passing a needle or other object back and forth between the surgical instruments of carts 305, 308 during suturing, or by having the instruments of cart 308 holding the tissue of the two vessels being anastomosed while the two instruments of cart 305 are used to perform the actual suturing. Such cooperation heretofore has been difficult because of the volumetric space required for human hands to operate. Since robotic surgical end effectors require much less space in which to operate, such intimate cooperation during a delicate surgical procedure in a confined surgical space is now possible. Optionally, control of the tools may be transferred or shared during an alternative portion of the procedure.

Referring now to both FIGS. 26 and 27, cooperation between multiple systems is also possible. The choice of how many masters and how many corresponding slaves to enable on a cooperating surgical system is somewhat arbitrary. Within the scope of the present invention, one may construct a single telesurgical system's architecture to handle five or six manipulators (e.g., two masters and three or four slaves) or ten or twelve manipulators (e.g., four masters and six or eight manipulators), although any number is possible. For a system having multiple master controls, the system may be arranged so that two operators can operate the same surgical system at the same time by controlling different slave manipulators and swapping manipulators as previously described.

Alternatively, it may be desirable to have a somewhat modular telesurgical system that is capable both of conducting one particular surgical operation with only one operator and, for example, five or six manipulators, and which is also capable of coupling to another modular system having five or six manipulators to perform a second surgical procedure in cooperation with a second operator driving the second system. For such modular systems, five or six manipulator arms are preferably supported by the architecture, although any number may be incorporated into each system. One advantage of the modular system over a single, larger system is that when decoupled, the modular systems may be used for two separate simultaneous operations at two different locations, such as in adjacent operating rooms, whereas such might be quite difficult with a single complex telesurgical system.

As can be understood with reference to FIG. 26, a simple manner of having two surgical systems, each having an operator, to cooperate during a surgical procedure is to have a single image capture device, such as an endoscope, produce the image for both operators. The image can be shared with both displays by using a simple image splitter. If immersive display is desired, the two systems might additionally share a common point of reference, such as the distal tip of the endoscope, from which to calculate all positional movements of the slave manipulators, all as previously described in U.S. Appl. No. 60/128,160. With the exception of the imaging system, each control station might be independent of the other, and might be operatively coupled independently to its associated tissue manipulation tools. Under such a simple cooperative arrangement, no swapping of slave manipulators from one system to another would be provided, and each operator would have control over only the particular slave manipulators attached directly to his system. However, the two operators would be able to pass certain objects back and forth between manipulators, such as a needle during an anastomosis procedure. Such cooperation may increase the speed of such procedures once the operators establish a rhythm of cooperation. Such an arrangement scenario may, for example, be used to conduct a typical CABG procedure, such that one operator would control the endoscope and two tissue manipulators, and the other operator would control two or three manipulators to aid in harvesting the IMA and suturing the arterial blood source to the blocked artery downstream of the particular blocked artery in question. Another example where this might be useful would be during beating heart surgery, such that the second operator could control a stabilizer tool in addition to two other manipulators and could control the stabilizer while the first operator performed an anastomosis.

One complication of simple cooperative arrangements is that if the first operator desired to move the image capture device, the movement might alter the image of the surgical field sufficiently that the second operator would no longer be able to view his slave manipulators. Thus, some cooperation between the operators, such as audible communications, might be employed before such a maneuver.

A slightly more complicated arrangement of surgical manipulators on two systems within the scope of the present invention, occurs when operators are provided with the ability to "swap" control of manipulator arms. For example, the first operator is able to procure control over a manipulator arm that is directly connected to the second operator's system. Such an arrangement is depicted in FIG. 26.

With the ability to operatively hook multiple telesurgical systems together, an arrangement akin to a surgical production line can be envisioned. For example, a preferred embodiment of the present invention is shown in FIG. 27. Therein, a single master surgeon O occupies a central master control operating room. Satellite operating rooms (ORs) 952, 954 and 956 are each operatively connected to the central master console via switching assembly 958, which is selectively controlled by Operator O. While operating on a first patient P1 in OR 956, the patients in ORs 954 and 952 are being prepared by assistants A2 and A3, respectively. During the procedure on patient P1, patient P3 becomes fully prepared for surgery, and A3 begins the surgery on the master control console dedicated to OR 952 by controlling manipulator assembly 964. After concluding the operation in OR 956, Operator O checks with A3 by inquiring over an audio communications network between the ORs whether A3 requires assistance. OR 950 might additionally have a bank of video monitors showing the level of activity in each of the Ors, thereby permitting the master surgeon to determine when it would be best to begin to participate in the various ongoing surgeries, or to hand control off to others to continue or complete some of the surgeries.

Returning to the example, if A3 requests assistance, O selects OR 952 via switching assembly 958, selects a cooperative surgery set-up on an OR-dedicated switching assembly 960, and begins to control manipulator assembly 962. After completion of the most difficult part of the surgery in OR 952, O switches over to OR 954, where patient P2 is now ready for surgery.

The preceding description is a mere example of the possibilities offered by the cooperative coupling of masters and slaves and various telesurgical systems and networks. Other arrangements will be apparent to one of skill in the art reading this disclosure. For example, multiple master control rooms can be imagined in which several master surgeons pass various patients back and forth depending on the particular part of a procedure being performed. The advantages of performing surgery in this manner are myriad. For example, the master surgeon O does not have to scrub in and out of every procedure. Further, the master surgeon may become extremely specialized in performing part of a surgical procedure, e.g., harvesting an IMA, by performing just that part of a procedure over and over on many more patients than he otherwise would be able to treat. Thus, particular surgical procedures having distinct portions might be performed much more quickly by having multiple surgeons, with each surgeon each performing one part of the procedure and then moving onto another procedure, without scrubbing between procedures. Moreover, if one or more patients (for whatever reason) would benefit by having a surgeon actually be present, an alternative surgeon (different from the master surgeon) may be on call to one or more operating rooms, ready to jump in and address the patient's needs in person, while the master surgeon moves on treat another patient. Due to increased specialization, further advances in the quality of medical care may be achieved.

In addition to enabling cooperative surgery between two or more surgeons, operatively hooking two or more operator control stations together in a telesurgical networking system also may be useful for surgical training. A first useful feature for training students or surgeons how to perform surgical procedures would take advantage of a "playback" system for the student to learn from a previous operation. For example, while performing a surgical procedure of interest, a surgeon would record all of the video information and all of the data concerning manipulation of the master controls on a tangible machine readable media. Appropriate recording media are known in the art, and include videocassette or Digital Video Disk (DVD) for the video images and/or control data, and Compact Disk (CD), e.g., for the servo data representing the various movements of the master controls.

If two separate media are used to record the images and the servo data, then some method of synchronizing the two would be desirable during feedback, to ensure that the master control movements substantially mirror the movements of the slave manipulators in the video image. A crude but workable method of synchronization might include a simple time stamp and a watch. Preferably, both video images and servo data would be recorded simultaneously on the same recording medium, so that playback would be automatically synchronized.

During playback of the operation, a student could place his hands on the master controls and "experience" the surgery, without actually performing any surgical manipulations, by having his hands guided by the master controls through the motions of the slave manipulators shown on the video display. Such playback might be useful, for example, in teaching a student repetitive motions, such as during suturing. In such a situation, the student would experience over and over how the masters might be moved to move the slaves in such a way as to tie sutures, and thus hopefully would learn how better to drive the telesurgical system before having to perform an operation.

The principles behind this playback feature can be built upon by using a live hand of a second operator instead of simple data playback. For example, two master control consoles may be connected together in such a way that both masters are assigned to a single set of surgical instruments. The master controls at the subordinate console would follow or map the movements of the masters at the primary console, but would preferably have no ability to control any of the instruments or to influence the masters at the primary console. Thus, the student seated at the subordinate console again could "experience" a live surgery by viewing the same image as the surgeon and experiencing how the master controls are moved to achieve desired manipulation of the slaves.

An advanced version of this training configuration includes operatively coupling two master consoles into the same set of surgical instruments. Whereas in the simpler version, one console was subordinate to the other at all times, this advanced version permits both master controls to control motion of the manipulators, although only one could control movement at any one time. For example, if the student were learning to drive the system during a real surgical procedure, the instructor at the second console could view the surgery and follow the master movements in a subordinate role. However, if the instructor desired to wrest control from the student, e.g., when the instructor detected that the student was about to make a mistake, the instructor would be able to override the student operator by taking control over the surgical manipulators being controlled by the student operator. The ability to so interact would be useful for a surgeon supervising a student or second surgeon learning a particular operation. Since the masters on the instructor's console were following the surgery as if he were performing it, wresting control is a simple matter of clutching into the surgery and overriding the control information from the student console. Once the instructor surgeon had addressed the issue, either by showing the student how to perform a certain part of the surgical procedure or by performing it himself, the instructor could clutch out of the operation and permit the student to continue.

An alternative to this "on-off" clutching—whereby the instructor surgeon is either subordinate to the student or in command—would be a variable clutch arrangement. For example, again the instructor is subordinate to the student's performance of a procedure, and has his masters follow the movement of the student's master controls. When the instructor desires to participate in the procedure, but does not desire to wrest all control from the student, the instructor could begin to exert some control over the procedure by partially clutching and guiding the student through a certain step. If the partial control was insufficient to achieve the instructor's desired result, the instructor could then completely clutch in and demonstrate the desired move, as above. Variable clutching could be achieved by adjusting an input device, such as a dial or a foot pedal having a number of discrete settings corresponding to the percentage of control desired by the instructor. When the instructor desires some control, he or she could operate the input device to achieve a setting of, for example, 50 percent control, in order to begin to guide the student's movements. Software could be used to calculate the movements of the end effectors based on the desired proportionate influence of the instructor's movements over the student's. In the case of 50% control, for example, the software would average the movements of the two sets of master controls and then move the end effectors accordingly, producing resistance to the student's desired movement, thereby causing the student to realize his error. As the surgeon desires more control, he or she could ratchet the input device to a higher percentage of control, finally taking complete control as desired.

Other examples of hooking multiple telesurgical control stations together for training purposes will be apparent to one of skill in the art upon reading this disclosure. Although these training scenarios are described by referring to real surgery, either recorded or live, the same scenarios could be performed in a virtual surgical environment, in which, instead of manipulating the tissue of a patient (human or animal) cadaver, or model, the slave manipulators could be immersed, in a virtual sense, in simulation software. The software would then create a simulated virtual surgical operation in which the instructor and/or student could practice without the need for a live patient or an expensive model or cadaver.

While the present invention has been described in some detail, by way of example and for clarity of understanding, a variety of changes, adaptation, and modifications will be obvious to those of skill in the art. For example and without limiting effect, robotic systems having more than four manipulators and/or more that two scopes may be provided. The manipulator arms can all be mounted to a single support base, or might be arranged with two arms on each of two separate support bases. Hence, the scope of the present invention is limited solely by the appended claims.

What is claimed is:

1. A robotic surgical system comprising:
a plurality of manipulator arms;
a master controller having a first input device for manipulation by a first hand of an operator and a second input device for manipulation by a second hand of the operator;
an assistant controller having an assistant input device for manipulation by a hand of an assistant; and
a processor configured to switch associations between the plurality of manipulator arms and the input devices of the master and assistant controllers in response to selection inputs received from the operator during the performance of a medical procedure to operatively couple the operator selected manipulator arms to the operator selected input devices.

2. The robotic surgical system of claim 1, further comprising an arm selector coupled to the processor for selecting between a plurality of modes, wherein a first arm is operatively associated with the assistant controller when the processor is in a first mode, and wherein the first arm is operatively associated with the master controller when the controller is in a second mode, the operatively associated arm moving the associated surgical instrument in response to movement of the operatively associated input device.

3. The robotic surgical system of claim 1, wherein a second arm is operatively associated with the master controller when the processor is in the first mode, and wherein the second arm is operatively associated with the assistant controller when the processor is in the second mode.

4. A robotic surgical method comprising:
robotically moving a surgical instrument with a manipulator arm in response to manipulation of an associated first input device during a minimally invasive surgical procedure;
interrupting control of the surgical instrument by the first input device;
changing the association of the manipulator arm from the first input device to a second input device during the minimally invasive surgical procedure;
engaging control of the surgical instrument by the associated second input device; and
robotically moving the surgical instrument with the manipulator arm in response to manipulation of the second input device.

5. A minimally invasive robotic surgical system comprising:
two input devices;
an image capture robotic arm assembly;
at least two medical instrument robotic arm assemblies; and
a control system configured to control movement of the instrument robotic arm assembly in response to manipulation of one of the two input devices and control movement of the other instrument robotic arm assembly in response to manipulation of the other of the two input devices, disengage control of at least one of the two input devices from its operatively associated medical instrument robotic arm assembly, engage control of the image capture robotic arm assembly by the at least one input device during the performance of a minimally invasive surgical procedure upon receiving a command to do so, and control movement of the image capture robotic arm in response to manipulation of the at least one input device.

6. A method performed during a medical procedure on a patient, the method comprising:
robotically moving a first surgical instrument using a first manipulator arm in response to manipulation of an input device to perform a task of the medical procedure;
reconfiguring a control system during the medical procedure in response to a command so that the control system decouples the input device from the first manipulator arm and couples the input device to a second manipulator arm; and
robotically moving a second surgical instrument using the second manipulator arm in response to manipulation of the input device to perform another task of the medical procedure.

7. A robotic surgical system comprising:
a slave manipulator holding a tool for performing a minimally invasive surgical procedure;
first and second master manipulators;
an association interrupting input device; and
a controller configured to interrupt control of the slave manipulator by a currently associated one of the first and second master manipulators upon user activation of the association interrupting input device, accept a user selection of one of the first and second master manipulators to be associated with the slave manipulator while disassociating a previously associated one of the first and second master manipulators, and associate the slave manipulator to the user selected one so that the tool is manipulatable according to manipulation of the selected one of the first and second master manipulators following user deactivation of the association interrupting input device.

8. The robotic surgical system according to claim 7, wherein the association interrupting device is a button manually activated by a user.

9. The robotic surgical system according to claim 7, wherein the association interrupting device is a foot pedal manually activated by a user.

10. The robotic surgical system according to claim 7, wherein the association interrupting device is voice controlled.

11. The robotic surgical system according to claim 7, wherein the association interrupting device is a computer mouse.

12. The robotic surgical system according to claim 7, wherein the tool is a surgical instrument.

13. The robotic surgical system according to claim 7, wherein the tool is an endoscope.

14. The robotic surgical system according to claim 7, wherein the first and second master manipulators are disposed so as to be controllable by a same operator.

15. The robotic surgical system according to claim 7, wherein the first and second master manipulators are disposed so as to be controllable by different operators.

16. A robotic surgical system comprising:
first and second slave manipulators respectively holding corresponding tools for performing a minimally invasive surgical procedure;
a master manipulator;
an association interrupting input device; and
a controller configured to interrupt control by the master manipulator of a currently associated one of the first and second slave manipulators upon user activation of the association interrupting input device, accept a user selection of one of the first and second slave manipulators to be associated with the master manipulator while disassociating a previously associated one of the first and second slave manipulators, and associate the master manipulator to the user selected one so that the corresponding tool of the user selected one of the first and second slave manipulators is manipulatable according to manipulation of the master manipulator following user deactivation of the association interrupting input device.

17. The robotic surgical system according to claim 16, wherein the association interrupting input device is one of a group of devices including a button, a foot pedal, a voice controlled device, and a computer mouse.

18. The robotic surgical system according to claim 16, wherein the tool is one of a group of devices including a surgical instrument and an endoscope.

19. The robotic surgical system according to claim 16, wherein the master manipulator is disengaged from controlling the first and second slave manipulators during user activation of the association interrupting device so that the master manipulator is usable as a user manipulatable computer mouse for user selection of one of the first and second slave manipulators to be associated with the master manipulator.

20. The robotic surgical system according to claim 19, further comprising a monitor, wherein the controller is further configured to display images of the first and second slave manipulators or their corresponding tools on the monitor and respond to user selection of one of the images using the user manipulatable computer mouse by associating the master manipulator to the one of the first and second slave manipulators to the user selected image so that the corresponding tool is manipulatable according to manipulation of the master manipulator following user deactivation of the association interrupting input device.

21. A robotic surgical system comprising:
a plurality of slave manipulators respectively holding corresponding tools for performing a minimally invasive surgical procedure;
a plurality of master manipulators;
an association interrupting input device operable by a user of one of the plurality of master manipulators; and
a controller configured to interrupt coupling between associated pairs of the plurality of slave manipulators and the plurality of master manipulators upon user activation of the association interrupting input device, receive a user selection of one of the plurality of slave manipulators to be associated with one of the plurality of master manipulators while disassociating a previously associated one of the plurality of slave manipulators, and associate the user selected one of the plurality of slave manipulators to the one of the plurality of master manipulators to be associated to, so that the corresponding tool of the user selected one of the plurality of slave manipulators is manipulatable according to the manipulation of the associated one of the plurality of master manipulators following user deactivation of the association interrupting input device.

22. The robotic surgical system according to claim 21, wherein the association interrupting input device is one of a group of devices including a button, a foot pedal, a voice controlled device, and a computer mouse.

23. The robotic surgical system according to claim 21, wherein the tool is one of a group of devices including a surgical instrument and an endoscope.

* * * * *